(12) United States Patent
Marban et al.

(10) Patent No.: US 8,617,877 B2
(45) Date of Patent: Dec. 31, 2013

(54) CARDIAC STEM CELL AND MYOCYTE SECRETED PARACRINE FACTORS

(75) Inventors: Eduardo Marban, Beverly Hills, CA (US); Jennifer E. Van Eyk, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 122 days.

(21) Appl. No.: 12/740,887

(22) PCT Filed: Nov. 3, 2008

(86) PCT No.: PCT/US2008/012415
§ 371 (c)(1),
(2), (4) Date: Jul. 23, 2010

(87) PCT Pub. No.: WO2009/061382
PCT Pub. Date: May 14, 2009

(65) Prior Publication Data
US 2011/0256105 A1    Oct. 20, 2011

Related U.S. Application Data

(60) Provisional application No. 61/001,792, filed on Nov. 2, 2007.

(51) Int. Cl.
*C12N 5/00* (2006.01)
*C12Q 1/00* (2006.01)

(52) U.S. Cl.
USPC ............................................. 435/325; 435/4

(58) Field of Classification Search
USPC .................................................... 435/325, 4
See application file for complete search history.

(56) References Cited

PUBLICATIONS

Nagaya et al. (Transplantation of Mesenchymal Stem Cells Improves Cardiac Function in a Rat Model of Dilated Cardiomyopathy. Circulation. 2005; 112:1128-1135).*
Assmus, B. et al., "Transcoronary transplantation of progenitor cells after myocardial infarction", N Engl J Med, 2006 vol. 21;355, pp. 1222-1232.
Coligan et al, sections 2.5.1-2.6.7.
Coligan et al., "Current Protocols in Immunology", Sec. 2.4.1 (1992), Kohler 7 Milstein (1975), Nature 256, 495.
Green et al., Production of Polyclonal Antisera, in Immunochemical Protocols (Manson, ed, Humana Press 1992.
Harlow et al, Antibodies, A Laboratory Manual, pp. 726 (Clod Spring Harbor Laboratory Pub. 1988).
Iravanian, S. et al., "Functional reentry in cultured monolayers of neonatal cardiac cells", *Am J Physiol Heart Circ Physiol*. 2003, vol. 285, pp. H449-H456.
Messina, E. et al., "Isolation and expansion of adult cardiac stem cells from human and murine heart", Circ Res. 2004, vol. 95, pp. 911-921.
Patel, A, et al., "Surgical treatment for congestive heart failure with autologous adult stem cell transplantation: a prospective randomized study", J Thorac Cardiovasc Surg. 2005, vol. 130(6), pp. 1631-1638.
Rota, M. et al., Bone marrow cells adopt the cardiomyogenic fate in vivo. Proc Natl Acad Sci U S A. Nov. 6, 2007 vol. 104(45), pp. 17783-17788.
Schuleri, K. et al., "Hare Early improvement in cardiac tissue perfusion due to mesenchymal stem cells", Am J Physiol Heart Circ Physiol. May 2008;2, vol. 94(5), pp. H2002-H2011.
Smith, R. et al., "Regenerative potential of cardiosphere-derived cells expanded from percutaneous endomyocardial biopsy specimen." *Circulation*. 2007, vol. 115, pp. 896-908.
Terrovitis, J. et al., Magnetic resonance imaging overestimates ferumoxide-labeled stem cell survival after transplantation in the heart. Mar. 25, 2008 vol. 117(12), pp. 1555-1562.

* cited by examiner

*Primary Examiner* — Karen Cochrane Carlson
*Assistant Examiner* — Natalie Moss
(74) *Attorney, Agent, or Firm* — Johns Hopkins Technology Transfer

(57) ABSTRACT

The invention relates to secreted proteins from cardiac stem cells (cardiospheres and cardiosphere-derived cells) or myocytes for diagnostic and/or therapeutic use.

4 Claims, 2 Drawing Sheets

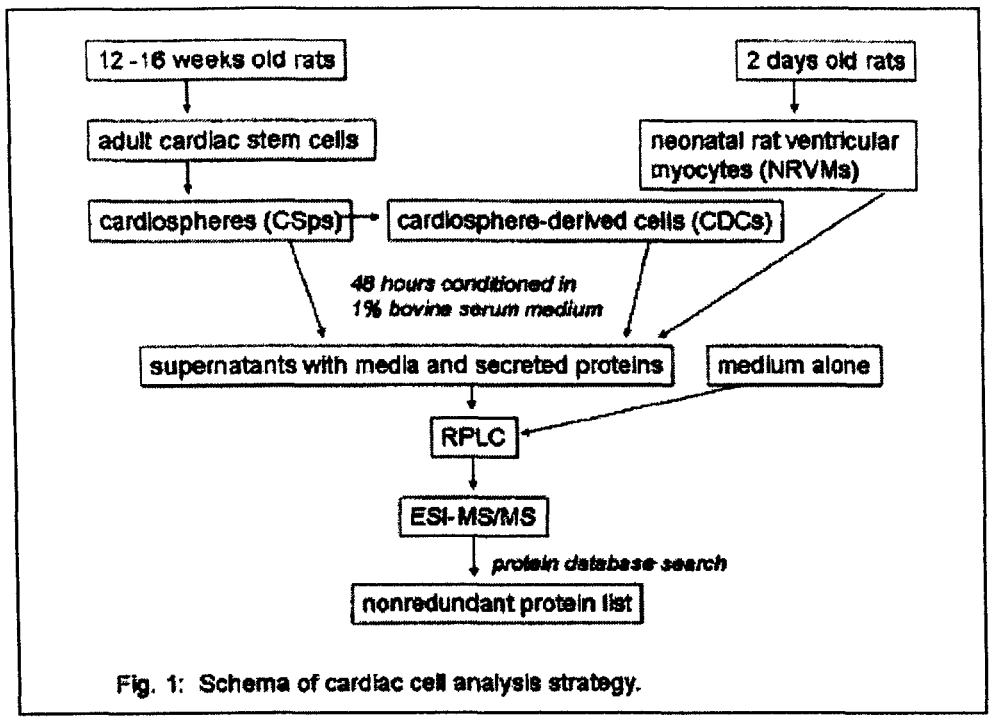

Fig. 1: Schema of cardiac cell analysis strategy.

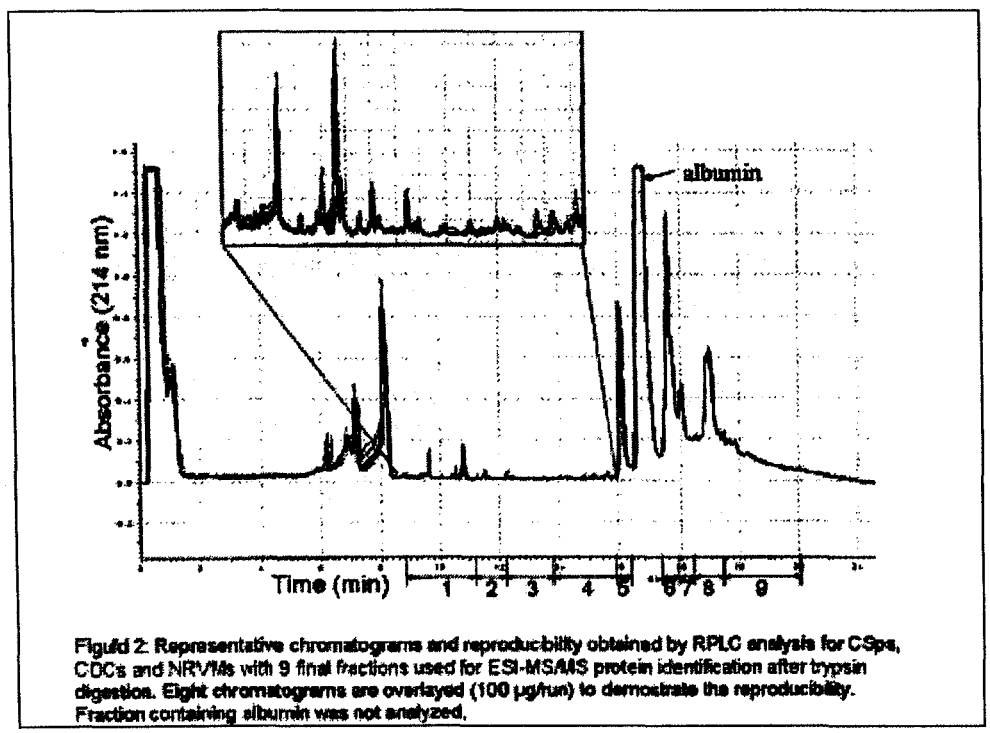

Figure 2: Representative chromatograms and reproducibility obtained by RPLC analysis for CSps, CDCs and NRVMs with 9 final fractions used for ESI-MS/MS protein identification after trypsin digestion. Eight chromatograms are overlayed (100 µg/run) to demostrate the reproducibility. Fraction containing albumin was not analyzed.

CARDIAC STEM CELL AND MYOCYTE SECRETED PARACRINE FACTORS

This application is a §371 of PCT Application No. PCT/US2008/012415, filed Nov. 3, 2008, which is a Non-Provisional of Application No. 61/001,792, filed Nov. 2, 2007, the entire contents of which are hereby incorporated by reference.

The research leading to this invention was supported in part by contract #NOI-HV-28180, U.S. National Heart, Lung and Blood Institute. The U.S. Government has certain rights in the invention.

1. FIELD OF THE INVENTION

The invention relates to secreted proteins from cardiac stem cells (cardiospheres and cardiosphere-derived cells) or myocytes for diagnostic and/or therapeutic use.

2. BACKGROUND

Stem cells hold the promise to revolutionize future reparative medicine through the development of stem cell-based therapies. Transplanting stem cells (either embryonic or adult derived) into damaged myocardium is emerging as a novel means for acute repair and as an alternative to organ transplantation or ventricular assist devices in the treatment of end-stage heart failure. The crux for the success of this therapy will lie in being able to manipulate proliferating ES cells to differentiate specifically into cardiac muscle upon demand, and to predict which patients will benefit from such intervention. An alternative approach is to harness the endogenous stem cells and remaining viable myocytes to regenerate the needed myocardium. This could be accomplished if a contusive environment at the site of injury could be therapeutically produced through the use (or augmentation) of soluble proteins and or paracine factors.

Existence of adult stem cells in mature tissues and organs such as bone marrow, brain, skin or liver has been demonstrated. Although adult stem cells are mostly considered to differentiate into cell types of tissue of their origin, they have also been found to form specialized cell types of other tissues. This transdifferentiation was reported for bone marrow stem cells, which can differentiate into e.g. cardiac cells (myocytes) and can induce cardiac regeneration. Although the heart has for considerable time been considered to be a terminally differentiated organ with cells not able to self-regenerate after injury or damage, the discovery of stem cells residing in heart has opened the possibility of their use for autologous heart cell repair. First reports about adult cardiac stem cells (CSCs) appeared in 2003 and from that time, the attempts to find the procedures for their isolation and expansion into sufficient quantity for therapeutic purposes have been made. Recently, successful methods for isolation and expansion of adult cardiac stem cells from heart biopsy specimens were reported. Endomyocardial biopsy specimen grown in primary culture developed spherical multicellular clusters, cardiospheres (CSps), which can be further plated yielding in cardiosphere-derived cells (CDCs)—expansion step to obtain reasonable numbers of cells for transplantation from small specimens in a timely manner. Cardiospheres and CDCs exhibit properties of stem cells, expressed certain markers characteristic for stem cells and promoted cardiac regeneration and function in a mouse infarct model.

SUMMARY

The present inventors have found that secreted proteins from cardiac stem cells or myocytes can be useful therapeutically in cardiac regenerative treatment by addition or by inducing enhanced cellular expression of one or more of proteins in isolated or cultured stem cells or myocytes prior to, at the time or following administration of therapy or they can be directly administered to the patient for enhancement of endogenous innate cardiac regeneration. Furthermore, detection of one or more of these proteins (fragment, isoform or modified form) and their binding partner(s) for diagnostic/prognostic assessment of patient viability and responsiveness to treatment and/or assessment of the regenerative potential of stem cells, directly. Thus, detection of one or more of these proteins and/or their binding partners allows better assessment and clinical intervention including regenerative therapy.

There is a need to be able to predict patients that will respond to stem cell therapy and the ability to manipulate the efficacy of stem cell therapy in heart, the monitoring and or application (exogenous delivery or endogenous enhance production) of paracrine factors from stem cells or myocytes maybe able to met these needs.

Particular embodiments of the invention include:

1. Unique stem cell-secreted paracrine factors found exclusively in the cardiac stem cell media include interleukin 1 receptor like protein (also named ST2) and brain acid soluble protein 1, cathepsin B, Cu/Zn superoxide dismutase, cystatin E/M, insulin-like growth factor binding protein 2 and minecan (for additional proteins, see Table 1). IL-33, the binding partner (analyte) of ST2 is also a target. All proteins which interact or bind to these proteins are also potential modulating proteins.

2. Unique myocyte secreted paracrine factors found exclusively in the myocyte media include atrial natriuretic peptide (ANP), apolipoprotien E, matrix metallopeptidase 2, metalloproteinase inhibitor 1, adrenomedullin and connective tissue growth factor (for additional proteins, see Table 1). Other proteins which interact or bind to these proteins are also potential modulating proteins.

3. Use of the above-mentioned factors, and related factors, to predict susceptibility to cardiovascular disease and or efficacy of treatment of cardiac (or other types) stem cell therapy or endogenous enhancement of stem cell therapy including response of either exogenously applied stem cells or the endogenous stem cells, myocyte or other cell types present in the Injured zone (fibroblasts).

4. The use of the above-mentioned secreted factors and/or their binding protein(s) alone or in combination to enhance honing, survival, engraftment and efficacy of stem cell therapy or cardiac regeneration therapy.

5. A method monitoring one or more factors as a means of protein diagnostic(s)/prognostic(s), for example to test efficacy of stem cells prior to therapy in blood of patients or cell culture or media used to produce/harvest cells for regeneration therapy.

6. A method monitoring one or more factors as a means of protein diagnostic(s)/prognostic(s) to assess patents inherent long term outcome of patent without treatment as well as to determine the potential responsiveness of patent to stem cell therapy.

7. A method for screening for cell populations isolated from patients based on the cells ability to secreted proteins or presence of their complementary cellular receptors to determine which cell population will be more suitable or more effective following injection into the patent.

8. A method of monitoring paracrine proteins and their binding proteins that allows clinician intervention during the course of stem cell therapy and the application of personalized stem cell therapy.

Interleukin-1 receptor (ST2), and its ligand IL33 as well as other paracrine factors including brain acid soluble protein 1, cathepsin B, Cu/Zn superoxide dismutase, cystatin E/M, insulin-like growth factor binding protein 2, and minecan, (for additional proteins, see Table 1) may increase the ability of stem cells (including cardiac or cardiac derived stem cells) to hone, survive or differentiation in the myocardial infracted zone as well as increase survival of the injured myocardium, fibroblasts or vascular tissue. In addition, the paracrine factors secreted from cardiac myocytes (healthy or injured) such as ANP (atrial natriuretic peptide), apolipoprotein E, matrix metallopeptidase 2, metalloproteinase inhibitor 1, adrenomedullin and connective tissue growth factor maybe work in a similar manner. Furthermore these proteins could affect the viability of the myocytes or their ability to transgenerate or alter other cell types (e.g. vascular smooth muscle cells or endothelial cells). Thus, paracrine factors from either or both stem cells and/or myocytes maybe used as a diagnostic monitor or prognostic indicator of i) their ability to be involved in regeneration or ii) viability of the cells. As well, the addition of one or more paracrine factor could enhance therapeutically the viability of the stem cells and surrounding cardiac or vascular tissue and or ability to differentiate. Finally, measurement of the paracrine factor in setting of heart failure, AMI or angina may predict outcome as a reflection of their ability for endogenous or therapeutic application of stem cell therapy. In addition, this is a method to screen for paracrine factors.

Diagnostic and prognostic markers can be used to measure cardiac stem cell and myocyte secreted factors and their binding partners for the in vivo assessment of the regeneration potential of individual patients. Specifically, ST2, its ligand IL33 and/or including brain acid soluble protein 1, cathepsin B, Cu/Zn superoxide dismutase, cystatin E/M, insulin-like growth factor binding protein 2 and minecan, atrial natriuretic peptide (ANP), apolipoprotein E, matrix metallopeptidase 2, metalloproteinase inhibitor 1, adrenomedullin and/or connective tissue growth factor (for additional proteins, see Table 1) can be used alone or in combination to provide a measurement of viability or efficacy of stem cell treatment or the long term regeneration potential of the injured myocardium (including but not exclusive to myocyte, fibroblast, endothelial, smooth muscle cells) in patients.

Diagnostic/prognostic markers can be used to measure cardiac stem cell and myocyte secreted paracrine factors and/or their binding partners for the assessment of the potency, viability and/or efficacy of the exogenous stem cells prior to therapeutic application. Specifically, ST2, its ligand IL33 and/or including brain acid soluble protein 1, cathepsin B, Cu/Zn superoxide dismutase, cystatin E/M insulin-like growth factor binding protein 2 and minecan, atrial natriuretic peptide (ANP), apolipoprotein E, matrix metallopeptidase 2, metalloproteinase inhibitor 1, adrenomedullin and/or connective tissue growth factor (for additional proteins, see Table 1), can be used alone or in combination to assess test viability, efficacy and suitability of stem cells or other cell types for transplantation and regeneration therapy.

Diagnostic/prognostic markers can be used alone or in combination to assess clinical outcome following acute myocardial infarction or heart failure as an indicator of the patients inherent ability to repair/regenerate injured myocardium by measuring one or more of the factors including ST2, IL33, brain acid soluble protein 1, cathepsin B, Cu/Zn superoxide dismutase, cystatin E/M, insulin-like growth factor binding protein 2 and minecan, atrial natriuretic peptide (ANP), apolipoprotein E, matrix metallopeptidase 2, metalloproteinase inhibitor 1, adrenomedullin and/or connective tissue growth factor (or their binding partners) in body fluid of patents (for additional proteins, see Table 1).

Therapeutic target or protein application of paracrine factor(s) and/or their binding partners can be used through endogenous administration or the use of a method to enhancement in vivo cellular release in individual patents in order to improve cardiac heart regeneration. Specifically, ST2, its ligand IL33 and/or including brain acid soluble protein 1, cathepsin B, Cu/Zn superoxide dismutase, cystatin E/M, insulin-like growth factor binding protein 2 and minecan, atrial natriuretic peptide (ANP), apolipoprotein E, matrix metallopeptidase 2, metalloproteinase inhibitor 1, adrenomedullin and/or connective tissue growth factor (or their binding partners) could be increased alone or in combination, in the myocardium (at or near site of injury) to enhance the in vivo cardiac and vascular regeneration and stem cell action. Protein(s) could be administered at the time of heart injury (e.g. at time of myocardial infarction or during development of heart failure), either alone, or in advance of or at the time of or following administration of endogenous stem cell.

Paracrine factor(s) and/or their binding partners can be used in stem cell culture to be used in regeneration therapy. Specifically, ST2, it ligand IL33 and/or including (but not exclusive) brain acid soluble protein 1, cathepsin B, Cu/Zn superoxide dismutase, cystatin E/M, insulin-like growth factor binding protein 2 and minecan, atrial natriuretic peptide (ANP), apolipoprotein E, matrix metallopeptidase 2, metalloproteinase inhibitor 1, adrenomedullin and connective tissue growth factor (see secreted factors Table 1), alone or in combination, can be added to the media of the cell culture to enhance preparation of stem cells prior to, at the time or following administration to patients.

Personalized medicine applications can be used in stem cell therapy, through the monitoring of paracrine proteins and their binding protein will allow clinician intervene, choose effective dose and time course of stem cells and proteins therapy during the course of stem cell therapy.

For adult autologous stem cell transplantation in subjects for whom therapy is to be performed, it is contemplated that $10^6$ to $10^8$ cells will be effective. These cells would be pretreated or injected at same time of the paracrine factors are added. Similar amounts of cardiac stem cells are expected to be effective. Determination of effective dosages can be done without undue experimentation by those of skill in the art. (See, e.g. [7-9]).

All proteins listed in the Tables herein maybe therapeutically important for cell survival, proliferation or deformation in the injured area of the heart. As well, they may be biomarkers for assessment of cell viability and effectiveness, responsiveness of the patent to stem cell therapy and long term prognosis of development of heart failure or survival. Equivalent proteins from humans or other species including isoforms, splice varients and polymorphorisms/SNPs are also expected to be effective. These are known to and can be tested by those of skill in the art without undue experimentation. Proteins considered to be particularly useful are listed in Table 2.

Another embodiment of the invention is a method to screen for paracrine factors from cells including stem cells. The method uses reversed phase HPLC to separate the intact proteins prior to MS.

This application claims priority to U.S. provisional application No. 61/001,792, filed Nov. 2, 2007, which is hereby incorporated by reference.

BRIEF DESCRIPTION OF THE DRAWINGS

FIG. 1: Cardiac cell analysis strategy

FIG. 2: Representative chromatograms and reproducibility obtained by RPLC analysis for CSps, CDCs and NRVms with 9 final fractions used for ESI-MS/MS protein identification after trypsin digestion. Eight chromatograms are overlaid (100 μg/run) to demonstrate the reproducibility. Fraction containing albumin was not analyzed.

DETAILED DESCRIPTION

Figures 3A, 3B, 3C:
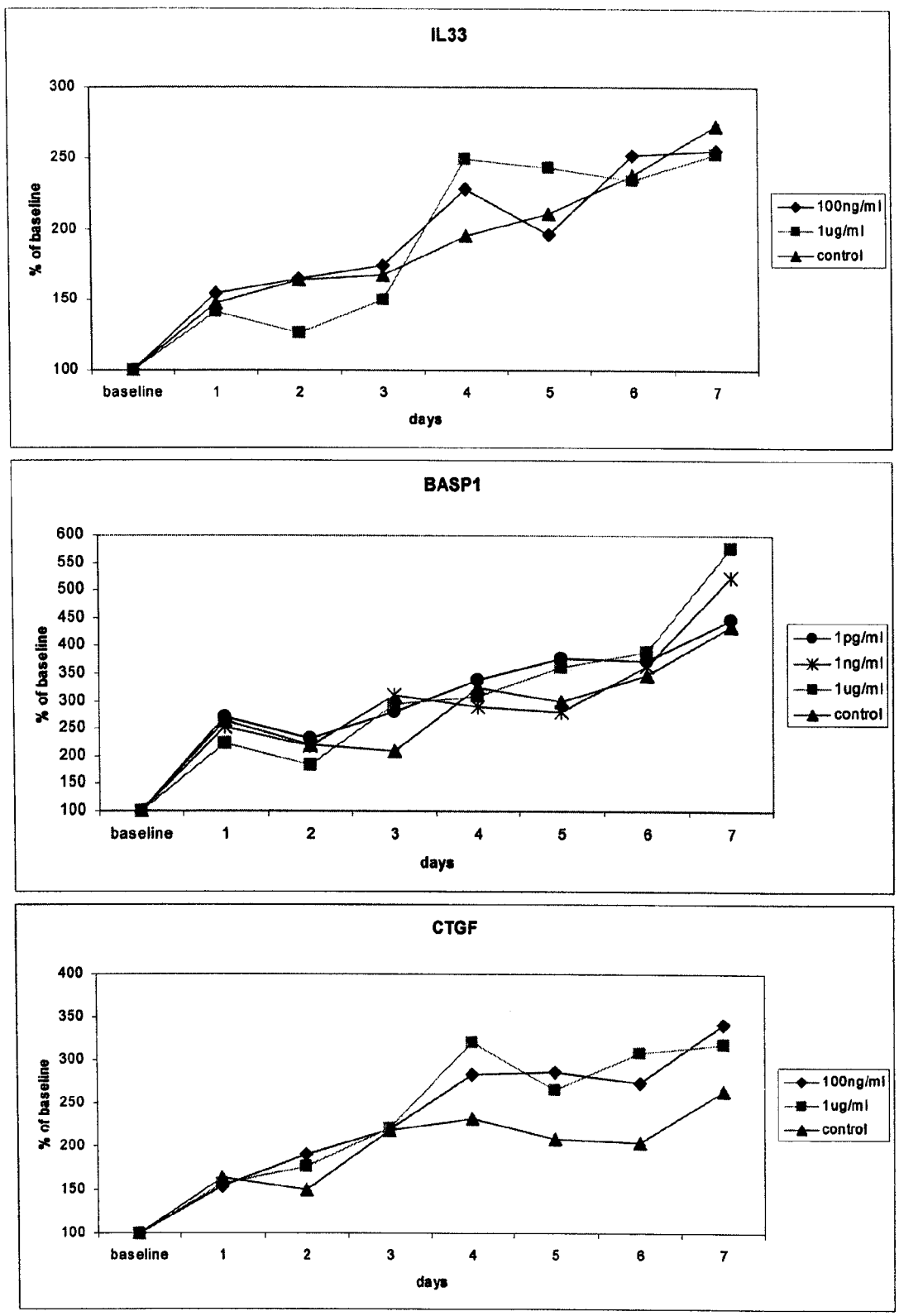
FIGS. 3A-3C: Influence of proteins IL33, BASP1 and CTCF at different concentrations on proliferation of CDCs. BASP1 and CTCF increases proliferation of CDCs. Three proteins identified as potentially important secreted proteins, IL33, BASP1 and CTCF, were tested at different concentrations on their ability to alter proliferation rate of rat CDCs. Detailed description is given in text. Note, CTCF began to alter proliferation by day 4 while BASP1 took longer and change was seen at day 7. On the other hand, IL33 had no affect during this time frame.

Soluble proteins secreted from stem cells of any cell type including the myocytes near or at the site of injury can serve as interactive signals to the local environment, influencing survival, differentiation and stem cell engraftment as well as affects on the injured myocardium. We have identified the secretome of cardiac stem cells (cardiospheres and cardiosphere-derived cells) and compared these proteins to those specifically secreted from isolated neonatal myocytes. This has allowed us to hone in on potential regulatory pathways that will allow modulation of the stem cells differentiation into cardiac myocytes.

The expression of any combination of the proteins, protein isoforms, protein polymorphorism, peptide fragment(s) protein with post-translational modifications thereof examined herein, or others, can be assayed with a method of the invention. For example, one can first measure the amount of expression of apolipoprotein E precursor compared to a baseline value, to determine if a significantly elevated or decreased amount is present in a patient sample. One can then further measure the amount of expression of adrenomedullin and/or Dkk3 protein compared to the baseline value. A significant increase (e.g. at least a statistically significant increase) in the amount of expression of one or more proteins, e.g. as listed in Table 2, compared to the baseline value indicates a greater likelihood that the patient is in need of, or would benefit from stem cell therapy.

By "peptide fragment" is meant any fragment of a protein of interest of at least 10 amino acid residues, preferably at least 15, 20, 15, or 30 amino acid residues up to fragments that may be only a few (e.g. 1, 2, 3, 4, 5, 10, 15, etc.) residues shorter than the full length protein. Unless otherwise indicated, the terms "protein, "polypeptide" and "peptide" are used interchangeably herein.

The amino acid sequences of the proteins of the invention, and the nucleic acids encoding them, are well-known and can be determined routinely, as well as downloaded from various known databases using the provided GenBank Accession numbers. See, e.g., the world wide web site, ncbi.nlm.nih.gov.

The amount of expression of a protein of the invention can be determined by measuring the amount of the protein, or by measuring the amount of mRNA encoding the protein. The amount of a protein can be determined using any routine method known in the art, e.g. MS, an antibody, etc. For example, the method can encompass binding the protein to an antibody which is specific for it, under conditions that are effective for specifically binding the protein to the antibody. For example, an antibody or any sensor may be contacted with a histological preparation, and the amount of protein is determined by immunohistochemical staining. The amount of an mRNA can be determined using a nucleic acid probe for the mRNA. For example, the method can encompass hybridizing the mRNA to a nucleic acid probe which is specific for it, under conditions that are effective for specifically hybridizing the mRNA and the probe.

Some methods involve the use of antibodies, any binding ligand or mass spectrometry tagged peptide specific for a protein of interest. Antibodies suitable for use in such assays are commercially available, or can be prepared routinely. Methods for preparing and using antibodies in assays for proteins of interest are conventional, and are described, e.g., in Green et al., Production of Polyclonal Antisera, in *Immunochemical Protocols* (Manson, ed.), (Humana Press 1992); Coligan et al., in *Current Protocols in Immunology*, Sec. 2.4.1 (1992); Kohler & Milstein (1975), *Nature* 256, 495; Coligan et al., sections 2.5.1-2.6.7; and Harlow et al., Antibodies: A Laboratory Manual, page 726 (Cold Spring Harbor Laboratory Pub. 1988).

Any of a variety of antibodies can be used, including, e.g., polyclonal, monoclonal (mAbs), recombinant, humanized or partially humanized, single chain, Fab, and fragments thereof. The antibodies can be of any isotype, e.g., IgM, various IgG isotypes such as $IgG_1$, $IgG_{2a}$, etc., and they can be from any animal species that produces antibodies, including goat, rabbit, mouse, chicken or the like. The term, an antibody "specific for" a protein, means that the antibody recognizes a defined sequence of amino acids, or epitope, in the protein, and binds selectively to the protein and not generally to proteins unintended for binding to the antibody. The parameters required to achieve specific binding can be determined routinely, using conventional methods in the art.

The baseline value for such measurements can be an average or mean from a population of normal subjects, i.e. those not suffering from heart disease, or, e.g. may be earlier measurements taken from the same patient, for example when progress of treatment is being monitored. Suitable baseline values can be determined by those of skill in the art without undue experimentation.

Thus, a "baseline value" refers to the expression, as determined by the levels (amounts) of mRNA and/or protein, in normal tissue (e.g., the same type of tissue as the tested tissue, such as normal cardiac tissue or normal serum), from normal subjects that do not have heart disease. If desired, a pool of the same tissues from normal subjects can be used. Such baseline values may be available in a database compiled from the values and/or may be determined based on published data or on retrospective studies of patients' tissues, and other information as would be apparent to a person of ordinary skill implementing a method of the invention. Suitable baseline values may be selected using statistical tools that provide an appropriate confidence interval so that measured levels that fall outside the standard value can be accepted as being aberrant from a diagnostic perspective, and predictive of success in treatment, diagnosis or prognosis.

A significantly elevated amount of an mRNA or a protein (or peptide fragment) of the invention compared to this baseline value, then, indicates that a patient or subject is likely to be responsive to stem cell therapy. If a protein whose expression is decreased in subjects that are expected to be less responsive, a significantly reduced amount of the protein or mRNA encoding it indicates that a test subject is less likely to respond.

A "significant" increase in the amount of a protein or mRNA, as used herein, can refer to a difference which is reproducible or statistically significant, as determined using statistical methods that are appropriate and well-known in the art, generally with a probability value of less than five percent chance of the change being due to random variation. Some such statistical tests are described in the Examples herein. For example, a significant increase in the amount of mRNA or protein compared to a baseline value can be at least about 2.5-fold (e.g., at least about 5-fold, 10-fold, 20-fold, 25-fold, or more) higher.

Methods for obtaining samples and preparing them for analysis (e.g., for detection of the amount of protein or mRNA encoding the protein) are conventional and well-known in the art.

A "subject" or "patient", as used herein, includes any animal that has, or may have, heart disease, including experimentally induced heart disease, for example in laboratory animals (such as mouse, rat, rabbit, or guinea pig), farm animals, and domestic animals or pets (such as a cat or dog). Non-human primates and human patients, are included. Heart failure can be induced following heart attack or other injuries to the heart (pulmonary hypertension), viral infections, genetic disorders and many other affectors that weaken the heart muscle or vasculature. Furthermore, following AMI when heart muscle has been injured or destroyed, regeneration is required to replace the lost muscle cells and other cells required for functioning heart.

A "sample" includes any biological sample, for example whole blood, serum, cardiac tissue, etc. obtained from a subject or patient. A sample also includes stem cell cultures, e.g. for therapeutic use in such patients.

By "stem cell therapy" is meant the administration of cardiac myocytes or equivalent cells as described herein to a cardiac patient or to an animal with experimentally induced heart disease. The paracrine factor(s) could alter the honing, survival, proliferation and differentiation of all stem cells and progenitor cells found in the body including EPC, mesochymal, and hemopoetic stem cell. Administration of cells can be by any means known in the art, for example, by local injection, infusion. Cells would be pretreated at optimal concentration most likely between pg/ml-1 µg/ml for a 10,000 cells (in 1 ml).

By "heart disease" is meant by stable and unstable angina, myocardial ischemia, myocardial stunning, acute myocardial infarction, (minor necrotic cell death, heart failure induced by myocardial infraction, genetic disease, pulmonary hypertension and other injury to the myocardium which makes the heart work harder.

By "treated" is meant that an effective amount of a chemotherapeutic drug or other anti-cancer procedure is administered to the subject. An "effective" treatment refers to a treatment that elicits a detectable response (e.g. a therapeutic response) in the subject.

By "effective amount" is meant any amount that will elicit a detectable clinical response.

A significant increase in the amount of expression of a secreted protein of the invention compared to the baseline value indicates that a subject is likely to be responsive to stem cell therapy. A subject that is "likely" to be responsive has greater than, e.g., at least about: a 25%, more likely 50%, 75%, chance to show an improvement in clinical symptoms.

EXAMPLES

In order to determine the specificity of the secreted proteome ("secretome"), we compared proteins secreted into media conditioning adult cardiac stem cells (CSps and CDC) to proteins secreted from neonatal rat ventricular myocytes after analysis by reversed phase liquid chromatography and identification by mass spectrometry (FIG. 1). The cells were obtained under optimized conditions that minimize cell lysis, allowing us to distinguish between secreted proteins and those proteins that would be liberated upon cell death due to necrosis and/or apoptosis.

Sample Processing

Specimen preparation, CSps, CDCs and NRVMs (rat neonatal myocytes) were harvested as previously described [1-3]. Briefly, cardiac tissue specimens from septum or left ventricule of Wistar Kyoto rats, 12 to 16 weeks old, were cut into small pieces, washed by PBS, enzymatically digested and grown in primary cultures as explants on fibronectin (from human plasma, BD Biosciences) coated Petri dishes in IMDM medium (Iscove's Modified Dulbecco's Medium, Invitrogen) supplemented with 20% fetal bovine serum (FBS), 1% penicillin-streptomycin, 1% L-glutamine and 0.1 mmol/L 2-mercaptoethanol at 37° C. and 5% $CO_2$. After a few days, round, phase-bright generated cells migrating over a layer of fibroblast-like cells arose from explants were harvested and seeded at $2-3\times10^4$ cells/mL on poly-D-lysine (BD Biosciences) coated Petri dishes in cardiosphere-growing medium composed of 35% IMDM/65% DMEM-Ham F-12 Mix (Invitrogen) and supplemented with 3.5% fetal bovine serum (FBS), 1% penicillin-streptomycin, 1% L-glutamine, 0.1 mmol/L 2-mercaptoethanol, thrombin (1 unit/mL, Sigma), B-27 (diluted at ratio 1:50, Invitrogen), basic fibroblast growth factor (bFGF, 80 ng/mL, PeproTech), epidermal growth factor (EGF, 25 ng/mL, PeproTech) and cardiotrophin-1 (4 ng/mL, PeproTech). The yielded spherical multicellular clusters-cardiospheres (CSps) were collected for proteomic analysis or further processed by plating on fibronectin-coated flasks and growing as monolayers giving finally cardiosphere-derived cells (CDCs). Neonatal rat ventricular myocytes (NRVMs) were isolated by routine methods with overnight trypsin digestion from 2 days old Sprague-Dawley rats. Cardiospheres and cardiosphere-derived cells were observed. The cells were isolated under conditions with minimal cell death (18±2% for CSps and CDCs, n=3 and 10±1% for NRVMs, n=3) as assessed by Annexin V labeling.

CSps, CDCs and NRVMs were further conditioned in media containing 1% FBS for 48 hours. After conditioning, media with cell secreted proteins were collected, filtered and concentrated in SpeedVac concentrator. Conditioning medium alone was processed the same way and served as control.

Reversed Phase Liquid Chromatography (RPLC)

The liquid concentrates with secreted proteins and concentrates of media alone were mixed with solvent to final concentration of 20% (v/v) acetonitrile (ACN), 1% (v/v) trifluoroacetic acid (TFA), pH 2.3, vortexed and spun down at 18×1000 g for 30 min at 4° C. Samples of intact proteins were separated by RPLC in order to reduce the complexity of protein mixtures prior to mass spectrometry protein identification. 200 or 800 µg were injected into C18 column (50 mm, nanoporous particles, HPRP model of ProteomeLab PF 2D, Beckman Coulter, Calif., USA) in consecutive runs of 100 µg/run in order to avoid the clogging of the column by the high amount of albumin, using a linear gradient from 0% to 100% ACN/0.08% TFA over 35 minutes. The chromatogram was recorded at an absorbance wavelength of 214 nm. FIG. 2 shows representative chromatographs of multiple runs as well as the fractions pooled for MS analysis. 68 fractions were collected per run from 7 to 24 min (0.25 min/fraction) and combined into 9 final fractions, dried in SpeedVac concentrator, neutralized by ammonium bicarbonate, trypsin digested overnight at 37° C. and analyzed by mass spectrometry for protein identification and quantification. Fractions containing major amounts of albumin (between and 17.25 min of elution time, 50-53% acetonitrile) were excluded.

Mass Spectrometry and Protein Identification

Dried samples with tryptic peptides after trypsin digestion of fractions were recovered in 8 μl of 0.1% (v/v) TFA and analyzed by a ThermoFinnigan LTQ ion trap with electrospray ionization or by a LTQ Orbitrap mass spectrometer (Thermo Electron Corporation, MA, USA). Data obtained from MS spectra were submitted to NCBInr database search by using MASCOT search engine (Matrix Science Mascot Daemon, V2.1.3-max. missed cleavages 2, peptide tolerance ±1.5 Da and MS/MS tol. ±0.8 Da, all species). After Mascot Daemon search, the files were transferred to Scaffold software (Version Scaffold-01_06_06, 2006 Proteome Software Inc., OR, USA) for Mascot result validation, visualization and comparison of protein identifications between individual samples. All identified proteins were further examined for peptide and protein redundancy. The protein amino acid sequence was blasted against UniProt Knowledgebase (Swiss-Prot+TrEMBL) by using SIB BLAST network service (ExPASy). In case of protein multiple names or homology, only one protein name was used after the original peptide sequences obtained from our MS results were checked back for matching that protein by using multiple sequence alignment program ClustalW (EMBL-EBI). Also, the confirmation of a protein isoform was done based on matching a tryptic peptide fragment to a unique amino acid sequence of isoform of the intact protein.

Results of MS Experiments

Three technical issues were overcome regarding analysis of the secretome, i) the secreted proteins are often at low concentration within the culture media, ii) the media is a large source of contamination (including albumin and iii) the need to distinguish between secreted proteins and those artificially liberated with cell death. This will be assessed this by both Annexin V labeling and increased detection of intercellular proteins (as outlined elsewhereherein). In Table 1 there are several protein highlighted which may arise from lysed cells due to their known intracellular location and the low level quantity present in the media. The remaining proteins are known to be secreted from cells or are membrane or membrane associated proteins.

To maximize proteome coverage it was also important to reduce serum content of the media which would hinder detection of low abundant proteins during proteomic analysis. Initially, we analyzed a series of CSps or CDCs obtained from rat heart biopsies to neonatal myocytes grown under different conditions ranging from 6 hours to 4 days in 0%, 1% and 2% serum. We elected to use conditioned media with 1% serum and to collect the media after 48 hours, although earlier time points also worked. The collected media was filtered, concentrated, suspended in 20% (v/v) acetonitrile: 1% TFA and separated by reversed phase HPLC using a linear gradient composed of 0.1% TFA and increasing concentrations of acetonitrile from 25% to 80%. Multiple fractions were collected, neutralized, digested with trypsin and analyzed by ESI/MS/MS for protein identification and quantification.

Example 1

We were able to observe 122 non-redundant proteins exclusively in media from cardiac stem cells or neonatal myocytes, with the majority (>90%) comprising known membrane, extracellular or secreted proteins. This indicates little contamination from dead cells. In the first set of experiments, greater than 2 fold more proteins were detected in cardiac stem cells than neonatal myocytes (60 vs. 27, respectively) and although the functional protein classes were conserved between the cell types, specific proteins and/or isoforms differed. Not surprisingly, we observed a large number of different collagen isoforms (10) with half (5) being cell-specific. Cell-specificity was also reflected with collagen regulation as TIMP2 and MMP2 were observed in neonatal myocytes and TIMP1 uniquely present in the cardiac stem cells. Interestingly, a recent study showed that proteins secreted from ESC (normal and hypoxic) could inhibit hydrogen peroxide induced apoptosis, and this inhibition was due, at least in part, to TIMP. On the other hand, MMP2 Is increased in heart failure in both animal models and patient samples.

Notable was the detection of two paracrine factors—the cardiac specific atrial natriuretic peptide or ANP was only detected in neonatal myocytes and not cardiac stem cells, while the soluble interleukin-1 receptor family member or ST2 was exclusive to cardiac stem cells (Table 1). ST2 is known to increase in myocytes with mechanical stress and heart failure where it has been linked to neurohormonal activation (e.g. (70,71) and reduces the endogenous affect of IL-33 (its ligand) of reducing hypertrophy and fibrosis. Furthermore, recently indirectly indicated at the gene level in C3H10T1/2 cells (a proliferative cell line) where ST2 is increased as is Wnt-5a, a know stem cell signaling factor.

Additional proteins that were found to be exclusively present in the media analyzed from cardiac stem cells or myocytes are listed in Table 1. Proteins that may play a role (alone or in combination) found exclusively in the myocyte media are apolipoprotien E, matrix metallopeptidase 2 (and although its inhibitor (metalloprotease 2 inhibitor) is not altered the ratio of these two proteins maybe critical), and metalloproteinase inhibitor 1 (and although the corresponding matrix metallopeptidase 1 is not observed, the ratio of the two proteins maybe important). In fact, all metalloproteinase and their inhibitors may play a role in both stem cell and myocyte function and survival in the infracted or injured area of the heart. Additional proteins found exclusively in the cardiac stem cell media are brain acid soluble protein 1, cathepsin B, Cu/Zn superoxide dismutase, cystatin E/M, and the insulin-like growth factor binding protein 2 (although not observed insulin growth factor (IGF) and other analytes that bind this protein or to the IGF receptor maybe important).

Brain soluble protein 1 is also named BASPI protein, neuronal axonal membrane protein NAP22 and the 22 kDa neuronal tissue-enriched acidic protein. This membrane protein is involved in cell projection and growth cones and was originally thought to be present exclusively in the brain. Cathepsin B also named APP secretase (APPS) contains a heavy and light chain within its amino acid sequence which after processing forms a dimmer with the heavy and light chains crosslinked by a disulfide bond. This protein in its active form is a thiol protease involved in degradation and turnover of proteins and is normally associated with the lysosome. Cystatin E/M is also called Cystatin M/E or cystatin 6 is a protease inhibitor. Insulin like growth factor binding protein 2 is also called IGFB-2, IBP-2 and IGF-binding protein 2 is secreted and prolongs the half life of the IGF and has been shown to alter growth promoting affects on IGF on cell cultures. IGF and the insulin like growth factor binding protein 2 have been implicated in changes to may cells types including fibroblasts, lung epithelial cells, and glial cells but to our knowledge not cardiac derived stem cells or the cardiac myocyte.

Example 2

In another set of experiments, we carried out independent duplicate analysis of the secretome from CDC, CSps and NRVMs obtained from left ventricle of rat hearts. We identified a total of 161 proteins. With this set of data we were able to expand our list of potential candidate paracrine factors. Of specific interest is adrenomedullin and connective tissue growth factor which are present in the media of NRMV exclusively and minecan which is found exclusively in the media of cardiac stem cells. Minecan also called osteoglycin or osteoinductive factor is known to induce bone formation in conjunction with TFG beta 1 or TGF beta 2, and have been implicated in regulation of collagen fibrillogeneis of the cardiac stem cells or act also on cells in the surrounding regions of the injured heart.

Adrenomedullin or AM is processed active domain of larger protein called ADML or ADM which also contains the proadrenomedullin N-20 terminal peptide (PAMP). AM and PAMP are potent hypotensive and vasodilator factors that have affects throughout the body including the kidney, brain and pituitary gland. It has been found in the ventricle. This protein has been implicated in differentiation of several stem cells but not cardiac derived cells or injured myocytes. Connective tissue growth factor is also termed hypertrophic chondrocyte-specific protein 24. This protein is a connective tissue mitoattractant that has been previously reported to be secreted by vascular endothelial cells but, to our knowledge not cardiac myocytes under normal physiological conditions but has been shown to increase in hearts with ongoing myocarditis.

Furthermore, AM has been shown to induce proliferation and differentiation of chondrocytes, improve cell adhesion for fibroblasts, myofibroblasts, endothelial and epithelial cells and stimulate fibroblast growth factor-induced DNA synthesis. Therefore, fibroblast growth factor alone or its ratio with respect to connective tissue growth factor may be also important.

Soluble proteins secreted from stem cells serve as interactive signals to the local environment, influencing survival, differentiation and engraftment. To characterize the secreted proteome ("secretome"), proteins found in the media conditioned by adult cardiac stem cells (CSCs) or neonatal rat ventricular myocytes (NRVMs) were obtained under optimized conditions that minimize cell lysis, allowing distinction between secreted proteins and those artificially liberated with cell death.

CSCs were grown from rat septal or left ventricular explants and NRVMs were isolated under conditions with minimal cell death (18±2% [CSCs, n=3] and 10±1% [NRVMs, n=3] by Annexin V labeling). Conditioned media (1% serum) was collected after 48 hours, filtered, concentrated, resuspended in 20% (v/v) acetontile: 1% TFA and separated by reversed phase HPLC. Collected fractions were digested with trypsin and analyzed by ESI/MS/MS for protein identification and quantification.

90-110 proteins were identified exclusively in media from CSCs or NRVMs, with the majority (>85%) comprising known membrane, extracellular or secreted proteins. Of these, >2 fold more proteins were detected in CSCs than NRVMs (60 vs. 27, respectively). Functional protein classes were conserved between the cell types, although proteins and/or their isoforms could differ. Of interest, 10 different collagen isoforms were observed with 5 being cell-specific. Cell-specificity was also reflected with collagen regulation as TIMP2 and MMP2 were observed in NRVMs while TIMP 1 was uniquely present in CSCs. The signaling molecules, insulin-like growth factor binding protein 6 and 3, were present in CSCs, but only isoform 7 in NRVMs. Interestingly, the cardiac specific natriuretic hormone ANP was only detected in NRVMs and not CSCs, while the soluble interleukin-1 receptor family member ST2 was exclusive to CSCs. ST2 is known to increase in myocytes with mechanical stress and heart failure where it has been linked to neurohormonal activation.

From these results, it is apparent that CSC and NRVM-specific secretomes display unique functionality including differential secretion of two cardiovascular hormones.

Example 3

Cell Proliferation Assay

Day 1: cardiosphere-derived cells from rat (CDCs) or neonatal myocytes or adult myocytes in IMDM medium (Iscove's Modified Dulbecco's Medium, Invitrogen) supplemented with 20% fetal bovine serum (FBS) were plated into 96-well plate in 8 rows except for blanks (last 2 wells in each row). Media (without the cells) were plated into last 2 wells of $1^{st}$ row. Cells were incubated in 37° C. incubator for 48 hours.
Day 3: the cells in wells were checked under microscope (the cells must be attached to the well bottoms). The media from all wells were aspired except for those of the $1^{st}$ row using sterile Pasteur pipette. Then, 100 μl of appropriate protein solutions with increasing concentrations 1 pg/ml, 1 ng/ml, 100 ng/ml, 1 μg/ml in IMDM medium supplemented with 10% FBS (treated cells; each in duplicate) and 100 ml of the same media without a protein (controls—untreated cells; in duplicate) were added to attached cells in wells of each row. Last 2 wells in each row were filled with 100 μl of only media (blanks).
10 μl of Cell Counting Kit-8 solution (Dojindo laboratories, Japan) were added to the $1^{st}$ row of the plate (avoiding a direct light exposure). The cells in plate were incubated in 37° C. incubator for 2 hours and after that the absorbances of solutions in $1^{st}$ row wells were read (λ=450 nm, SPECTRAmax M2, Molecular Devices, Sunnyvale, Calif.).
Day 4: 10 μl of Cell Counting Kit WST-8 solution were added to the $2^{nd}$ row of the plate, the cells in plate were incubated in 37° C. incubator for 2 hours and after that the absorbances of solutions were read.
Day 5 to 10: the procedure of day 4 was repeated on each following plate row. Influence of proteins interleukin-33 (IL 33, ALX-522-098-0010, Apotech Corporation, USA), brain abundant membrane attached signal protein 1 (BASP1, H00010409-P01, Novus Biological, USA) and connective tissue growth factor (CTGF, CRC604B, Cell Sciences, USA) at different concentration on CDCs proliferation is shown in FIG. 3.
Cell Migration Assay.
Modified Boyden chambers were equipped with 8 μm pore-size polycarbonate filters (Neuroprobe, Gaithersburg, Md.) coated with Matrigel (BD Bioscience, Palo Alto, Calif.). Cells (stem cells or myocytes) were either untreated or pretreated with appropriate protein for 24 hours. 220 μl of migration medium (DMEM-Dulbecco's Modified Eagle Medium with 0.1% BSA) was added to lower chamber with or without platelet-derived growth factor (PDGF) for chemattract and random migration assay, respectively. Cells ($10^6$/ml) were placed in upper chamber in 200 μl of migration medium, performed in triplicate. The assay was stopped after 4 hours at ° C. Cells that crossed the basement membrane and migrated to lower side of the filter were fixed and stained using HEMA3 system (Curtin, Matheson Scientific Inc., Houston, Tex.). Four random fields were counted at 400× magnification for each filter.

Oxidative Stress Assay.

To evaluate the effect of oxidative stress, the cells (NRVMs, myocytes or stem cells) were exposed to hydrogen peroxide for a fixed period of time (1 hour of 100 µmol/L $H_2O_2$). Mitochondrial membrane potential (determinant of myocytes viability) was measured by using flow cytometric analysis of tetramethylrhodamine ethyl ester (TMRE) loaded cells. TMRE (100 nmol/L) was loaded for 20 min in the dark at 37° C. Myocytes were subjected to flow cytometry by activation with the 488 nm wavelength. Fluorescence was monitored and influence of $H_2O_2$ on changes of mitochondrial membrane potential was determined.

Effect of the Proteins on Cell Morphology Combined with Immunochistochemistry (Immunostaining, Immunocytochemistry, IHC).

IHC is method for identification of specific tissue components by means of specific antigen/antibody (or other sensors) reaction tagged with a visible label (or other types of chemical labels). This method makes possible to visualize the distribution and localization of specific cellular components within a cell or tissue.

First, the tissue for staining is fixed. Fixative procedure is optimized based on tissue and antigen/sensor used and various fixatives can be used. Usually, the tissue is formalin fixed and paraffin embedded. Prior to staining, tissue slides are deparaffinized (e.g. in xylol) and rehydrated in graded alcohol series and can be further pretreated with proteolytic enzymes, washed in distilled water and heated in microwave oven for epitope retrieval. Then nonspecific sites are blocked with serum or blocker protein, incubated with primary antibody (1:100-1:1,000), washed and incubated with secondary antibody-enzyme conjugate (1:2,000-1:5,000), washed and incubated with substrate and finally, the stained tissue is visualized.

Western Blotting for Validation of Proteins Detected by Mass Spectrometry.

The CSps-, CDC-, NRVM-media with secreted proteins/lysates or adult myocyte lysates were subjected to 1D gel electrophoresis (NuPage BisTris gels of various concentrations, 200 V, 35 to 55 minutes based on running buffer and gel concentration used), separated proteins were transferred into nitrocellulose membrane (NuPage transfer buffer, 100 V, 1 hour). Proteins on the membrane were visualized by dye Direct Blue 71, briefly destained by 40% ethanol/10% acetic acid, washed by 1× Tris buffered saline solution (TBS; 20 mM Tris, 500 mM NaCl, pH 7.5) and transferred into blocking solution (5% of non fat dry milk in 1×TBS). The membrane was blocked overnight at 4° C., then washed by TTBS (0.1% Tween-20 in TBS) and incubated with appropriate primary antibody (1:100-1:1,000) for 4.5 hours. After that, the membrane was washed in TTBS and incubated with secondary antibody-enzyme conjugate (1:2,000-1:5,000), washed in TTBS and incubated with ImmunostarAP Substrate Pack (BioRad laboratories, CA, USA) for 5 minutes. The membrane was placed in cassette with film and developed.

Example 4

Animal Protocols

Tracking stem cells-rats/mice: Stem cells treated and nontreated are labeled with tracking agent such as iron as described by Terrovitis et al [4] or unique protein, chromosome, gene or chemical compound(s). For example, the ferumoxide-labeled CDCs (with and without treatment either exogenous protein or transgenically manipulated to produce proteins, see Smith et al. [5] for examples) is injected intramyocardially into normal (immunocompetent) rats or mice prior to or after induction of experimental of myocardial infarction. Rats may also undergo left thoracotomy in the fourth or fifth intercostals space under general anesthesia. The heart will be exposed and the cells injected directly into the myocardium at a single or multiple sites.

Myocardial infarction-rats/mice: The myocardial infarction can be produced by a number of methods including a permanent ligation of the left anterior descending coronary artery using a suture immediately before or after cell injection. Subsequently, the chest is closed and the animals are allowed to recover. Magnetic resonance imaging (MRI) images are obtained on a number of days after surgery such as day 2 and 21 or longer. After completion of this follow-up period, the rats will be sacrificed and the hearts subjected to histology.

MRI: For MRI, animals were anesthetized and then placed prone, head first in the magnet. ECG-gated cine images of the heart are obtained. At least 3 consecutive short-axis slices will be acquired to completely cover the area of cell injection. Signal intensity will be measured in the myocardium (remote areas and areas of cell injection); noise is measured by creating regions of interest in the lungs. Contrast-to-noise ratios (signal intensity in the remote myocardium minus signal intensity in the areas of the cell injection divided by the SD of noise) will be calculated for each slice in which the signal void is visualized. In addition, percent signal area will be calculated as the area of visually determined signal void (manually defined region of interest containing area obviously darker than the surrounding myocardium) divided by the total left ventricular area in the same slice. Histological analysis of cell engraftment will be performed for number of proteins and for general pathological stains.

Echocardiography and ventricular function-rats/mice: Echocardiography will be performed in conscious animals before and after myocardial infarction. The anterior chest area is shaved and 2D images and M-mode tracings are recorded from the parasternal short-axis view at the level of papillary muscles. In addition, it maybe needed to evaluate the LV pressure and + and −dP/dt in the closed-chest preparation. (for example see Rota et al. [6])

Cardiac anatomy. As well the abdominal aorta could be cannulated with a polyethylene catheter and the heart arrested in diastole (e.g. injection of $CdCl_2$), the thorax was opened, perfusion with phosphate buffer started. An aortic catheter connected to a pressure reservoir is used to adjust perfusion pressure to mean arterial blood pressure while simultaneously, the LV chamber is filled with formalin. After perfusion with buffer, the coronary vasculature is perfused with fixative. Subsequently, the heart is excised, and the weights and major axis from the base to the apex of the heart is measured. The volume of the myocardium is computed (4) by dividing the weight by the specific gravity of muscle tissue. Furthermore, paraffin-embedding of tissue could be done. In this case tissue slices would be stained with hematoxylin and eosin or used later for immunohistochemistry.

References cited herein are hereby incorporated by reference.

REFERENCES

[1] Messina E, De Angelis L, Frati G, Morrone S, Chimenti S, Fiordaliso F, Salio M, Battaglia M, Latronico M V G, Coletta M, Vivarelli E, Frati L, Cossu G, Giacomello A.

Isolation and expansion of adult cardiac stem cells from human and murine heart. *Circ Res.* 2004; 95:911-921.

[2] Smith R R, Barile L, Cho H C, Leppo M K, Hare J M, Messina E, Giacomello A, Abraham M R, Marban E. Regenerative potential of cardiosphere-derived cells expanded from percutaneous endomyocardial biopsy specimen. *Circulation.* 2007; 115:896-908.

[3] Iravanian S, Nabutovsky Y, Kong C R, Saha S, Bursac N, Tung L. Functional reentry in cultured monolayers of neonatal cardiac cells. *Am J Physiol Heart Circ Physiol.* 2003; 285:H449-H456.

[4] Terrovitis J, Stuber M, Youssef A, Preece S, Leppo M, Kizana E, Schar M, Gerstenblith G, Weiss R G, Marbán E, Abraham M R. Magnetic resonance imaging overestimates ferumoxide-labeled stem cell survival after transplantation in the heart. *Circulation.* 2008 Mar. 25; 117(12):1555-1562.

[5] Smith R R, Barile L, Cho H C, Leppo M K, Hare J M, Messina E, Giacomello A, Abraham M R, Marbán E. Regenerative potential of cardiosphere-derived cells expanded from percutaneous endomyocardial biopsy specimens. Circulation. 2007 Feb. 20; 115(7):896-908.

[6] Rota M, Kajstura J, Hosoda T, Bearzi C, Vitale S, Esposito G, Iaffaldano G, Padin-Iruegas M E, Gonzalez A, Rizzi R, Small N, Muraski J, Alvarez R, Chen X, Urbanek K, Bolli R, Houser S R, Leri A, Sussman M A, Anversa P. Bone marrow cells adopt the cardiomyogenic fate in vivo. *Proc Natl Acad Sci USA.* 2007 Nov. 6; 104(45):17783-17788.

[7] Patel A N, Geffner L, Vina R F, Saslaysky J, Urschel H C Jr, Kormos R, Benetti F. Surgical treatment for congestive heart failure with autologous adult stem cell transplantation: a prospective randomized study. J Thorac Cardiovasc Surg. 2005; 130(6):1631-8.

[8] Assmus B, Honold J, Schächinger V, Britten M B, Fischer-Rasokat U, Lehmann R, Teupe C, Pistorius K, Martin H, Abolmaali N D, Tonn T, Dimmeler S, Zeiher A M. Transcoronary transplantation of progenitor cells after myocardial infarction. N Engl J. Med. 2006 21; 355(12): 1222-32.)

[9] Schuleri K H, Amado L C, Boyle A J, Centola M, Saliaris A P, Gutman M R, Hatzistergos K E, Oskouei B N, Zimmet J M, Young R G, Heldman A W, Lardo A C, Hare Early improvement in cardiac tissue perfusion due to mesenchymal stem cells. Am J Physiol Heart Circ Physiol. 2008 May; 294(5):H2002-11.

---

We claim:

1. A method for screening a cardiac patient as a candidate for stem cell therapy, said method comprising measuring in a biological sample from the patient the amount of apolipoprotein E precursor, atriopeptigen (ANP, ANF), adrenomedullin, brain acid soluble protein 1 (BASP 1 protein), cathepsin B precursor, collagen alpha-1 (VI) chain precursor, connective tissue growth factor, cystatin E/M, Dkk3 protein, insulin-like growth factor-binding protein 2 precursor, interleukin-1 receptor-like 1 precursor (ST2), matrix metallopeptidase 2, metalloproteinase inhibitor 1 precursor (TIMP-1), metalloproteinase inhibitor 2 precursor (TIMP-2), mimecan precursor, procollagen type III alpha 1, procollagen type V alpha 1 and tropoelastin, comparing said measurement to a baseline value, wherein a statistically significant amount of the protein(s) compared to the baseline value indicates that the patient would be likely to benefit from stem cell therapy.

2. The method of claim 1, wherein the statistically significant amount represents at least a 5% increase over baseline value.

3. The method of claim 1, wherein the cardiac patient is suffering from angina, acute myocardial injury, cellular necrosis and myocardium hypertrophy or heart failure.

4. The method of claim 1, wherein the biological sample is a whole blood sample, serum sample, plasma sample, tissue biopsy sample, a sample of cultured cells derived from tissue, or a sample of circulating stem cells such as EPC.

* * * * *

SEQUENCE LISTING

```
<160> NUMBER OF SEQ ID NOS: 71

<210> SEQ ID NO 1
<211> LENGTH: 430
<212> TYPE: PRT
<213> ORGANISM: Rattus norvegicus

<400> SEQUENCE: 1

Met Ala Ala Arg Leu Leu Leu Arg Ser Leu Arg Val Leu Ser Ala Arg
1               5                   10                  15

Ser Ala Thr Leu Pro Pro Pro Ser Ala Arg Cys Ser His Ser Gly Ala
            20                  25                  30

Glu Ala Arg Leu Glu Thr Pro Ser Ala Lys Lys Leu Thr Asp Ile Gly
        35                  40                  45

Ile Arg Arg Ile Phe Ser Ser Glu His Asp Ile Phe Arg Glu Ser Val
    50                  55                  60

Arg Lys Phe Phe Gln Glu Glu Val Ile Pro Tyr His Glu Glu Trp Glu
65                  70                  75                  80

Lys Ala Gly Glu Val Ser Arg Glu Leu Trp Glu Lys Ala Gly Lys Gln
                85                  90                  95

Gly Leu Leu Gly Ile Asn Ile Ala Glu Lys His Gly Gly Ile Gly Gly
                100                 105                 110

Asp Leu Leu Ser Thr Ala Val Thr Trp Glu Glu Gln Ala Tyr Ser Asn
            115                 120                 125

Cys Thr Gly Pro Gly Phe Ser Leu His Ser Asp Ile Val Met Pro Tyr
        130                 135                 140

Ile Ala Asn Tyr Gly Thr Lys Glu Gln Ile Glu Gln Phe Ile Pro Gln
145                 150                 155                 160

Met Thr Ala Gly Lys Cys Ile Gly Ala Ile Ala Met Thr Glu Pro Gly
                165                 170                 175

Ala Gly Ser Asp Leu Gln Gly Val Arg Thr Asn Ala Lys Arg Ser Gly
                180                 185                 190

Ser Asp Trp Ile Leu Asn Gly Ser Lys Val Phe Ile Thr Asn Gly Trp
            195                 200                 205
```

-continued

```
Leu Ser Asp Leu Val Ile Val Ala Val Thr Asn Arg Glu Ala Arg
    210                 215                 220

Ser Pro Ala His Gly Ile Ser Leu Phe Leu Val Glu Asn Gly Met Lys
225                 230                 235                 240

Gly Phe Ile Lys Gly Lys Lys Leu His Lys Met Gly Met Lys Ala Gln
                245                 250                 255

Asp Thr Ala Glu Leu Phe Phe Glu Asp Val Arg Leu Pro Ala Ser Ala
            260                 265                 270

Leu Leu Gly Glu Glu Asn Lys Gly Phe Tyr Tyr Leu Met Gln Glu Leu
        275                 280                 285

Pro Gln Glu Arg Leu Leu Ile Ala Asp Leu Ala Ile Ser Ala Cys Glu
290                 295                 300

Phe Met Phe Glu Glu Thr Arg Asn Tyr Val Arg Gln Arg Lys Ala Phe
305                 310                 315                 320

Gly Lys Thr Val Ala His Ile Gln Thr Val Gln His Lys Leu Ala Glu
                325                 330                 335

Leu Lys Thr Asn Ile Cys Val Thr Arg Ala Phe Val Asp Ser Cys Leu
            340                 345                 350

Gln Leu His Glu Thr Lys Arg Leu Asp Ser Ala Ser Ala Ser Met Ala
        355                 360                 365

Lys Tyr Trp Ala Ser Glu Leu Gln Asn Thr Val Ala Tyr Gln Cys Val
370                 375                 380

Gln Leu His Gly Gly Trp Gly Tyr Met Trp Glu Tyr Pro Ile Ala Lys
385                 390                 395                 400

Ala Tyr Val Asp Ala Arg Val Gln Pro Ile Tyr Gly Gly Thr Asn Glu
                405                 410                 415

Ile Met Lys Glu Leu Ile Ala Arg Gln Ile Val Ser Asp Ser
            420                 425                 430

<210> SEQ ID NO 2
<211> LENGTH: 298
<212> TYPE: PRT
<213> ORGANISM: Rattus norvegicus

<400> SEQUENCE: 2

Met Thr Asp Ala Ala Val Ser Phe Ala Lys Asp Phe Leu Ala Gly Gly
1               5                   10                  15

Val Ala Ala Ala Ile Ser Lys Thr Ala Val Ala Pro Ile Glu Arg Val
                20                  25                  30

Lys Leu Leu Leu Gln Val Gln His Ala Ser Lys Gln Ile Thr Ala Asp
            35                  40                  45

Lys Gln Tyr Lys Gly Ile Ile Asp Cys Val Val Arg Ile Pro Lys Glu
        50                  55                  60

Gln Gly Val Leu Ser Phe Trp Arg Gly Asn Leu Ala Asn Val Ile Arg
65                  70                  75                  80

Tyr Phe Pro Thr Gln Ala Leu Asn Phe Ala Phe Lys Asp Lys Tyr Lys
                85                  90                  95

Gln Ile Phe Leu Gly Gly Val Asp Lys Arg Thr Gln Phe Trp Arg Tyr
            100                 105                 110

Phe Ala Gly Asn Leu Ala Ser Gly Gly Ala Ala Gly Ala Thr Ser Leu
        115                 120                 125

Cys Phe Val Tyr Pro Leu Asp Phe Ala Arg Thr Arg Leu Ala Ala Asp
    130                 135                 140

Val Gly Lys Ala Gly Ala Glu Arg Glu Phe Lys Gly Leu Gly Asp Cys
145                 150                 155                 160
```

```
Leu Val Lys Ile Tyr Lys Ser Asp Gly Ile Lys Gly Leu Tyr Gln Gly
            165                 170                 175

Phe Asn Val Ser Val Gln Gly Ile Ile Tyr Arg Ala Ala Tyr Phe
            180                 185                 190

Gly Ile Tyr Asp Thr Ala Lys Gly Met Leu Pro Asp Pro Lys Asn Thr
            195                 200                 205

His Ile Phe Ile Ser Trp Met Ile Ala Gln Ser Val Thr Ala Val Ala
    210                 215                 220

Gly Leu Thr Ser Tyr Pro Phe Asp Thr Val Arg Arg Met Met Met
225                 230                 235                 240

Gln Ser Gly Arg Lys Gly Thr Asp Ile Met Tyr Thr Gly Thr Leu Asp
            245                 250                 255

Cys Trp Arg Lys Ile Ala Arg Asp Glu Gly Gly Lys Ala Phe Phe Lys
            260                 265                 270

Gly Ala Trp Ser Asn Val Leu Arg Gly Met Gly Gly Ala Phe Val Leu
            275                 280                 285

Val Leu Tyr Asp Glu Ile Lys Lys Tyr Thr
            290                 295

<210> SEQ ID NO 3
<211> LENGTH: 185
<212> TYPE: PRT
<213> ORGANISM: Rattus norvegicus

<400> SEQUENCE: 3

Met Lys Leu Val Ser Ile Ala Leu Met Leu Leu Gly Ser Leu Ala Val
1               5                   10                  15

Leu Gly Ala Asp Thr Ala Arg Leu Asp Thr Ser Ser Gln Phe Arg Lys
            20                  25                  30

Lys Trp Asn Lys Trp Ala Leu Ser Arg Gly Lys Arg Glu Leu Gln Ala
        35                  40                  45

Ser Ser Ser Tyr Pro Thr Gly Leu Val Asp Glu Lys Thr Val Pro Thr
    50                  55                  60

Gln Thr Leu Gly Leu Gln Asp Lys Gln Ser Thr Ser Ser Thr Pro Gln
65                  70                  75                  80

Ala Ser Thr Gln Ser Thr Ala His Ile Arg Val Lys Arg Tyr Arg Gln
                85                  90                  95

Ser Met Asn Gln Gly Ser Arg Ser Thr Gly Cys Arg Phe Gly Thr Cys
            100                 105                 110

Thr Met Gln Lys Leu Ala His Gln Ile Tyr Gln Phe Thr Asp Lys Asp
        115                 120                 125

Lys Asp Gly Met Ala Pro Arg Asn Lys Ile Ser Pro Gln Gly Tyr Gly
    130                 135                 140

Arg Arg Arg Arg Arg Ser Leu Pro Glu Val Leu Arg Ala Arg Thr Val
145                 150                 155                 160

Glu Ser Ser Gln Glu Gln Thr His Ser Ala Pro Ala Ser Pro Ala His
                165                 170                 175

Gln Asp Ile Ser Arg Val Ser Arg Leu
            180                 185

<210> SEQ ID NO 4
<211> LENGTH: 364
<212> TYPE: PRT
<213> ORGANISM: Rattus norvegicus

<400> SEQUENCE: 4

Met Pro His Pro Tyr Pro Ala Leu Thr Pro Glu Gln Lys Lys Glu Leu
```

```
            1               5              10              15
Ala Asp Ile Ala His Arg Ile Val Ala Pro Gly Lys Gly Ile Leu Ala
                 20              25              30

Ala Asp Glu Ser Thr Gly Ser Ile Ala Lys Arg Leu Gln Ser Ile Gly
                 35              40              45

Thr Glu Asn Thr Glu Glu Asn Arg Arg Phe Tyr Arg Gln Leu Leu Leu
                 50              55              60

Thr Ala Asp Asp Arg Val Asn Pro Cys Ile Gly Val Ile Leu Phe
 65              70              75              80

His Glu Thr Leu Tyr Gln Lys Ala Asp Asp Gly Arg Pro Phe Pro Gln
                 85              90              95

Val Ile Lys Ser Lys Gly Gly Val Val Gly Ile Lys Val Asp Lys Gly
                100             105             110

Val Val Pro Leu Ala Gly Thr Asn Gly Glu Thr Thr Thr Gln Gly Leu
                115             120             125

Asp Gly Leu Ser Glu Arg Cys Ala Gln Tyr Lys Lys Asp Gly Ala Asp
                130             135             140

Ser Ala Lys Trp Arg Cys Val Leu Lys Ile Gly Glu His Thr Pro Ser
145             150             155             160

Ser Leu Ala Ile Val Glu Asn Ala Asn Val Leu Ala Arg Tyr Ala Ser
                165             170             175

Ile Cys Gln Gln Asn Gly Ile Val Pro Ile Val Glu Pro Glu Ile Leu
                180             185             190

Pro Asp Gly Asp His Asp Leu Lys Arg Cys Gln Tyr Val Thr Glu Lys
                195             200             205

Val Leu Ala Ala Val Tyr Lys Ala Leu Ser Asp His His Val Tyr Leu
                210             215             220

Glu Gly Thr Leu Leu Lys Pro Asn Met Val Thr Pro Gly His Ala Cys
225             230             235             240

Thr Gln Lys Phe Ser Asn Glu Glu Ile Ala Met Ala Thr Val Thr Ala
                245             250             255

Leu Arg Arg Thr Val Pro Pro Ala Val Pro Gly Val Thr Phe Leu Ser
                260             265             270

Gly Gly Gln Ser Glu Glu Glu Ala Ser Ile Asn Leu Asn Ala Ile Asn
                275             280             285

Lys Cys Pro Leu Leu Lys Pro Trp Ala Leu Thr Phe Ser Tyr Gly Arg
                290             295             300

Ala Leu Gln Ala Ser Ala Leu Lys Ala Trp Gly Gly Lys Lys Glu Asn
305             310             315             320

Leu Lys Ala Ala Gln Glu Glu Tyr Ile Lys Arg Ala Leu Ala Asn Ser
                325             330             335

Leu Ala Cys Gln Gly Lys Tyr Thr Pro Ser Gly Gln Ser Gly Ala Ala
                340             345             350

Ala Ser Glu Ser Leu Phe Ile Ser Asn His Ala Tyr
                355             360

<210> SEQ ID NO 5
<211> LENGTH: 312
<212> TYPE: PRT
<213> ORGANISM: Rattus norvegicus

<400> SEQUENCE: 5

Met Lys Ala Leu Trp Ala Leu Leu Leu Val Pro Leu Leu Thr Gly Cys
 1               5              10              15

Leu Ala Glu Gly Glu Leu Glu Val Thr Asp Gln Leu Pro Gly Gln Ser
```

```
            20                  25                  30
Asp Gln Pro Trp Glu Gln Ala Leu Asn Arg Phe Trp Asp Tyr Leu Arg
        35                  40                  45

Trp Val Gln Thr Leu Ser Asp Gln Val Gln Glu Glu Leu Gln Ser Ser
 50                  55                  60

Gln Val Thr Gln Glu Leu Thr Val Leu Met Glu Asp Thr Met Thr Glu
65                  70                  75                  80

Val Lys Ala Tyr Lys Lys Glu Leu Glu Glu Gln Leu Gly Pro Val Ala
                85                  90                  95

Glu Glu Thr Arg Ala Arg Leu Ala Lys Glu Val Gln Ala Ala Gln Ala
            100                 105                 110

Arg Leu Gly Ala Asp Met Glu Asp Leu Arg Asn Arg Leu Gly Gln Tyr
        115                 120                 125

Arg Asn Glu Val Asn Thr Met Leu Gly Gln Ser Thr Glu Glu Leu Arg
    130                 135                 140

Ser Arg Leu Ser Thr His Leu Arg Lys Met Arg Lys Arg Leu Met Arg
145                 150                 155                 160

Asp Ala Asp Asp Leu Gln Lys Arg Leu Ala Val Tyr Lys Ala Gly Ala
                165                 170                 175

Gln Glu Gly Ala Glu Arg Gly Val Ser Ala Ile Arg Glu Arg Leu Gly
            180                 185                 190

Pro Leu Val Glu Gln Gly Arg Gln Arg Thr Ala Asn Leu Gly Ala Gly
        195                 200                 205

Ala Ala Gln Pro Leu Arg Asp Arg Ala Gln Ala Leu Ser Asp Arg Ile
    210                 215                 220

Arg Gly Arg Leu Glu Glu Val Gly Asn Gln Ala Arg Asp Arg Leu Glu
225                 230                 235                 240

Glu Val Arg Glu Gln Met Glu Glu Val Arg Ser Lys Met Glu Glu Gln
                245                 250                 255

Thr Gln Gln Ile Arg Leu Gln Ala Glu Ile Phe Gln Ala Arg Ile Lys
            260                 265                 270

Gly Trp Phe Glu Pro Leu Val Glu Asp Met Gln Arg Gln Trp Ala Asn
        275                 280                 285

Leu Met Glu Lys Ile Gln Ala Ser Val Ala Thr Asn Ser Ile Ala Ser
    290                 295                 300

Thr Thr Val Pro Leu Glu Asn Gln
305                 310

<210> SEQ ID NO 6
<211> LENGTH: 298
<212> TYPE: PRT
<213> ORGANISM: Rattus norvegicus

<400> SEQUENCE: 6

Met Phe Ser Arg Ala Ser Ile Val Gly Leu Ser Ala Cys Ser Leu Gln
1               5                   10                  15

Pro Gln Trp Ile Gln Val Arg Asn Met Ala Thr Leu Lys Asp Ile Thr
            20                  25                  30

Arg Arg Leu Lys Ser Ile Lys Asn Ile Gln Lys Ile Thr Lys Ser Met
        35                  40                  45

Lys Met Val Ala Ala Ala Lys Tyr Ala Arg Ala Glu Arg Glu Leu Lys
    50                  55                  60

Pro Ala Arg Val Tyr Gly Thr Gly Ser Leu Ala Leu Tyr Glu Lys Ala
65                  70                  75                  80

Glu Ile Lys Gly Pro Glu Asp Lys Lys Lys His Leu Ile Ile Gly Val
```

```
                         85                  90                  95
Ser Ser Asp Arg Gly Leu Cys Gly Ala Ile His Ser Ser Val Ala Lys
            100                 105                 110

Gln Met Lys Asn Asp Met Ala Ala Leu Thr Ala Ala Gly Lys Glu Val
            115                 120                 125

Met Ile Val Gly Ile Gly Glu Lys Ile Lys Ser Ile Leu Tyr Arg Thr
        130                 135                 140

His Ser Asp Gln Phe Leu Val Ser Phe Lys Asp Val Gly Arg Lys Pro
145                 150                 155                 160

Pro Thr Phe Gly Asp Ala Ser Val Ile Ala Leu Glu Leu Leu Asn Ser
                165                 170                 175

Gly Tyr Glu Phe Asp Glu Gly Ser Ile Ile Phe Asn Gln Phe Lys Ser
            180                 185                 190

Val Ile Ser Tyr Lys Thr Glu Lys Pro Ile Phe Ser Phe Ser Thr
        195                 200                 205

Val Val Ala Ala Glu Asn Met Ser Ile Tyr Asp Ile Asp Ala Asp
    210                 215                 220

Val Leu Gln Asn Tyr Gln Glu Tyr Asn Leu Ala Asn Ile Ile Tyr Tyr
225                 230                 235                 240

Ser Leu Lys Glu Ser Thr Thr Ser Glu Gln Ser Ala Arg Met Thr Ala
                245                 250                 255

Met Asp Asn Ala Ser Lys Asn Ala Ser Asp Met Ile Asp Lys Leu Thr
            260                 265                 270

Leu Thr Phe Asn Arg Thr Arg Gln Ala Val Ile Thr Lys Glu Leu Ile
            275                 280                 285

Glu Ile Ile Ser Gly Ala Ala Ala Leu Asp
        290                 295

<210> SEQ ID NO 7
<211> LENGTH: 108
<212> TYPE: PRT
<213> ORGANISM: Rattus norvegicus

<400> SEQUENCE: 7

Met Thr Val Gln Arg Ile Phe Arg Leu Ser Val Leu Arg Ser Ala
1               5                   10                  15

Val Ser Val His Leu Arg Arg Asn Ile Gly Val Thr Ala Val Ala Phe
            20                  25                  30

Asn Lys Glu Leu Asp Pro Val Gln Lys Leu Phe Leu Asp Lys Ile Arg
        35                  40                  45

Glu Tyr Lys Ala Lys Arg Leu Ala Ser Gly Gly Pro Val Asp Thr Gly
    50                  55                  60

Pro Glu Tyr Gln Gln Glu Val Asp Arg Glu Leu Phe Lys Leu Lys Gln
65                  70                  75                  80

Met Tyr Gly Lys Gly Glu Met Asp Lys Phe Pro Thr Phe Asn Phe Glu
                85                  90                  95

Asp Pro Lys Phe Glu Val Leu Asp Lys Pro Gln Ser
            100                 105

<210> SEQ ID NO 8
<211> LENGTH: 152
<212> TYPE: PRT
<213> ORGANISM: Rattus norvegicus

<400> SEQUENCE: 8

Met Gly Ser Phe Ser Ile Thr Lys Gly Phe Phe Leu Phe Leu Ala Phe
1               5                   10                  15
```

```
Trp Leu Pro Gly His Ile Gly Ala Asn Pro Val Tyr Ser Ala Val Ser
             20                  25                  30

Asn Thr Asp Leu Met Asp Phe Lys Asn Leu Leu Asp His Leu Glu Glu
         35                  40                  45

Lys Met Pro Val Glu Asp Val Met Pro Gln Ala Leu Ser Glu
 50                  55                  60

Gln Thr Asp Glu Ala Gly Ala Ala Leu Ser Ser Leu Ser Glu Val Pro
 65                  70                  75                  80

Pro Trp Thr Gly Glu Val Asn Pro Ser Gln Arg Asp Gly Gly Ala Leu
                 85                  90                  95

Gly Arg Gly Pro Trp Asp Pro Ser Asp Arg Ser Ala Leu Leu Lys Ser
            100                 105                 110

Lys Leu Arg Ala Leu Leu Ala Gly Pro Arg Ser Leu Arg Arg Ser Ser
            115                 120                 125

Cys Phe Gly Gly Arg Ile Asp Arg Ile Gly Ala Gln Ser Gly Leu Gly
130                 135                 140

Cys Asn Ser Phe Arg Tyr Arg Arg
145                 150

<210> SEQ ID NO 9
<211> LENGTH: 220
<212> TYPE: PRT
<213> ORGANISM: Rattus norvegicus

<400> SEQUENCE: 9

Met Gly Ser Lys Leu Ser Lys Lys Lys Gly Tyr Asn Val Asn Asp
 1               5                  10                  15

Glu Lys Ala Lys Asp Lys Asp Lys Lys Ala Glu Gly Ala Gly Thr Glu
             20                  25                  30

Glu Glu Gly Thr Gln Lys Glu Ser Glu Pro Gln Ala Ala Ala Asp Ala
         35                  40                  45

Thr Glu Val Lys Glu Ser Ala Glu Glu Lys Pro Lys Asp Ala Ala Asp
 50                  55                  60

Gly Glu Ala Lys Ala Glu Leu Lys Glu Ala Asp Lys Ala Ala Ala Lys
 65                  70                  75                  80

Glu Glu Ala Pro Lys Ala Glu Pro Glu Lys Ser Glu Gly Ala Ala Glu
                 85                  90                  95

Glu Gln Pro Glu Pro Ala Pro Ala Pro Glu Gln Glu Ala Ala Ala Pro
            100                 105                 110

Gly Pro Ala Ala Gly Gly Glu Ala Pro Lys Ala Gly Glu Ala Ser Ala
            115                 120                 125

Glu Ser Thr Gly Ala Ala Asp Gly Ala Pro Gln Glu Glu Gly Glu Ala
130                 135                 140

Lys Lys Thr Glu Ala Pro Ala Ala Gly Pro Glu Ala Lys Ser Asp Ala
145                 150                 155                 160

Ala Pro Ala Ala Ser Asp Ser Lys Pro Ser Thr Glu Pro Ala Pro Ser
                165                 170                 175

Ser Lys Glu Thr Pro Ala Ala Ser Glu Ala Pro Ser Ser Ala Ala Lys
            180                 185                 190

Ala Pro Ala Pro Ala Ala Pro Ala Ala Glu Pro Gln Ala Glu Ala Pro
            195                 200                 205

Val Ala Ser Ser Glu Gln Ser Val Ala Val Lys Glu
210                 215                 220

<210> SEQ ID NO 10
```

```
<211> LENGTH: 906
<212> TYPE: PRT
<213> ORGANISM: Mus musculus

<400> SEQUENCE: 10
```

| | | | | | | | | | | | | | | |
|---|---|---|---|---|---|---|---|---|---|---|---|---|---|---|
| Met | Cys | Arg | Ile | Ala | Gly | Gly | Arg | Gly | Thr | Leu | Leu | Pro | Leu | Ala |
| 1 | | | | 5 | | | | | 10 | | | | | 15 |
| Ala | Leu | Leu | Gln | Ala | Ser | Val | Glu | Ala | Ser | Gly | Glu | Ile | Ala | Leu | Cys |
| | | | 20 | | | | | 25 | | | | | 30 | | |
| Lys | Thr | Gly | Phe | Pro | Glu | Asp | Val | Tyr | Ser | Ala | Val | Leu | Pro | Lys | Asp |
| | | 35 | | | | | 40 | | | | | 45 | | | |
| Val | His | Glu | Gly | Gln | Pro | Leu | Leu | Asn | Val | Lys | Phe | Ser | Asn | Cys | Asn |
| | 50 | | | | | 55 | | | | | 60 | | | | |
| Arg | Lys | Arg | Lys | Val | Gln | Tyr | Glu | Ser | Ser | Glu | Pro | Ala | Asp | Phe | Lys |
| 65 | | | | | 70 | | | | | 75 | | | | | 80 |
| Val | Asp | Glu | Asp | Gly | Thr | Val | Tyr | Ala | Val | Arg | Ser | Phe | Pro | Leu | Thr |
| | | | | 85 | | | | | 90 | | | | | 95 | |
| Ala | Glu | Gln | Ala | Lys | Phe | Leu | Ile | Tyr | Ala | Gln | Asp | Lys | Glu | Thr | Gln |
| | | | 100 | | | | | 105 | | | | | 110 | | |
| Glu | Lys | Trp | Gln | Val | Ala | Val | Asn | Leu | Ser | Arg | Glu | Pro | Thr | Leu | Thr |
| | | 115 | | | | | 120 | | | | | 125 | | | |
| Glu | Glu | Pro | Met | Lys | Glu | Pro | His | Glu | Ile | Glu | Glu | Ile | Val | Phe | Pro |
| 130 | | | | | 135 | | | | | 140 | | | | | |
| Arg | Gln | Leu | Ala | Lys | His | Ser | Gly | Ala | Leu | Gln | Arg | Gln | Lys | Arg | Asp |
| 145 | | | | | 150 | | | | | 155 | | | | | 160 |
| Trp | Val | Ile | Pro | Pro | Ile | Asn | Leu | Pro | Glu | Asn | Ser | Arg | Gly | Pro | Phe |
| | | | | 165 | | | | | 170 | | | | | 175 | |
| Pro | Gln | Glu | Leu | Val | Arg | Ile | Arg | Ser | Asp | Arg | Asp | Lys | Asn | Leu | Ser |
| | | | 180 | | | | | 185 | | | | | 190 | | |
| Leu | Arg | Tyr | Ser | Val | Thr | Gly | Pro | Gly | Ala | Asp | Gln | Pro | Pro | Thr | Gly |
| | | 195 | | | | | 200 | | | | | 205 | | | |
| Ile | Phe | Ile | Ile | Asn | Pro | Ile | Ser | Gly | Gln | Leu | Ser | Val | Thr | Lys | Pro |
| 210 | | | | | 215 | | | | | 220 | | | | | |
| Leu | Asp | Arg | Glu | Leu | Ile | Ala | Arg | Phe | His | Leu | Arg | Ala | His | Ala | Val |
| 225 | | | | | 230 | | | | | 235 | | | | | 240 |
| Asp | Ile | Asn | Gly | Asn | Gln | Val | Glu | Asn | Pro | Ile | Asp | Ile | Val | Ile | Asn |
| | | | | 245 | | | | | 250 | | | | | 255 | |
| Val | Ile | Asp | Met | Asn | Asp | Asn | Arg | Pro | Glu | Phe | Leu | His | Gln | Val | Trp |
| | | | 260 | | | | | 265 | | | | | 270 | | |
| Asn | Gly | Ser | Val | Pro | Glu | Gly | Ser | Lys | Pro | Gly | Thr | Tyr | Val | Met | Thr |
| | | 275 | | | | | 280 | | | | | 285 | | | |
| Val | Thr | Ala | Ile | Asp | Ala | Asp | Asp | Pro | Asn | Ala | Leu | Asn | Gly | Met | Leu |
| | 290 | | | | | 295 | | | | | 300 | | | | |
| Arg | Tyr | Arg | Ile | Leu | Ser | Gln | Ala | Pro | Ser | Thr | Pro | Ser | Pro | Asn | Met |
| 305 | | | | | 310 | | | | | 315 | | | | | 320 |
| Phe | Thr | Ile | Asn | Asn | Glu | Thr | Gly | Asp | Ile | Ile | Thr | Val | Ala | Ala | Gly |
| | | | | 325 | | | | | 330 | | | | | 335 | |
| Leu | Asp | Arg | Glu | Lys | Val | Gln | Gln | Tyr | Thr | Leu | Ile | Ile | Gln | Ala | Thr |
| | | | 340 | | | | | 345 | | | | | 350 | | |
| Asp | Met | Glu | Gly | Asn | Pro | Thr | Tyr | Gly | Leu | Ser | Asn | Thr | Ala | Thr | Ala |
| | | | 355 | | | | | 360 | | | | | 365 | | |
| Val | Ile | Thr | Val | Thr | Asp | Val | Asn | Asp | Asn | Pro | Pro | Glu | Phe | Thr | Ala |
| | 370 | | | | | 375 | | | | | 380 | | | | |
| Met | Thr | Phe | Tyr | Gly | Glu | Val | Pro | Glu | Asn | Arg | Val | Asp | Val | Ile | Val |
| 385 | | | | | 390 | | | | | 395 | | | | | 400 |

-continued

```
Ala Asn Leu Thr Val Thr Asp Lys Asp Gln Pro His Thr Pro Ala Trp
                405                 410                 415
Asn Ala Ala Tyr Arg Ile Ser Gly Gly Asp Pro Thr Gly Arg Phe Ala
                420                 425                 430
Ile Leu Thr Asp Pro Asn Ser Asn Asp Gly Leu Val Thr Val Val Lys
                435                 440                 445
Pro Ile Asp Phe Glu Thr Asn Arg Met Phe Val Leu Thr Val Ala Ala
                450                 455                 460
Glu Asn Gln Val Pro Leu Ala Lys Gly Ile Gln His Pro Pro Gln Ser
465                 470                 475                 480
Thr Ala Thr Val Ser Val Thr Val Ile Asp Val Asn Glu Asn Pro Tyr
                485                 490                 495
Phe Ala Pro Asn Pro Lys Ile Ile Arg Gln Glu Glu Gly Leu His Ala
                500                 505                 510
Gly Thr Met Leu Thr Thr Leu Thr Ala Gln Asp Pro Asp Arg Tyr Met
                515                 520                 525
Gln Gln Asn Ile Arg Tyr Thr Lys Leu Ser Asp Pro Ala Asn Trp Leu
                530                 535                 540
Lys Ile Asp Pro Val Asn Gly Gln Ile Thr Thr Ile Ala Val Leu Asp
545                 550                 555                 560
Arg Glu Ser Pro Tyr Val Gln Asn Asn Ile Tyr Asn Ala Thr Phe Leu
                565                 570                 575
Ala Ser Asp Asn Gly Ile Pro Pro Met Ser Gly Thr Gly Thr Leu Gln
                580                 585                 590
Ile Tyr Leu Leu Asp Ile Asn Asp Asn Ala Pro Gln Val Leu Pro Gln
                595                 600                 605
Glu Ala Glu Thr Cys Glu Thr Pro Glu Pro Asn Ser Ile Asn Ile Ala
                610                 615                 620
Ala Leu Asp Tyr Asp Ile Asp Pro Asn Ala Gly Pro Phe Ala Phe Asp
625                 630                 635                 640
Leu Pro Leu Ser Pro Val Thr Ile Lys Arg Asn Trp Thr Ile Asn Arg
                645                 650                 655
Leu Asn Gly Asp Phe Ala Gln Leu Asn Leu Lys Ile Lys Phe Leu Glu
                660                 665                 670
Ala Gly Ile Tyr Glu Val Pro Ile Ile Ile Thr Asp Ser Gly Asn Pro
                675                 680                 685
Pro Lys Ser Asn Ile Ser Ile Leu Arg Val Lys Val Cys Gln Cys Asp
                690                 695                 700
Ser Asn Gly Asp Cys Thr Asp Val Asp Arg Ile Val Gly Ala Gly Leu
705                 710                 715                 720
Gly Thr Gly Ala Ile Ile Ala Ile Leu Leu Cys Ile Ile Ile Leu Leu
                725                 730                 735
Ile Leu Val Leu Met Phe Val Val Trp Met Lys Arg Arg Asp Lys Glu
                740                 745                 750
Arg Gln Ala Lys Gln Leu Leu Ile Asp Pro Glu Asp Asp Val Arg Asp
                755                 760                 765
Asn Ile Leu Lys Tyr Asp Glu Glu Gly Gly Gly Glu Glu Asp Gln Asp
                770                 775                 780
Tyr Asp Leu Ser Gln Leu Gln Gln Pro Asp Thr Val Glu Pro Asp Ala
785                 790                 795                 800
Ile Lys Pro Val Gly Ile Arg Arg Leu Asp Glu Arg Pro Ile His Ala
                805                 810                 815
Glu Pro Gln Tyr Pro Val Arg Ser Ala Ala Pro His Pro Gly Asp Ile
```

-continued

```
                820                 825                 830
Gly Asp Phe Ile Asn Glu Gly Leu Lys Ala Ala Asp Asn Asp Pro Thr
            835                 840                 845

Ala Pro Pro Tyr Asp Ser Leu Leu Val Phe Asp Tyr Glu Gly Ser Gly
850                 855                 860

Ser Thr Ala Gly Ser Leu Ser Ser Leu Asn Ser Ser Ser Ser Gly Gly
865                 870                 875                 880

Asp Gln Asp Tyr Asp Tyr Leu Asn Asp Trp Gly Pro Arg Phe Lys Lys
                885                 890                 895

Leu Ala Asp Met Tyr Gly Gly Gly Asp Asp
            900                 905

<210> SEQ ID NO 11
<211> LENGTH: 476
<212> TYPE: PRT
<213> ORGANISM: Rattus norvegicus

<400> SEQUENCE: 11

Met Ala Gly Arg Gly Gly Arg Val Leu Leu Ala Leu Cys Ala Ala Leu
1               5                   10                  15

Val Ala Gly Gly Trp Leu Leu Ala Glu Ala Gln Glu Pro Gly Ala
            20                  25                  30

Pro Ala Ala Gly Met Arg Arg Arg Arg Leu Gln Gln Glu Asp Gly
        35                  40                  45

Ile Ser Phe Glu Tyr His Arg Tyr Pro Glu Leu Arg Glu Ala Leu Val
    50                  55                  60

Ser Val Trp Leu Gln Cys Thr Ala Ile Ser Arg Ile Tyr Thr Val Gly
65                  70                  75                  80

Arg Ser Phe Glu Gly Arg Glu Leu Leu Val Ile Glu Leu Ser Asp Asn
                85                  90                  95

Pro Gly Val His Glu Pro Gly Glu Pro Glu Phe Lys Tyr Ile Gly Asn
            100                 105                 110

Met His Gly Asn Glu Ala Val Gly Arg Glu Leu Leu Ile Phe Leu Ala
        115                 120                 125

Gln Tyr Leu Cys Asn Glu Tyr Gln Arg Gly Asn Glu Thr Ile Val Asn
    130                 135                 140

Leu Ile His Ser Thr Arg Ile His Ile Met Pro Ser Leu Asn Pro Asp
145                 150                 155                 160

Gly Phe Glu Lys Ala Ala Ser Gln Pro Gly Glu Leu Lys Asp Trp Phe
                165                 170                 175

Val Gly Arg Ser Asn Ala Gln Gly Ile Asp Leu Asn Arg Asn Phe Pro
            180                 185                 190

Asp Leu Asp Arg Ile Val Tyr Val Asn Glu Lys Glu Gly Gly Pro Asn
        195                 200                 205

Asn His Leu Leu Lys Asn Leu Lys Lys Ile Val Asp Gln Asn Ser Lys
    210                 215                 220

Leu Ala Pro Glu Thr Lys Ala Val Ile His Trp Ile Met Asp Ile Pro
225                 230                 235                 240

Phe Val Leu Ser Ala Asn Leu His Gly Gly Asp Leu Val Ala Asn Tyr
                245                 250                 255

Pro Tyr Asp Glu Thr Arg Ser Gly Thr Ala His Glu Tyr Ser Ser Cys
            260                 265                 270

Pro Asp Asp Ala Ile Phe Gln Ser Leu Ala Arg Ala Tyr Ser Ser Phe
        275                 280                 285

Asn Pro Val Met Ser Asp Pro Asn Arg Pro Pro Cys Arg Lys Asn Asp
```

```
                    290                 295                 300
Asp Asp Ser Ser Phe Val Asp Gly Thr Thr Asn Gly Gly Ala Trp Tyr
305                 310                 315                 320

Ser Val Pro Gly Gly Met Gln Asp Phe Asn Tyr Leu Ser Ser Asn Cys
                    325                 330                 335

Phe Glu Ile Thr Val Glu Leu Ser Cys Glu Lys Phe Pro Pro Glu Glu
                340                 345                 350

Thr Leu Lys Ser Tyr Trp Glu Asp Asn Lys Asn Ser Leu Ile Asn Tyr
                355                 360                 365

Leu Glu Gln Ile His Arg Gly Val Lys Gly Phe Val Arg Asp Leu Gln
370                 375                 380

Gly Asn Pro Ile Ala Asn Ala Thr Ile Ser Val Asp Gly Ile Asp His
385                 390                 395                 400

Asp Val Thr Ser Ala Lys Asp Gly Asp Tyr Trp Arg Leu Leu Val Pro
                405                 410                 415

Gly Asn Tyr Lys Leu Thr Ala Ser Ala Pro Gly Tyr Leu Ala Ile Thr
                420                 425                 430

Lys Lys Val Ala Val Pro Phe Ser Pro Ala Val Gly Val Asp Phe Glu
                435                 440                 445

Leu Glu Ser Phe Ser Glu Arg Lys Glu Glu Lys Glu Glu Leu Met
450                 455                 460

Glu Trp Trp Lys Met Met Ser Glu Thr Leu Asn Phe
465                 470                 475

<210> SEQ ID NO 12
<211> LENGTH: 214
<212> TYPE: PRT
<213> ORGANISM: Bos taurus

<400> SEQUENCE: 12

Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn
                20                  25                  30

Glu Asn Leu Leu Arg Phe Phe Val Ala Pro Phe Pro Glu Val Phe Gly
                35                  40                  45

Lys Glu Lys Val Asn Glu Leu Ser Lys Asp Ile Gly Ser Glu Ser Thr
            50                  55                  60

Glu Asp Gln Ala Met Glu Asp Ile Lys Glu Met Glu Ala Glu Ser Ile
65                  70                  75                  80

Ser Ser Ser Gly Glu Ile Val Pro Asn Ser Val Glu Gln Lys His Ile
                85                  90                  95

Gln Lys Glu Asp Val Pro Ser Glu Arg Tyr Leu Gly Tyr Leu Glu Gln
                100                 105                 110

Leu Leu Arg Leu Lys Lys Tyr Lys Val Pro Gln Leu Glu Ile Val Pro
            115                 120                 125

Asn Ser Ala Glu Glu Arg Leu His Ser Met Lys Glu Gly Ile Asp Ala
130                 135                 140

Gln Gln Lys Glu Pro Met Ile Gly Val Asn Gln Glu Leu Ala Tyr Phe
145                 150                 155                 160

Tyr Pro Glu Leu Phe Arg Gln Phe Tyr Gln Leu Asp Ala Tyr Pro Ser
                165                 170                 175

Gly Ala Trp Tyr Tyr Val Pro Leu Gly Thr Gln Tyr Thr Asp Ala Pro
                180                 185                 190

Ser Phe Ser Asp Ile Pro Asn Pro Ile Gly Ser Glu Asn Ser Glu Lys
```

Thr Thr Met Pro Leu Trp
    210

<210> SEQ ID NO 13
<211> LENGTH: 339
<212> TYPE: PRT
<213> ORGANISM: Rattus norvegicus

<400> SEQUENCE: 13

Met Trp Trp Ser Leu Ile Pro Leu Ser Cys Leu Leu Ala Leu Thr Ser
1               5                   10                  15

Ala His Asp Lys Pro Ser Ser His Pro Leu Ser Asp Asp Met Ile Asn
            20                  25                  30

Tyr Ile Asn Lys Gln Asn Thr Thr Trp Gln Ala Gly Arg Asn Phe Tyr
        35                  40                  45

Asn Val Asp Ile Ser Tyr Leu Lys Lys Leu Cys Gly Thr Val Leu Gly
    50                  55                  60

Gly Pro Asn Leu Pro Glu Arg Val Gly Phe Ser Glu Asp Ile Asn Leu
65                  70                  75                  80

Pro Glu Ser Phe Asp Ala Arg Glu Gln Trp Ser Asn Cys Pro Thr Ile
                85                  90                  95

Ala Gln Ile Arg Asp Gln Gly Ser Cys Gly Ser Cys Trp Ala Phe Gly
            100                 105                 110

Ala Val Glu Ala Met Ser Asp Arg Ile Cys Ile His Thr Asn Gly Arg
        115                 120                 125

Val Asn Val Glu Val Ser Ala Glu Asp Leu Leu Thr Cys Cys Gly Ile
    130                 135                 140

Gln Cys Gly Asp Gly Cys Asn Gly Gly Tyr Pro Ser Gly Ala Trp Asn
145                 150                 155                 160

Phe Trp Thr Arg Lys Gly Leu Val Ser Gly Gly Val Tyr Asn Ser His
                165                 170                 175

Ile Gly Cys Leu Pro Tyr Thr Ile Pro Pro Cys Glu His His Val Asn
            180                 185                 190

Gly Ser Arg Pro Pro Cys Thr Gly Glu Gly Asp Thr Pro Lys Cys Asn
        195                 200                 205

Lys Met Cys Glu Ala Gly Tyr Ser Thr Ser Tyr Lys Glu Asp Lys His
    210                 215                 220

Tyr Gly Tyr Thr Ser Tyr Ser Val Ser Asp Ser Glu Lys Glu Ile Met
225                 230                 235                 240

Ala Glu Ile Tyr Lys Asn Gly Pro Val Glu Gly Ala Phe Thr Val Phe
                245                 250                 255

Ser Asp Phe Leu Thr Tyr Lys Ser Gly Val Tyr Lys His Glu Ala Gly
            260                 265                 270

Asp Val Met Gly Gly His Ala Ile Arg Ile Leu Gly Trp Gly Ile Glu
        275                 280                 285

Asn Gly Val Pro Tyr Trp Leu Val Ala Asn Ser Trp Asn Val Asp Trp
    290                 295                 300

Gly Asp Asn Gly Phe Phe Lys Ile Leu Arg Gly Glu Asn His Cys Gly
305                 310                 315                 320

Ile Glu Ser Glu Ile Val Ala Gly Ile Pro Arg Thr Gln Gln Tyr Trp
                325                 330                 335

Gly Arg Phe

<210> SEQ ID NO 14

<211> LENGTH: 447
<212> TYPE: PRT
<213> ORGANISM: Rattus norvegicus

<400> SEQUENCE: 14

```
Met Lys Ile Leu Leu Cys Val Ala Leu Leu Thr Trp Asp Asn
1               5                   10                  15

Gly Met Val Leu Gly Glu Gln Glu Phe Ser Asp Asn Glu Leu Gln Glu
            20                  25                  30

Leu Ser Thr Gln Gly Ser Arg Tyr Val Asn Lys Glu Ile Gln Asn Ala
        35                  40                  45

Val Gln Gly Val Lys His Ile Lys Thr Leu Ile Glu Lys Thr Asn Ala
50                  55                  60

Glu Arg Lys Ser Leu Leu Asn Ser Leu Glu Glu Ala Lys Lys Lys
65                  70                  75                  80

Glu Gly Ala Leu Asp Asp Thr Arg Asp Ser Glu Met Lys Leu Lys Ala
            85                  90                  95

Phe Pro Glu Val Cys Asn Glu Thr Met Met Ala Leu Trp Glu Cys
            100                 105                 110

Lys Pro Cys Leu Lys His Thr Cys Met Lys Phe Tyr Ala Arg Val Cys
            115                 120                 125

Arg Ser Gly Ser Gly Leu Val Gly Arg Gln Leu Glu Glu Phe Leu Asn
    130                 135                 140

Gln Ser Ser Pro Phe Tyr Phe Trp Met Asn Gly Asp Arg Ile Asp Ser
145                 150                 155                 160

Leu Leu Glu Ser Asp Arg Gln Gln Ser Gln Val Leu Asp Ala Met Gln
                165                 170                 175

Asp Ser Phe Thr Arg Ala Ser Gly Ile Ile Asp Thr Leu Phe Gln Asp
            180                 185                 190

Arg Phe Phe Thr His Glu Pro Gln Asp Ile His His Phe Ser Pro Met
        195                 200                 205

Gly Phe Pro His Lys Arg Pro His Phe Leu Tyr Pro Lys Ser Arg Leu
    210                 215                 220

Val Arg Ser Leu Met Pro Leu Ser His Tyr Gly Pro Leu Ser Phe His
225                 230                 235                 240

Asn Met Phe Gln Pro Phe Phe Asp Met Ile His Gln Ala Gln Ala
                245                 250                 255

Met Asp Val Gln Leu His Ser Pro Ala Leu Gln Phe Pro Asp Val Asp
            260                 265                 270

Phe Leu Lys Glu Gly Glu Asp Asp Pro Thr Val Cys Lys Glu Ile Arg
        275                 280                 285

His Asn Ser Thr Gly Cys Leu Lys Met Lys Gly Gln Cys Glu Lys Cys
    290                 295                 300

Gln Glu Ile Leu Ser Val Asp Cys Ser Thr Asn Asn Pro Ala Gln Ala
305                 310                 315                 320

Asn Leu Arg Gln Glu Leu Asn Asp Ser Leu Gln Val Ala Glu Arg Leu
                325                 330                 335

Thr Gln Gln Tyr Asn Glu Leu Leu His Ser Leu Gln Ser Lys Met Leu
            340                 345                 350

Asn Thr Ser Ser Leu Leu Glu Gln Leu Asn Asp Gln Phe Thr Trp Val
        355                 360                 365

Ser Gln Leu Ala Asn Leu Thr Gln Gly Asp Asp Gln Tyr Leu Arg Val
    370                 375                 380

Ser Thr Val Thr Thr His Ser Ser Asp Ser Glu Val Pro Ser Arg Val
385                 390                 395                 400
```

```
Thr Glu Val Val Lys Leu Phe Asp Ser Asp Pro Ile Thr Val Val
            405                 410                 415

Leu Pro Glu Glu Val Ser Lys Asp Asn Pro Lys Phe Met Asp Thr Val
            420                 425                 430

Ala Glu Lys Ala Leu Gln Glu Tyr Arg Arg Lys Ser Arg Met Glu
            435                 440                 445

<210> SEQ ID NO 15
<211> LENGTH: 1025
<212> TYPE: PRT
<213> ORGANISM: Rattus norvegicus

<400> SEQUENCE: 15

Met Arg Leu Ala His Thr Leu Pro Leu Leu Gln Ala Cys Trp
1               5                   10                  15

Val Ala Ala Gln Asp Ile Gln Gly Ser Arg Ala Ile Ala Phe Gln Asp
                20                  25                  30

Cys Pro Val Asp Leu Phe Phe Val Leu Asp Thr Ser Glu Ser Val Ala
                35                  40                  45

Leu Arg Leu Lys Pro Tyr Gly Ala Leu Val Asp Lys Val Lys Ser Phe
        50                  55                  60

Thr Lys Arg Phe Ile Asp Asn Leu Arg Asp Arg Tyr Tyr Arg Cys Asp
65                  70                  75                  80

Arg Asn Leu Val Trp Asn Ala Gly Ala Leu His Tyr Ser Asp Glu Val
                85                  90                  95

Glu Ile Ile Arg Gly Leu Met Arg Met Pro Ser Gly Arg Asp Glu Leu
                100                 105                 110

Lys Ala Ser Ile Asp Ala Val Lys Tyr Phe Gly Lys Gly Thr Tyr Thr
                115                 120                 125

Asp Cys Ala Ile Lys Lys Gly Leu Glu Glu Leu Leu Ile Gly Gly Ser
                130                 135                 140

His Leu Lys Glu Asn Lys Tyr Leu Ile Val Val Thr Asp Gly His Pro
145                 150                 155                 160

Leu Glu Gly Tyr Lys Glu Pro Cys Gly Gly Leu Glu Asp Ala Val Asn
                165                 170                 175

Glu Ala Lys His Leu Gly Ile Lys Val Phe Ser Val Ala Ile Thr Pro
                180                 185                 190

Asp His Leu Glu Pro Arg Leu Ser Ile Ile Ala Thr Asp His Thr Tyr
                195                 200                 205

Arg Arg Asn Phe Thr Ala Ala Asp Trp Gly His Ser Arg Asp Ala Glu
        210                 215                 220

Glu Thr Ile Ser Gln Thr Ile Asp Thr Ile Val Asp Met Ile Lys Asn
225                 230                 235                 240

Asn Val Glu Gln Val Cys Cys Thr Phe Glu Cys Gln Ala Ala Arg Gly
                245                 250                 255

Pro Pro Gly Pro Arg Gly Asp Pro Gly Tyr Glu Gly Glu Arg Gly Lys
                260                 265                 270

Pro Gly Leu Pro Gly Glu Lys Gly Glu Ala Gly Asp Pro Gly Arg Pro
                275                 280                 285

Gly Asp Leu Gly Pro Val Gly Tyr Gln Gly Met Lys Gly Glu Lys Gly
                290                 295                 300

Ser Arg Gly Glu Lys Gly Ser Arg Gly Pro Lys Gly Tyr Lys Gly Glu
305                 310                 315                 320

Lys Gly Lys Arg Gly Ile Asp Gly Val Asp Gly Met Lys Gly Glu Thr
                325                 330                 335
```

```
Gly Tyr Pro Gly Leu Pro Gly Cys Lys Gly Ser Pro Gly Phe Asp Gly
            340                 345                 350

Ile Gln Gly Pro Pro Gly Pro Lys Gly Asp Ala Gly Ala Phe Gly Leu
            355                 360                 365

Lys Gly Glu Lys Gly Glu Ala Gly Ala Glu Gly Ala Gly Arg Pro
            370                 375                 380

Gly Asn Ser Gly Pro Pro Gly Asp Glu Gly Pro Gly Glu Pro Gly
385                 390                 395                 400

Pro Pro Gly Glu Lys Gly Glu Ala Gly Asp Glu Gly Asn Ala Gly Pro
                405                 410                 415

Asp Gly Ala Pro Gly Glu Arg Gly Gly Pro Gly Glu Arg Gly Pro Arg
                420                 425                 430

Gly Thr Pro Gly Val Arg Gly Pro Arg Gly Asp Pro Gly Glu Ala Gly
            435                 440                 445

Pro Gln Gly Asp Gln Gly Arg Glu Gly Pro Val Gly Ile Pro Gly Asp
450                 455                 460

Pro Gly Glu Ser Gly Pro Ile Gly Pro Lys Gly Tyr Arg Gly Asp Glu
465                 470                 475                 480

Gly Pro Pro Gly Pro Glu Gly Leu Arg Gly Ala Pro Gly Pro Val Gly
                485                 490                 495

Pro Pro Gly Asp Pro Gly Leu Met Gly Glu Arg Gly Glu Asp Gly Pro
                500                 505                 510

Pro Gly Asn Gly Thr Glu Gly Phe Pro Gly Phe Pro Gly Tyr Pro Gly
                515                 520                 525

Asn Arg Gly Pro Pro Gly Ile Asn Gly Thr Lys Gly Tyr Pro Gly Leu
530                 535                 540

Lys Gly Asp Glu Gly Glu Ala Gly Asp Pro Gly Glu Asp Asn Asn Asp
545                 550                 555                 560

Val Ser Pro Arg Gly Val Lys Gly Ala Lys Gly Tyr Arg Gly Pro Glu
                565                 570                 575

Gly Pro Gln Gly Pro Pro Gly His Val Gly Pro Pro Gly Pro Asp Glu
                580                 585                 590

Cys Glu Ile Leu Asp Ile Ile Met Lys Met Cys Ser Cys Cys Glu Cys
                595                 600                 605

Thr Cys Gly Pro Ile Asp Ile Leu Phe Val Leu Asp Ser Ser Glu Ser
            610                 615                 620

Ile Gly Leu Gln Asn Phe Glu Ile Ala Lys Asp Phe Ile Ile Lys Val
625                 630                 635                 640

Ile Asp Arg Leu Ser Lys Asp Glu Leu Val Lys Phe Glu Pro Gly Gln
                645                 650                 655

Ser His Ala Gly Val Val Gln Tyr Ser His Asn Gln Met Gln Glu His
                660                 665                 670

Val Asp Met Arg Ser Pro Asn Val Arg Asn Ala Gln Asp Phe Lys Glu
            675                 680                 685

Ala Val Lys Lys Leu Gln Trp Met Ala Gly Gly Thr Phe Thr Gly Glu
            690                 695                 700

Ala Leu Gln Tyr Thr Arg Asp Arg Leu Leu Pro Pro Thr Gln Asn Asn
705                 710                 715                 720

Arg Ile Ala Leu Val Ile Thr Asp Gly Arg Ser Asp Thr Gln Arg Asp
                725                 730                 735

Thr Thr Pro Leu Ser Val Leu Cys Gly Ser Asp Ile Gln Val Val Ser
            740                 745                 750

Val Gly Ile Lys Asp Val Phe Gly Phe Val Ala Gly Ser Asp Gln Leu
```

```
                        755                 760                 765
Asn Val Ile Ser Cys Gln Gly Leu Ser Gln Ser Arg Pro Gly Ile Ser
    770                 775                 780

Leu Val Lys Glu Asn Tyr Ala Glu Leu Leu Asp Asp Gly Phe Leu Lys
785                 790                 795                 800

Asn Ile Thr Ala Gln Ile Cys Ile Asp Lys Lys Cys Pro Asp Tyr Thr
                805                 810                 815

Cys Pro Ile Thr Phe Ser Ser Pro Thr Asp Ile Thr Ile Leu Leu Asp
            820                 825                 830

Ser Ser Ala Ser Val Gly Ser His Asn Phe Glu Thr Thr Lys Val Phe
        835                 840                 845

Ala Lys Arg Leu Ala Glu Arg Phe Leu Ser Ala Gly Arg Glu Asp Pro
    850                 855                 860

Thr Gln Val Val Arg Val Ala Val Val Gln Tyr Ser Gly Gln Gly Gln
865                 870                 875                 880

Gln Gln Pro Gly Arg Ala Ser Leu Gln Phe Gln Gln Asn Tyr Thr Val
                885                 890                 895

Leu Ala Ser Ser Val Asp Ser Met Asp Phe Ile Asn Asp Ala Thr Asp
            900                 905                 910

Val Asn Asp Ala Leu Ser Tyr Val Thr Arg Phe Tyr Arg Glu Asn Ser
        915                 920                 925

Ser Gly Ala Thr Lys Lys Arg Val Leu Leu Phe Ser Asp Gly Asn Ser
    930                 935                 940

Gln Gly Ala Thr Ala Glu Ala Ile Glu Lys Ala Val Gln Glu Ala Gln
945                 950                 955                 960

Arg Gly Gly Ile Glu Ile Phe Val Met Val Val Gly Pro Gln Val Asn
                965                 970                 975

Glu Pro His Ile Arg Val Leu Val Thr Gly Lys Thr Ala Glu Tyr Asp
            980                 985                 990

Val Ala Phe Gly Glu Arg His Leu  Phe Arg Val Pro Asn  Tyr Gln Ala
        995                 1000                1005

Leu Leu  Arg Gly Val Leu Tyr  Gln Thr Val Ser Arg  Lys Val Ala
    1010                1015                1020

Leu Gly
1025

<210> SEQ ID NO 16
<211> LENGTH: 347
<212> TYPE: PRT
<213> ORGANISM: Rattus norvegicus

<400> SEQUENCE: 16

Met Leu Ala Ser Val Ala Gly Pro Val Ser Leu Ala Leu Val Leu Leu
1               5                   10                  15

Leu Cys Thr Arg Pro Ala Thr Gly Gln Asp Cys Ser Ala Gln Cys Gln
            20                  25                  30

Cys Ala Ala Glu Ala Ala Pro Arg Cys Pro Ala Gly Val Ser Leu Val
        35                  40                  45

Leu Asp Gly Cys Gly Cys Cys Arg Val Cys Ala Lys Gln Leu Gly Glu
    50                  55                  60

Leu Cys Thr Glu Arg Asp Pro Cys Asp Pro His Lys Gly Leu Phe Cys
65                  70                  75                  80

Asp Phe Gly Ser Pro Ala Asn Arg Lys Ile Gly Val Cys Thr Ala Lys
                85                  90                  95

Asp Gly Ala Pro Cys Val Phe Gly Gly Ser Val Tyr Arg Ser Gly Glu
```

```
                    100                 105                 110
Ser Phe Gln Ser Ser Cys Lys Tyr Gln Cys Thr Cys Leu Asp Gly Ala
            115                 120                 125
Val Gly Cys Val Pro Leu Cys Ser Met Asp Val Arg Leu Pro Ser Pro
        130                 135                 140
Asp Cys Pro Phe Pro Arg Arg Val Lys Leu Pro Gly Lys Cys Cys Glu
145                 150                 155                 160
Glu Trp Val Cys Asp Glu Pro Lys Asp Arg Thr Val Val Gly Pro Ala
                165                 170                 175
Leu Ala Ala Tyr Arg Leu Glu Asp Thr Phe Gly Pro Asp Pro Thr Met
            180                 185                 190
Met Arg Ala Asn Cys Leu Val Gln Thr Thr Glu Trp Ser Ala Cys Ser
        195                 200                 205
Lys Thr Cys Gly Met Gly Ile Ser Thr Arg Val Thr Asn Asp Asn Thr
    210                 215                 220
Phe Cys Arg Leu Glu Lys Gln Ser Arg Leu Cys Met Val Arg Pro Cys
225                 230                 235                 240
Glu Ala Asp Leu Glu Glu Asn Ile Lys Lys Gly Lys Lys Cys Ile Arg
                245                 250                 255
Thr Pro Lys Ile Ala Lys Pro Val Lys Phe Glu Leu Ser Gly Cys Thr
            260                 265                 270
Ser Val Lys Thr Tyr Arg Ala Lys Phe Cys Gly Val Cys Thr Asp Gly
        275                 280                 285
Arg Cys Cys Thr Pro His Arg Thr Thr Thr Leu Pro Val Glu Phe Lys
    290                 295                 300
Cys Pro Asp Gly Glu Ile Met Lys Lys Asn Met Met Phe Ile Lys Thr
305                 310                 315                 320
Cys Ala Cys His Tyr Asn Cys Pro Gly Asp Asn Asp Ile Phe Glu Ser
                325                 330                 335
Leu Tyr Tyr Arg Lys Met Tyr Gly Asp Met Ala
            340                 345

<210> SEQ ID NO 17
<211> LENGTH: 155
<212> TYPE: PRT
<213> ORGANISM: Rattus norvegicus

<400> SEQUENCE: 17

Met Met Ala Thr Met Ala Val Cys Val Leu Lys Gly Asp Gly Pro Val
1               5                   10                  15
Gln Gly Val Ile His Phe Glu Gln Lys Ala Ser Gly Glu Pro Val Val
                20                  25                  30
Val Ser Gly Gln Ile Thr Gly Leu Thr Glu Gly Glu His Gly Phe His
            35                  40                  45
Val His Gln Tyr Gly Asp Asn Thr Gln Gly Cys Thr Thr Ala Gly Pro
        50                  55                  60
His Phe Asn Pro His Ser Lys Lys His Gly Gly Pro Ala Asp Glu Glu
65                  70                  75                  80
Arg His Val Gly Asp Leu Gly Asn Val Ala Ala Gly Lys Asp Gly Val
                85                  90                  95
Ala Asn Val Ser Ile Glu Asp Arg Val Ile Ser Leu Ser Gly Glu His
                100                 105                 110
Ser Ile Ile Gly Arg Thr Met Val Val His Glu Lys Gln Asp Asp Leu
            115                 120                 125
Gly Lys Gly Gly Asn Glu Glu Ser Thr Lys Thr Gly Asn Ala Gly Ser
```

```
                     130                 135                 140
Arg Leu Ala Cys Gly Val Ile Gly Ile Ala Gln
145                 150                 155

<210> SEQ ID NO 18
<211> LENGTH: 149
<212> TYPE: PRT
<213> ORGANISM: Bos taurus

<400> SEQUENCE: 18

Met Ala Arg Pro Ser Leu Leu Pro Met Ala Leu Ala Leu Leu Ala
1               5                   10                  15

Leu Cys Leu Leu Ala Leu Pro Arg Asp Ala Arg Ala Arg Pro Gly Asp
                20                  25                  30

Arg Lys Val Gly Glu Leu Gln Glu Leu Ser Pro Asn Asp Pro Gln Val
                35                  40                  45

Gln Lys Ala Ala Gln Val Ala Val Ala Asn Tyr Asn Met Gly Ser Asn
            50                  55                  60

Ser Asp Tyr Tyr Tyr Arg Asp Ile Thr Ile Leu Arg Ala His Ser Gln
65                  70                  75                  80

Leu Val Ala Gly Ile Lys Tyr Tyr Leu Thr Val Asp Met Gly Ser Thr
                85                  90                  95

Ala Cys Arg Lys Ser Ala Val Ala Gly Asp His Val Asp Leu Thr Thr
                100                 105                 110

Cys Pro Leu Ala Ala Glu Ala Gln Gln Glu Lys Leu Arg Cys Asp Phe
            115                 120                 125

Glu Ile Leu Val Val Pro Trp Lys Asn Ser Ser Gln Leu Leu Lys His
        130                 135                 140

Asp Cys Val Ser Leu
145

<210> SEQ ID NO 19
<211> LENGTH: 469
<212> TYPE: PRT
<213> ORGANISM: Mus musculus

<400> SEQUENCE: 19

Met Ser Gln Ala Tyr Ser Ser Ser Gln Arg Val Ser Ser Tyr Arg Arg
1               5                   10                  15

Thr Phe Gly Gly Ala Pro Gly Phe Ser Leu Gly Ser Pro Leu Ser Ser
                20                  25                  30

Pro Val Phe Pro Arg Ala Gly Phe Gly Thr Lys Gly Ser Ser Ser Ser
            35                  40                  45

Met Thr Ser Arg Val Tyr Gln Val Ser Arg Thr Ser Gly Gly Ala Gly
        50                  55                  60

Gly Leu Gly Ser Leu Arg Ser Ser Arg Leu Gly Thr Thr Arg Ala Pro
65                  70                  75                  80

Ser Tyr Gly Ala Gly Glu Leu Leu Asp Phe Ser Leu Ala Asp Ala Val
                85                  90                  95

Asn Gln Glu Phe Leu Ala Thr Arg Thr Asn Glu Lys Val Glu Leu Gln
                100                 105                 110

Glu Leu Asn Asp Arg Phe Ala Asn Tyr Ile Glu Lys Val Arg Phe Leu
            115                 120                 125

Glu Gln Gln Asn Ala Ala Leu Ala Ala Glu Val Asn Arg Leu Lys Gly
        130                 135                 140

Arg Glu Pro Thr Arg Val Ala Glu Leu Tyr Glu Glu Glu Met Arg Glu
145                 150                 155                 160
```

Leu Arg Arg Gln Val Glu Val Leu Thr Asn Gln Arg Ala Arg Val Asp
                165                 170                 175

Val Glu Arg Asp Asn Leu Ile Asp Asp Leu Gln Arg Leu Lys Ala Lys
            180                 185                 190

Leu Gln Glu Glu Ile Gln Leu Arg Glu Glu Ala Glu Asn Asn Leu Ala
        195                 200                 205

Ala Phe Arg Ala Asp Val Asp Ala Ala Thr Leu Ala Arg Ile Asp Leu
    210                 215                 220

Glu Arg Arg Ile Glu Ser Leu Asn Glu Glu Ile Ala Phe Leu Lys Lys
225                 230                 235                 240

Val His Glu Glu Glu Ile Arg Glu Leu Gln Ala Gln Leu Gln Glu Gln
            245                 250                 255

Gln Val Gln Val Glu Met Asp Met Ser Lys Pro Asp Leu Thr Ala Ala
        260                 265                 270

Leu Arg Asp Ile Arg Ala Gln Tyr Glu Thr Ile Ala Ala Lys Asn Ile
    275                 280                 285

Ser Glu Ala Glu Glu Trp Tyr Lys Ser Lys Val Ser Asp Leu Thr Gln
        290                 295                 300

Ala Ala Asn Lys Asn Asn Asp Ala Leu Arg Gln Ala Lys Gln Glu Met
305                 310                 315                 320

Met Glu Tyr Arg His Gln Ile Gln Ser Tyr Thr Cys Glu Ile Asp Ala
            325                 330                 335

Leu Lys Gly Thr Asn Asp Ser Leu Met Arg Gln Met Arg Glu Leu Glu
        340                 345                 350

Asp Arg Phe Ala Ser Glu Ala Asn Gly Tyr Gln Asp Asn Ile Ala Arg
    355                 360                 365

Leu Glu Glu Glu Ile Arg His Leu Lys Asp Glu Met Ala Arg His Leu
    370                 375                 380

Arg Glu Tyr Gln Asp Leu Leu Asn Val Lys Met Ala Leu Asp Val Glu
385                 390                 395                 400

Ile Ala Thr Tyr Arg Lys Leu Leu Glu Gly Glu Glu Ser Arg Ile Asn
            405                 410                 415

Leu Pro Ile Gln Thr Phe Ser Ala Leu Asn Phe Arg Glu Thr Ser Pro
        420                 425                 430

Glu Gln Arg Gly Ser Glu Val His Thr Lys Lys Thr Val Met Ile Lys
    435                 440                 445

Thr Ile Glu Thr Arg Asp Gly Glu Val Val Ser Glu Ala Thr Gln Gln
    450                 455                 460

Gln His Glu Val Leu
465

<210> SEQ ID NO 20
<211> LENGTH: 348
<212> TYPE: PRT
<213> ORGANISM: Rattus norvegicus

<400> SEQUENCE: 20

Met Gln Trp Leu Arg Asp Ile Leu Leu Cys Met Leu Leu Ala Ala Val
1               5                   10                  15

Val Pro Thr Ala Pro Thr Pro Ala Pro Thr Ala Thr Trp Thr Pro Ala
            20                  25                  30

Glu Pro Gly Pro Ala Leu Asn Tyr Pro Gln Glu Glu Ala Thr Leu Asn
        35                  40                  45

Glu Met Phe Arg Glu Val Glu Glu Leu Met Glu Asp Thr Gln His Lys
    50                  55                  60

Leu Arg Ser Ala Val Glu Glu Met Glu Ala Glu Ala Ala Arg
65                  70                  75                  80

Thr Ser Ser Glu Val Thr Leu Ser Ser Leu Pro Ala Asn Tyr His Asn
                85                  90                  95

Glu Thr Asn Thr Glu Thr Arg Met Glu Asn Asn Thr Ala His Val His
            100                 105                 110

Arg Glu Val His Lys Ile Thr Asn Asn Gln Ser Gly Gln Thr Val Phe
        115                 120                 125

Ser Glu Thr Val Ile Thr Ser Val Glu Asp Gly Glu Gly Lys Lys Ser
    130                 135                 140

His Glu Cys Ile Ile Asp Glu Asp Cys Gly Pro Thr Arg Tyr Cys Gln
145                 150                 155                 160

Phe Ser Ser Phe Lys Tyr Thr Cys Gln Pro Cys Arg Asp Gln Gln Met
                165                 170                 175

Leu Cys Thr Arg Asp Ser Glu Cys Cys Gly Asp Gln Leu Cys Ala Trp
            180                 185                 190

Gly His Cys Thr Gln Lys Ala Thr Lys Gly Ser Asn Gly Thr Ile Cys
        195                 200                 205

Asp Asn Gln Arg Asp Cys Gln Pro Gly Leu Cys Cys Ala Phe Gln Arg
    210                 215                 220

Gly Leu Leu Phe Pro Val Cys Thr Pro Leu Pro Val Glu Gly Glu Leu
225                 230                 235                 240

Cys His Asp Pro Thr Ser Gln Met Leu Asp Leu Ile Thr Trp Glu Leu
                245                 250                 255

Glu Pro Glu Gly Ala Leu Asp Arg Cys Pro Cys Ala Ser Gly Leu Leu
            260                 265                 270

Cys Gln Pro His Ser His Ser Leu Val Tyr Met Cys Lys Pro Ala Phe
        275                 280                 285

Val Gly Ser His Asp His Asn Glu Glu Ser Gln Leu Pro Arg Glu Ala
    290                 295                 300

Leu Asp Asp Tyr Glu Asp Val Gly Phe Ile Gly Glu Val Arg Gln Glu
305                 310                 315                 320

Leu Glu Asp Leu Glu Arg Ser Leu Ala Gln Glu Met Ala Phe Glu Glu
                325                 330                 335

Ala Thr Pro Val Asp Ser Leu Gly Gly Glu Lys Ile
            340                 345

<210> SEQ ID NO 21
<211> LENGTH: 463
<212> TYPE: PRT
<213> ORGANISM: Rattus norvegicus

<400> SEQUENCE: 21

Met Gly Lys Glu Lys Thr His Ile Asn Ile Val Val Ile Gly His Val
1               5                   10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
            35                  40                  45

Met Gly Lys Gly Ser Phe Lys Tyr Ala Trp Val Leu Asp Lys Leu Lys
        50                  55                  60

Ala Glu Arg Glu Arg Gly Ile Thr Ile Asp Ile Ser Leu Trp Lys Phe
65                  70                  75                  80

Glu Thr Thr Lys Tyr Tyr Ile Thr Ile Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
        115                 120                 125

Lys Asn Gly Gln Thr Arg Glu His Ala Leu Leu Ala Tyr Thr Leu Gly
    130                 135                 140

Val Lys Gln Leu Ile Val Gly Val Asn Lys Met Asp Ser Thr Glu Pro
145                 150                 155                 160

Ala Tyr Ser Glu Lys Arg Tyr Asp Glu Ile Val Lys Glu Val Ser Ala
                165                 170                 175

Tyr Ile Lys Lys Ile Gly Tyr Asn Pro Ala Thr Val Pro Phe Val Pro
            180                 185                 190

Ile Ser Gly Trp His Gly Asp Asn Met Leu Glu Pro Ser Pro Asn Met
        195                 200                 205

Pro Trp Phe Lys Gly Trp Lys Val Glu Arg Lys Glu Gly Asn Ala Ser
    210                 215                 220

Gly Val Ser Leu Leu Glu Ala Leu Asp Thr Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Ile Leu
            260                 265                 270

Arg Pro Gly Met Val Val Thr Phe Ala Pro Val Asn Ile Thr Thr Glu
        275                 280                 285

Val Lys Ser Val Glu Met His His Glu Ala Leu Ser Glu Ala Leu Pro
    290                 295                 300

Gly Asp Asn Val Gly Phe Asn Val Lys Asn Val Ser Val Lys Asp Ile
305                 310                 315                 320

Arg Arg Gly Asn Val Cys Gly Asp Ser Lys Ala Asp Pro Pro Gln Glu
                325                 330                 335

Ala Ala Gln Phe Thr Ser Gln Val Ile Ile Leu Asn His Pro Gly Gln
            340                 345                 350

Ile Ser Ala Gly Tyr Ser Pro Val Ile Asp Cys His Thr Ala His Ile
        355                 360                 365

Ala Cys Lys Phe Ala Glu Leu Lys Glu Lys Ile Asp Arg Arg Ser Gly
    370                 375                 380

Lys Lys Leu Glu Asp Asn Pro Lys Ser Leu Lys Ser Gly Asp Ala Ala
385                 390                 395                 400

Ile Val Glu Met Val Pro Gly Lys Pro Met Cys Val Glu Ser Phe Ser
                405                 410                 415

Gln Tyr Pro Pro Leu Gly Arg Phe Ala Val Arg Asp Met Arg Gln Thr
            420                 425                 430

Val Ala Val Gly Val Ile Lys Asn Val Glu Lys Lys Ser Gly Gly Ala
        435                 440                 445

Gly Lys Val Thr Lys Ser Ala Gln Lys Ala Gln Lys Ala Gly Lys
    450                 455                 460

<210> SEQ ID NO 22
<211> LENGTH: 2871
<212> TYPE: PRT
<213> ORGANISM: Mus musculus

<400> SEQUENCE: 22

Met Arg Arg Gly Gly Leu Leu Glu Val Ala Leu Ala Phe Ala Leu Leu
1               5                   10                  15

-continued

```
Leu Glu Ser Tyr Thr Ser His Gly Ala Asp Ala Asn Leu Glu Ala Gly
            20                  25                  30

Ser Leu Lys Glu Thr Arg Ala Asn Arg Ala Lys Arg Gly Gly Gly
            35                  40                  45

Gly His Asp Ala Leu Lys Gly Pro Asn Val Cys Gly Ser Arg Tyr Asn
            50                  55                  60

Ala Tyr Cys Cys Pro Gly Trp Lys Thr Leu Pro Gly Gly Asn Gln Cys
 65                  70                  75                  80

Ile Val Pro Ile Cys Arg His Ser Cys Gly Asp Gly Phe Cys Ser Arg
                 85                  90                  95

Pro Asn Met Cys Thr Cys Pro Ser Gly Gln Ile Ser Pro Ser Cys Gly
            100                 105                 110

Ser Arg Ser Ile Gln His Cys Asn Ile Arg Cys Met Asn Gly Gly Ser
            115                 120                 125

Cys Ser Asp Asp His Cys Leu Cys Gln Lys Gly Tyr Ile Gly Thr His
            130                 135                 140

Cys Gly Gln Pro Val Cys Glu Ser Gly Cys Leu Asn Gly Gly Arg Cys
145                 150                 155                 160

Val Ala Pro Asn Arg Cys Ala Cys Thr Tyr Gly Phe Thr Gly Pro Gln
                165                 170                 175

Cys Glu Arg Asp Tyr Arg Thr Gly Pro Cys Phe Thr Val Val Ser Asn
            180                 185                 190

Gln Met Cys Gln Gly Gln Leu Ser Gly Ile Val Cys Thr Lys Thr Leu
            195                 200                 205

Cys Cys Ala Thr Val Gly Arg Ala Trp Gly His Pro Cys Glu Met Cys
210                 215                 220

Pro Ala Gln Pro His Pro Cys Arg Arg Gly Phe Ile Pro Asn Ile Arg
225                 230                 235                 240

Thr Gly Ala Cys Gln Asp Val Asp Glu Cys Gln Ala Ile Pro Gly Met
                245                 250                 255

Cys Gln Gly Gly Asn Cys Ile Asn Thr Val Gly Ser Phe Glu Cys Lys
            260                 265                 270

Cys Pro Ala Gly His Lys Phe Asn Glu Val Ser Gln Lys Cys Glu Asp
            275                 280                 285

Ile Asp Glu Cys Ser Thr Ile Pro Gly Val Cys Asp Gly Gly Glu Cys
290                 295                 300

Thr Asn Thr Val Ser Ser Tyr Phe Cys Lys Cys Pro Pro Gly Phe Tyr
305                 310                 315                 320

Thr Ser Pro Asp Gly Thr Arg Cys Val Asp Val Arg Pro Gly Tyr Cys
                325                 330                 335

Tyr Thr Ala Leu Ala Asn Gly Arg Cys Ser Asn Gln Leu Pro Gln Ser
            340                 345                 350

Ile Thr Lys Met Gln Cys Cys Cys Asp Leu Gly Arg Cys Trp Ser Pro
            355                 360                 365

Gly Val Thr Val Ala Pro Glu Met Cys Pro Ile Arg Ser Thr Glu Asp
            370                 375                 380

Phe Asn Lys Leu Cys Ser Val Pro Leu Val Ile Pro Gly Arg Pro Glu
385                 390                 395                 400

Tyr Pro Pro Pro Ile Gly Pro Leu Pro Val Gln Pro Val Pro
                405                 410                 415

Pro Gly Tyr Pro Pro Gly Pro Val Ile Pro Val Pro Arg Pro Pro
            420                 425                 430

Glu Tyr Leu Tyr Pro Ser Arg Glu Pro Pro Arg Val Leu Pro Val Asn
```

```
                435                 440                 445
Val Thr Asp Tyr Cys Gln Leu Val Arg Tyr Leu Cys Gln Asn Gly Arg
450                 455                 460

Cys Ile Pro Thr Pro Gly Ser Tyr Arg Cys Glu Cys Asn Lys Gly Phe
465                 470                 475                 480

Gln Leu Asp Ile Arg Gly Glu Cys Ile Asp Val Asp Glu Cys Glu Lys
                485                 490                 495

Asn Pro Cys Thr Gly Gly Glu Cys Ile Asn Asn Gln Gly Ser Tyr Thr
                500                 505                 510

Cys His Cys Arg Ala Gly Tyr Gln Ser Thr Leu Thr Arg Thr Glu Cys
                515                 520                 525

Arg Asp Ile Asp Glu Cys Leu Gln Asn Gly Arg Ile Cys Asn Asn Gly
530                 535                 540

Arg Cys Ile Asn Thr Asp Gly Ser Phe His Cys Val Cys Asn Ala Gly
545                 550                 555                 560

Phe His Val Ser Ser Glu Gly Lys Asn Cys Glu Asp Met Asp Glu Cys
                565                 570                 575

Arg Thr Pro Asn Met Cys Pro Asn Gly Met Cys Ile Asn Glu Asp Gly
                580                 585                 590

Ser Phe Lys Cys Ile Cys Lys Pro Gly Phe Gln Leu Ala Ser Asp Gly
                595                 600                 605

Arg Tyr Cys Lys Asp Ile Asn Glu Cys Glu Thr Pro Gly Ile Cys Met
610                 615                 620

Asn Gly Arg Cys Val Asn Thr Asp Gly Ser Tyr Arg Cys Glu Cys Phe
625                 630                 635                 640

Pro Gly Leu Ala Val Gly Leu Asp Gly Arg Trp Cys Val Asp Thr His
                645                 650                 655

Met Arg Ser Ser Cys Tyr Gly Gly Tyr Arg Arg Gly Gln Cys Val Lys
                660                 665                 670

Pro Leu Phe Gly Ala Val Thr Lys Ser Glu Cys Cys Cys Ala Ser Thr
                675                 680                 685

Glu Tyr Ala Phe Gly Glu Pro Cys Gln Pro Cys Pro Ala Gln Asn Ser
690                 695                 700

Ala Glu Tyr Gln Ala Leu Cys Ser Ser Gly Pro Gly Met Thr Ser Ala
705                 710                 715                 720

Gly Thr Asp Ile Asn Glu Cys Ala Leu Asp Pro Asp Ile Cys Pro Asn
                725                 730                 735

Gly Ile Cys Glu Asn Leu Arg Gly Thr Tyr Lys Cys Ile Cys Asn Ser
                740                 745                 750

Gly Tyr Glu Val Asp Ile Thr Gly Lys Asn Cys Val Asp Ile Asn Glu
                755                 760                 765

Cys Val Leu Asn Ser Leu Leu Cys Asp Asn Gly Gln Cys Arg Asn Thr
770                 775                 780

Pro Gly Ser Phe Val Cys Thr Cys Pro Lys Gly Phe Val Tyr Lys Pro
785                 790                 795                 800

Asp Leu Lys Thr Cys Glu Asp Ile Asp Glu Cys Glu Ser Ser Pro Cys
                805                 810                 815

Ile Asn Gly Val Cys Lys Asn Ser Pro Gly Ser Phe Ile Cys Glu Cys
                820                 825                 830

Ser Pro Glu Ser Thr Leu Asp Pro Thr Lys Thr Ile Cys Ile Glu Thr
                835                 840                 845

Ile Lys Gly Thr Cys Trp Gln Thr Val Ile Asp Gly Arg Cys Glu Ile
850                 855                 860
```

-continued

Asn Ile Asn Gly Ala Thr Leu Lys Ser Glu Cys Cys Ser Leu Gly
865                 870                 875                 880

Ala Ala Trp Gly Ser Pro Cys Thr Ile Cys Gln Leu Asp Pro Ile Cys
            885                 890                 895

Gly Lys Gly Phe Ser Arg Ile Lys Gly Thr Gln Cys Glu Asp Ile Asn
                900                 905                 910

Glu Cys Glu Val Phe Pro Gly Val Cys Lys Asn Gly Leu Cys Val Asn
            915                 920                 925

Ser Arg Gly Ser Phe Lys Cys Glu Cys Pro Asn Gly Met Thr Leu Asp
930                 935                 940

Ala Thr Gly Arg Ile Cys Leu Asp Ile Arg Leu Glu Thr Cys Phe Leu
945                 950                 955                 960

Lys Tyr Asp Asp Glu Glu Cys Thr Leu Pro Ile Ala Gly Arg His Arg
                965                 970                 975

Met Asp Ala Cys Cys Cys Ser Val Gly Ala Ala Trp Gly Thr Glu Glu
            980                 985                 990

Cys Glu Glu Cys Pro Leu Arg Asn Ser Arg Glu Tyr Glu Glu Leu Cys
                995                 1000                1005

Pro Arg Gly Pro Gly Phe Ala Thr Lys Asp Ile Thr Asn Gly Lys
1010                1015                1020

Pro Phe Phe Lys Asp Ile Asn Glu Cys Lys Met Ile Pro Ser Leu
1025                1030                1035

Cys Thr His Gly Lys Cys Arg Asn Thr Ile Gly Ser Phe Lys Cys
1040                1045                1050

Arg Cys Asp Ser Gly Phe Ala Leu Asp Ser Glu Glu Arg Asn Cys
1055                1060                1065

Thr Asp Ile Asp Glu Cys Arg Ile Ser Pro Asp Leu Cys Gly Arg
1070                1075                1080

Gly Gln Cys Val Asn Thr Pro Gly Asp Phe Glu Cys Lys Cys Asp
1085                1090                1095

Glu Gly Tyr Glu Ser Gly Phe Met Met Met Lys Asn Cys Met Asp
1100                1105                1110

Ile Asp Glu Cys Gln Arg Asp Pro Leu Leu Cys Arg Gly Gly Ile
1115                1120                1125

Cys His Asn Thr Glu Gly Thr Tyr Arg Cys Glu Cys Pro Pro Gly
1130                1135                1140

His Gln Leu Ser Pro Asn Ile Ser Ala Cys Ile Asp Ile Asn Glu
1145                1150                1155

Cys Glu Leu Ser Ala Asn Leu Cys Pro His Gly Arg Cys Val Asn
1160                1165                1170

Leu Ile Gly Lys Tyr Gln Cys Ala Cys Asn Pro Gly Tyr His Pro
1175                1180                1185

Thr His Asp Arg Leu Phe Cys Val Asp Ile Asp Glu Cys Ser Ile
1190                1195                1200

Met Asn Gly Gly Cys Glu Thr Phe Cys Thr Asn Ser Asp Gly Ser
1205                1210                1215

Tyr Glu Cys Ser Cys Gln Pro Gly Phe Ala Leu Met Pro Asp Gln
1220                1225                1230

Arg Ser Cys Thr Asp Ile Asp Gln Cys Glu Asp Asn Pro Asn Ile
1235                1240                1245

Cys Asp Gly Gly Gln Cys Thr Asn Ile Pro Gly Glu Tyr Arg Cys
1250                1255                1260

Leu Cys Tyr Asp Gly Phe Met Ala Ser Glu Asp Met Lys Thr Cys
1265                1270                1275

-continued

```
Val Asp Val Asn Glu Cys Asp Leu Asn Pro Asn Ile Cys Leu Ser
    1280              1285              1290

Gly Thr Cys Glu Asn Thr Lys Gly Ser Phe Ile Cys His Cys Asp
    1295              1300              1305

Met Gly Tyr Ser Gly Lys Lys Gly Lys Thr Gly Cys Thr Asp Ile
    1310              1315              1320

Asn Glu Cys Glu Ile Gly Ala His Asn Cys Gly Arg His Ala Val
    1325              1330              1335

Cys Thr Asn Thr Ala Gly Ser Phe Lys Cys Ser Cys Ser Pro Gly
    1340              1345              1350

Trp Ile Gly Asp Gly Ile Lys Cys Thr Asp Leu Asp Glu Cys Ser
    1355              1360              1365

Asn Gly Thr His Met Cys Ser Gln His Ala Asp Cys Lys Asn Thr
    1370              1375              1380

Met Gly Ser Tyr Arg Cys Leu Cys Lys Asp Gly Tyr Thr Gly Asp
    1385              1390              1395

Gly Phe Thr Cys Thr Asp Leu Asp Glu Cys Ser Glu Asn Leu Asn
    1400              1405              1410

Leu Cys Gly Asn Gly Gln Cys Leu Asn Ala Pro Gly Gly Tyr Arg
    1415              1420              1425

Cys Glu Cys Asp Met Gly Phe Val Pro Ser Ala Asp Gly Lys Ala
    1430              1435              1440

Cys Glu Asp Ile Asp Glu Cys Ser Leu Pro Asn Ile Cys Val Phe
    1445              1450              1455

Gly Thr Cys His Asn Leu Pro Gly Leu Phe Arg Cys Glu Cys Glu
    1460              1465              1470

Ile Gly Tyr Glu Leu Asp Arg Ser Gly Gly Asn Cys Thr Asp Val
    1475              1480              1485

Asn Glu Cys Leu Asp Pro Thr Thr Cys Ile Ser Gly Asn Cys Val
    1490              1495              1500

Asn Thr Pro Gly Ser Tyr Thr Cys Asp Cys Ser Pro Asp Phe Glu
    1505              1510              1515

Leu Asn Pro Thr Arg Val Gly Cys Val Asp Thr Arg Ser Gly Asn
    1520              1525              1530

Cys Tyr Leu Asn Ile Arg Pro Arg Gly Asp Asn Gly Asp Thr Ala
    1535              1540              1545

Cys Ser Asn Glu Ile Gly Val Gly Val Ser Lys Ala Ser Cys Cys
    1550              1555              1560

Cys Ser Leu Gly Lys Ala Trp Gly Thr Pro Cys Glu Leu Cys Pro
    1565              1570              1575

Ser Val Asn Thr Ser Glu Tyr Lys Ile Leu Cys Pro Gly Gly Glu
    1580              1585              1590

Gly Phe Arg Pro Asn Pro Ile Thr Val Ile Leu Glu Asp Ile Asp
    1595              1600              1605

Glu Cys Gln Glu Leu Pro Gly Leu Cys Gln Gly Gly Lys Cys Ile
    1610              1615              1620

Asn Thr Phe Gly Ser Phe Gln Cys Arg Cys Pro Thr Gly Tyr Tyr
    1625              1630              1635

Leu Asn Glu Asp Thr Arg Val Cys Asp Asp Val Asn Glu Cys Glu
    1640              1645              1650

Thr Pro Gly Ile Cys Gly Pro Gly Thr Cys Tyr Asn Thr Val Gly
    1655              1660              1665

Asn Tyr Thr Cys Ile Cys Pro Pro Asp Tyr Met Gln Val Asn Gly
```

-continued

```
             1670              1675              1680

Gly Asn Asn Cys Met Asp Met Arg Arg Ser Ile Cys Tyr Arg Asn
    1685              1690              1695

Tyr Tyr Ala Asp Asn Gln Thr Cys Asp Gly Glu Leu Leu Phe Asn
    1700              1705              1710

Met Thr Lys Lys Met Cys Cys Cys Ser Tyr Asn Ile Arg Arg Ala
    1715              1720              1725

Trp Asn Lys Pro Cys Glu Gln Cys Pro Ile Pro Ser Thr Asp Glu
    1730              1735              1740

Phe Ala Thr Leu Cys Gly Ser Gln Arg Pro Gly Phe Val Ile Asp
    1745              1750              1755

Ile Tyr Thr Gly Leu Pro Val Asp Ile Asp Glu Cys Arg Glu Ile
    1760              1765              1770

Pro Gly Val Cys Glu Asn Gly Val Cys Ile Asn Met Val Gly Ser
    1775              1780              1785

Phe Arg Cys Glu Cys Pro Val Gly Phe Phe Tyr Asn Asp Lys Leu
    1790              1795              1800

Leu Val Cys Glu Asp Ile Asp Glu Cys Gln Asn Gly Pro Val Cys
    1805              1810              1815

Leu Arg Asn Ala Glu Cys Ile Asn Thr Ala Gly Ser Tyr Arg Cys
    1820              1825              1830

Asp Cys Lys Pro Gly Tyr Arg Leu Thr Ser Thr Gly Gln Cys Asn
    1835              1840              1845

Asp Arg Asn Glu Cys Gln Glu Ile Pro Asn Ile Cys Ser His Gly
    1850              1855              1860

Gln Cys Ile Asp Thr Val Gly Ser Phe Tyr Cys Leu Cys His Thr
    1865              1870              1875

Gly Phe Lys Thr Asn Glu Asp Gln Thr Met Cys Leu Asp Ile Asn
    1880              1885              1890

Glu Cys Glu Arg Asp Ala Cys Gly Asn Gly Thr Cys Arg Asn Thr
    1895              1900              1905

Ile Gly Ser Phe Asn Cys Arg Cys Asn His Gly Phe Ile Leu Ser
    1910              1915              1920

His Asn Asn Asp Cys Ile Asp Val Asp Glu Cys Ala Thr Gly Asn
    1925              1930              1935

Gly Asn Leu Cys Arg Asn Gly Gln Cys Val Asn Thr Val Gly Ser
    1940              1945              1950

Phe Gln Cys Arg Cys Asn Glu Gly Tyr Glu Val Ala Pro Asp Gly
    1955              1960              1965

Arg Thr Cys Val Asp Ile Asn Glu Cys Val Leu Asp Pro Gly Lys
    1970              1975              1980

Cys Ala Pro Gly Thr Cys Gln Asn Leu Asp Gly Ser Tyr Arg Cys
    1985              1990              1995

Ile Cys Pro Pro Gly Tyr Ser Leu Gln Asn Asp Lys Cys Glu Asp
    2000              2005              2010

Ile Asp Glu Cys Val Glu Glu Pro Glu Ile Cys Ala Leu Gly Thr
    2015              2020              2025

Cys Ser Asn Thr Glu Gly Ser Phe Lys Cys Leu Cys Pro Glu Gly
    2030              2035              2040

Phe Ser Trp Ser Ser Ser Gly Arg Arg Cys Gln Asp Leu Arg Met
    2045              2050              2055

Ser Tyr Cys Tyr Ala Lys Phe Glu Gly Gly Lys Cys Ser Ser Pro
    2060              2065              2070
```

-continued

```
Lys Ser Arg Asn His Ser Lys Gln Glu Cys Cys Cys Ala Leu Lys
2075                2080                2085

Gly Glu Gly Trp Gly Asp Pro Cys Glu Leu Cys Pro Thr Glu Pro
2090                2095                2100

Asp Glu Ala Phe Arg Gln Ile Cys Pro Phe Gly Ser Gly Ile Ile
2105                2110                2115

Val Gly Pro Asp Asp Ser Ala Val Asp Met Asp Glu Cys Lys Glu
2120                2125                2130

Pro Asp Val Cys Arg His Gly Gln Cys Ile Asn Thr Asp Gly Ser
2135                2140                2145

Tyr Arg Cys Glu Cys Pro Phe Gly Tyr Ile Leu Glu Gly Asn Glu
2150                2155                2160

Cys Val Asp Thr Asp Glu Cys Ser Val Gly Asn Pro Cys Gly Asn
2165                2170                2175

Gly Thr Cys Lys Asn Val Ile Gly Gly Phe Glu Cys Thr Cys Glu
2180                2185                2190

Glu Gly Phe Glu Pro Gly Pro Met Met Thr Cys Glu Asp Ile Asn
2195                2200                2205

Glu Cys Ala Gln Asn Pro Leu Leu Cys Ala Phe Arg Cys Val Asn
2210                2215                2220

Thr Tyr Gly Ser Tyr Glu Cys Lys Cys Pro Val Gly Tyr Val Leu
2225                2230                2235

Arg Glu Asp Arg Arg Met Cys Lys Asp Glu Asp Glu Cys Ala Glu
2240                2245                2250

Gly Lys His Asp Cys Thr Glu Lys Gln Met Glu Cys Lys Asn Leu
2255                2260                2265

Ile Gly Thr Tyr Met Cys Ile Cys Gly Pro Gly Tyr Gln Arg Arg
2270                2275                2280

Pro Asp Gly Glu Gly Cys Ile Asp Glu Asn Glu Cys Gln Thr Lys
2285                2290                2295

Pro Gly Ile Cys Glu Asn Gly Arg Cys Leu Asn Thr Leu Gly Ser
2300                2305                2310

Tyr Thr Cys Glu Cys Asn Asp Gly Phe Thr Ala Ser Pro Thr Gln
2315                2320                2325

Asp Glu Cys Leu Asp Asn Arg Glu Gly Tyr Cys Phe Ser Glu Val
2330                2335                2340

Phe Glu Asn Met Cys Gln Ile Gly Ser Ser Asn Arg Asn Pro Val
2345                2350                2355

Thr Lys Ser Glu Cys Cys Cys Val Gly Gly Arg Gly Trp Gly Leu
2360                2365                2370

His Cys Glu Ile Cys Pro Phe Glu Gly Thr Val Ala Tyr Lys Lys
2375                2380                2385

Leu Cys Pro His Gly Arg Gly Phe Met Thr Asn Gly Ala Asp Val
2390                2395                2400

Asp Glu Cys Lys Val Ile His Asp Val Cys Arg Asn Gly Glu Cys
2405                2410                2415

Val Asn Asp Arg Gly Ser Tyr His Cys Ile Cys Lys Thr Gly Tyr
2420                2425                2430

Thr Pro Asp Ile Thr Gly Thr Ser Cys Val Asp Leu Asn Glu Cys
2435                2440                2445

Asn Gln Ala Pro Lys Pro Cys Asn Phe Ile Cys Lys Asn Thr Glu
2450                2455                2460

Gly Ser Tyr Gln Cys Ser Cys Pro Asn Gly Tyr Ile Leu Gln Glu
2465                2470                2475
```

```
Asp Gly Arg Ser Cys Lys Asp Leu Asp Glu Cys Ala Thr Lys Gln
    2480            2485                2490

His Asn Cys Gln Phe Leu Cys Val Asn Thr Ile Gly Gly Phe Thr
    2495            2500                2505

Cys Lys Cys Pro Pro Gly Phe Thr Gln His His Thr Ala Cys Ile
    2510            2515                2520

Asp Asn Asn Glu Cys Thr Ser Asp Ile Asn Leu Cys Gly Ser Lys
    2525            2530                2535

Gly Ile Cys Gln Asn Thr Pro Gly Ser Phe Thr Cys Glu Cys Gln
    2540            2545                2550

Arg Gly Phe Ser Leu Asp Gln Ser Gly Ala Ser Cys Glu Asp Val
    2555            2560                2565

Asp Glu Cys Glu Gly Asn His Arg Cys Gln His Gly Cys Gln Asn
    2570            2575                2580

Ile Ile Gly Gly Tyr Arg Cys Ser Cys Pro Gln Gly Tyr Leu Gln
    2585            2590                2595

His Tyr Gln Trp Asn Gln Cys Val Asp Glu Asn Glu Cys Leu Ser
    2600            2605                2610

Ala His Val Cys Gly Gly Ala Ser Cys His Asn Thr Leu Gly Ser
    2615            2620                2625

Tyr Lys Cys Met Cys Pro Ala Gly Phe Gln Tyr Glu Gln Phe Ser
    2630            2635                2640

Gly Gly Cys Gln Asp Ile Asn Glu Cys Gly Ser Ser Gln Ala Pro
    2645            2650                2655

Cys Ser Tyr Gly Cys Ser Asn Thr Glu Gly Gly Tyr Leu Cys Gly
    2660            2665                2670

Cys Pro Pro Gly Tyr Phe Arg Ile Gly Gln Gly His Cys Leu Ser
    2675            2680                2685

Gly Met Gly Met Gly Arg Gly Ala Pro Glu Pro Ala Ser Ser
    2690            2695                2700

Glu Met Asp Asp Asn Ser Leu Ser Pro Glu Ala Cys Tyr Glu Cys
    2705            2710                2715

Lys Ile Asn Gly Tyr Pro Lys Arg Gly Arg Lys Arg Arg Ser Thr
    2720            2725                2730

Asn Glu Thr Asp Ala Ser Asp Ile Gln Asp Gly Ser Glu Met Glu
    2735            2740                2745

Ala Asn Val Ser Leu Ala Ser Trp Asp Val Glu Lys Pro Ala Ser
    2750            2755                2760

Phe Ala Phe Asn Ile Ser His Val Ser Asn Lys Val Arg Ile Leu
    2765            2770                2775

Glu Leu Leu Pro Ala Leu Thr Thr Leu Met Asn His Asn Arg Tyr
    2780            2785                2790

Leu Ile Glu Ser Gly Asn Glu Asp Gly Phe Phe Lys Ile Asn Gln
    2795            2800                2805

Lys Glu Gly Val Ser Tyr Leu His Phe Thr Lys Lys Asn Ala Val
    2810            2815                2820

Ala Gly Thr Tyr Ser Leu Gln Ile Ser Ser Thr Pro Leu Tyr Lys
    2825            2830                2835

Lys Lys Glu Leu Asn Gln Leu Glu Asp Arg Tyr Asp Lys Asp Tyr
    2840            2845                2850

Leu Ser Gly Glu Leu Gly Asp Asn Leu Lys Met Lys Ile Gln Ile
    2855            2860                2865

Leu Leu His
```

-continued

2870

<210> SEQ ID NO 23
<211> LENGTH: 395
<212> TYPE: PRT
<213> ORGANISM: Bos taurus

<400> SEQUENCE: 23

Met Ser Lys Arg Asp Ile Val Leu Thr Asn Val Thr Val Val Gln Leu
1               5                   10                  15

Leu Arg Gln Pro Cys Pro Glu Pro Arg Val Glu Ala Glu Pro Glu Pro
            20                  25                  30

Pro Ala Gln Pro Gln Pro Gln Pro Glu Pro Ile Lys Glu Glu Val Pro
        35                  40                  45

Pro Pro Pro Pro Pro Pro Ala Pro Lys Lys Val Arg Glu Leu Ile
    50                  55                  60

Val Gly Ile Asn Gly Phe Gly Arg Ile Gly Arg Leu Val Leu Arg Ala
65                  70                  75                  80

Cys Met Glu Lys Gly Val Lys Val Val Ala Val Asn Asp Pro Phe Ile
                85                  90                  95

Asp Leu Glu Tyr Met Val Tyr Met Phe Lys Tyr Asp Ser Thr His Gly
            100                 105                 110

Arg Tyr Lys Gly Asn Val Glu His Lys Lys Gly Gln Leu Val Val Asp
        115                 120                 125

Asn Asn Glu Ile Ser Val Phe Gln Cys Lys Gln Pro Lys Glu Ile Pro
    130                 135                 140

Trp Lys Ser Val Gly Ser Pro Phe Val Val Glu Ala Thr Gly Val Tyr
145                 150                 155                 160

Leu Ser Leu Glu Glu Thr Lys Ala His Ile Glu Ala Gly Ala Gln Arg
                165                 170                 175

Val Val Ile Cys Ala Pro Ser Pro Asp Ala Pro Met Phe Val Met Gly
            180                 185                 190

Val Asn Glu Lys Glu Tyr Asn Pro Ser Ser Met Lys Ile Val Ser Asn
        195                 200                 205

Ala Ser Cys Thr Thr Asn Cys Leu Ala Pro Leu Ala Lys Val Ile His
    210                 215                 220

Glu Arg Phe Gly Ile Leu Glu Gly Leu Met Thr Thr Val His Ser Tyr
225                 230                 235                 240

Thr Ala Thr Gln Lys Thr Val Asp Gly Pro Ser Lys Lys Ala Trp Arg
                245                 250                 255

Asp Gly Arg Gly Ala His Gln Asn Ile Ile Pro Ala Ser Thr Gly Ala
            260                 265                 270

Ala Lys Ala Val Gly Lys Val Ile Pro Asp Leu Lys Gly Lys Leu Thr
        275                 280                 285

Gly Met Ala Phe Arg Val Pro Thr Pro Asp Val Ser Val Val Asp Leu
    290                 295                 300

Thr Cys Arg Leu Ala Gln Pro Thr Pro Tyr Ser Ala Ile Lys Asp Ala
305                 310                 315                 320

Ile Lys Ala Ala Ala Lys Gly Pro Met Ala Gly Ile Leu Ala Tyr Thr
                325                 330                 335

Glu Asp Glu Val Val Ser Thr Asp Phe Leu Ser Asp Thr His Ser Ser
            340                 345                 350

Ile Phe Asp Ala Lys Ala Gly Ile Ala Leu Asn Asp Asn Phe Val Lys
        355                 360                 365

Leu Ile Ser Trp Tyr Asp Asn Glu Tyr Gly Tyr Ser Asn Arg Val Val

```
                        370                 375                 380
Asp Leu Val Arg Tyr Met Phe Ser Arg Asp Lys
385                 390                 395

<210> SEQ ID NO 24
<211> LENGTH: 312
<212> TYPE: PRT
<213> ORGANISM: Mesocricetus auratus

<400> SEQUENCE: 24

Arg Ile Gly Arg Leu Val Thr Arg Ala Ala Phe Thr Ser Gly Lys Val
1               5                   10                  15

Asp Ile Val Ala Ile Asn Asp Pro Phe Ile Asp Leu Asn Tyr Met Val
            20                  25                  30

Tyr Met Phe Gln Tyr Asp Ser Thr His Gly Lys Phe Lys Gly Thr Val
        35                  40                  45

Lys Ala Glu Asn Gly Lys Leu Val Ile Asn Gly Lys Ala Ile Thr Ile
    50                  55                  60

Phe Gln Glu Arg Asp Pro Thr Asn Ile Lys Trp Gly Asp Ala Gly Ala
65                  70                  75                  80

Glu Tyr Val Val Glu Ser Thr Gly Val Phe Thr Thr Met Glu Lys Ala
                85                  90                  95

Gly Ala His Leu Lys Gly Gly Ala Lys Arg Val Ile Ile Ser Ala Pro
            100                 105                 110

Ser Ala Asp Ala Pro Met Phe Val Met Gly Val Asn His Asp Lys Tyr
        115                 120                 125

Asp Asn Ser Leu Lys Ile Val Ser Asn Ala Ser Cys Thr Thr Thr Cys
    130                 135                 140

Leu Ala Pro Leu Ala Lys Val Ile His Asp Asn Phe Gly Ile Val Lys
145                 150                 155                 160

Gly Leu Met Thr Thr Val His Ala Ile Thr Ala Thr Gln Lys Thr Val
                165                 170                 175

Asp Gly Pro Ser Gly Lys Leu Trp Arg Asp Gly Arg Gly Ala Ala Gln
            180                 185                 190

Asn Ile Ile Pro Ala Ser Thr Gly Ala Ala Lys Ala Val Gly Lys Val
        195                 200                 205

Ile Pro Glu Leu Asn Gly Lys Leu Thr Gly Met Ala Phe Arg Val Pro
    210                 215                 220

Thr Pro Asn Val Ser Val Val Asp Leu Thr Cys Arg Leu Glu Lys Ala
225                 230                 235                 240

Ala Lys Tyr Glu Asp Ile Lys Lys Val Val Lys Gln Ala Ser Glu Gly
                245                 250                 255

Pro Leu Lys Gly Ile Leu Gly Tyr Thr Glu Asp Gln Val Val Ser Cys
            260                 265                 270

Asp Phe Lys Ser Asp Ser His Ser Ser Thr Phe Asp Ala Gly Ala Gly
        275                 280                 285

Ile Ala Leu Asn Asp Asn Phe Val Lys Leu Ile Ser Trp Tyr Asp Asn
    290                 295                 300

Glu Phe Gly Tyr Ser Asn Arg Val
305                 310

<210> SEQ ID NO 25
<211> LENGTH: 654
<212> TYPE: PRT
<213> ORGANISM: Rattus norvegicus

<400> SEQUENCE: 25
```

```
Met Lys Phe Thr Val Val Ala Ala Ala Leu Leu Leu Cys Ala Val
1               5                   10                  15

Arg Ala Glu Glu Asp Lys Lys Glu Asp Val Gly Thr Val Val Gly
                20                  25                  30

Ile Asp Leu Gly Thr Thr Tyr Ser Cys Val Gly Val Phe Lys Asn Gly
            35                  40                  45

Arg Val Glu Ile Ile Ala Asn Asp Gln Gly Asn Arg Ile Thr Pro Ser
        50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
                100                 105                 110

Lys Phe Leu Pro Phe Lys Val Val Glu Lys Lys Thr Lys Pro Tyr Ile
            115                 120                 125

Gln Val Asp Ile Gly Gly Gly Gln Thr Lys Thr Phe Ala Pro Glu Glu
        130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
                180                 185                 190

Leu Asn Val Met Arg Ile Ile Asn Glu Pro Thr Ala Ala Ala Ile Ala
            195                 200                 205

Tyr Gly Leu Asp Lys Arg Gly Glu Lys Asn Ile Leu Val Phe Asp
210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
                260                 265                 270

Lys Thr Gly Lys Asp Val Arg Lys Asp Asn Arg Ala Val Gln Lys Leu
            275                 280                 285

Arg Arg Glu Val Glu Lys Ala Lys Arg Ala Leu Ser Ser Gln His Gln
        290                 295                 300

Ala Arg Ile Glu Ile Glu Ser Phe Phe Glu Gly Glu Asp Phe Ser Glu
305                 310                 315                 320

Thr Leu Thr Arg Ala Lys Phe Glu Glu Leu Asn Met Asp Leu Phe Arg
                325                 330                 335

Ser Thr Met Lys Pro Val Gln Lys Val Leu Glu Asp Ser Asp Leu Lys
                340                 345                 350

Lys Ser Asp Ile Asp Glu Ile Val Leu Val Gly Gly Ser Thr Arg Ile
            355                 360                 365

Pro Lys Ile Gln Gln Leu Val Lys Glu Phe Phe Asn Gly Lys Glu Pro
        370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
```

```
                420                 425                 430
Met Thr Lys Leu Ile Pro Arg Asn Thr Val Pro Thr Lys Lys Ser
            435                 440                 445
Gln Ile Phe Ser Thr Ala Ser Asp Asn Gln Pro Thr Val Thr Ile Lys
            450                 455                 460
Val Tyr Glu Gly Glu Arg Pro Leu Thr Lys Asp Asn His Leu Leu Gly
465                 470                 475                 480
Thr Phe Asp Leu Thr Gly Ile Pro Ala Pro Arg Gly Val Pro Gln
                485                 490                 495
Ile Glu Val Thr Phe Glu Ile Asp Val Asn Gly Ile Leu Arg Val Thr
                500                 505                 510
Ala Glu Asp Lys Gly Thr Gly Asn Lys Asn Lys Ile Thr Ile Thr Asn
            515                 520                 525
Asp Gln Asn Arg Leu Thr Pro Glu Glu Ile Glu Arg Met Val Asn Asp
            530                 535                 540
Ala Glu Lys Phe Ala Glu Glu Asp Lys Lys Leu Lys Glu Arg Ile Asp
545                 550                 555                 560
Thr Arg Asn Glu Leu Glu Ser Tyr Ala Tyr Ser Leu Lys Asn Gln Ile
                565                 570                 575
Gly Asp Lys Glu Lys Leu Gly Gly Lys Leu Ser Pro Glu Asp Lys Glu
            580                 585                 590
Thr Met Glu Lys Ala Val Glu Glu Lys Ile Glu Trp Leu Glu Ser His
            595                 600                 605
Gln Asp Ala Asp Ile Glu Asp Phe Lys Ala Lys Lys Lys Glu Leu Glu
            610                 615                 620
Glu Ile Val Gln Pro Ile Ile Ser Lys Leu Tyr Gly Ser Gly Gly Pro
625                 630                 635                 640
Pro Pro Thr Gly Glu Glu Asp Thr Ser Glu Lys Asp Glu Leu
                645                 650

<210> SEQ ID NO 26
<211> LENGTH: 328
<212> TYPE: PRT
<213> ORGANISM: Homo sapiens

<400> SEQUENCE: 26

Met Leu Pro Arg Val Gly Cys Pro Ala Leu Pro Leu Pro Pro Pro
1               5                   10                  15

Leu Leu Pro Leu Leu Pro Leu Leu Leu Leu Leu Gly Ala Ser Gly
            20                  25                  30

Gly Gly Gly Gly Ala Arg Ala Glu Val Leu Phe Arg Cys Pro Pro Cys
            35                  40                  45

Thr Pro Glu Arg Leu Ala Ala Cys Gly Pro Pro Val Ala Pro Pro
        50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
            100                 105                 110

Arg Cys Tyr Pro His Pro Gly Ser Glu Leu Pro Leu Gln Ala Leu Val
            115                 120                 125

Met Gly Glu Gly Thr Cys Glu Lys Arg Arg Asp Ala Glu Tyr Gly Ala
            130                 135                 140

Ser Pro Glu Gln Val Ala Asp Asn Gly Asp Asp His Ser Glu Gly Gly
```

```
                145                 150                 155                 160
Leu Val Glu Asn His Val Asp Ser Thr Met Asn Met Leu Gly Gly Gly
                    165                 170                 175

Gly Ser Ala Gly Arg Lys Pro Leu Lys Ser Gly Met Lys Glu Leu Ala
                180                 185                 190

Val Phe Arg Glu Lys Val Thr Glu Gln His Arg Gln Met Gly Lys Gly
            195                 200                 205

Gly Lys His His Leu Gly Leu Glu Glu Pro Lys Leu Arg Pro Pro
        210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
                260                 265                 270

Lys Gln Cys Lys Met Ser Leu Asn Gly Gln Arg Gly Glu Cys Trp Cys
                275                 280                 285

Val Asn Pro Asn Thr Gly Lys Leu Ile Gln Gly Ala Pro Thr Ile Arg
            290                 295                 300

Gly Asp Pro Glu Cys His Leu Phe Tyr Asn Glu Gln Gln Glu Ala Arg
305                 310                 315                 320

Gly Val His Thr Gln Arg Met Gln
                325

<210> SEQ ID NO 27
<211> LENGTH: 566
<212> TYPE: PRT
<213> ORGANISM: Rattus norvegicus

<400> SEQUENCE: 27

Met Ile Gly Lys Trp Arg Met Gly Leu Trp Ala Leu Ala Ile Leu Thr
1               5                   10                  15

Val Pro Met Tyr Phe Ile Val Thr Glu Gly Arg Lys Thr Ser Trp Gly
                20                  25                  30

Leu Glu Asn Glu Ala Leu Ile Val Arg Cys Pro Gln Arg Gly Gly Ala
            35                  40                  45

Ile Asn Pro Val Glu Trp Tyr Tyr Ser Asn Thr Asn Glu Arg Ile Pro
        50                  55                  60

Thr Gln Lys Arg Asn Arg Ile Phe Val Ser Arg Asp Arg Leu Lys Phe
65                  70                  75                  80

Leu Pro Ala Lys Val Glu Asp Ser Gly Ile Tyr Thr Cys Val Ile Arg
                85                  90                  95

Ser Pro Glu Ser Ile Lys Thr Gly Ser Leu Asn Val Thr Ile Tyr Lys
                100                 105                 110

Arg Pro Pro Asn Cys Lys Ile Pro Asp Tyr Met Met Tyr Ser Thr Val
            115                 120                 125

Asp Gly Ser Asp Lys Asn Ser Lys Ile Thr Cys Pro Thr Ile Ala Leu
        130                 135                 140

Tyr Asn Trp Thr Ala Pro Val Gln Trp Phe Lys Asn Cys Lys Ala Leu
145                 150                 155                 160

Gln Gly Pro Arg Phe Arg Ala His Met Ser Tyr Leu Phe Ile Asp Lys
                165                 170                 175

Val Ser His Val Asp Glu Gly Asp Tyr Thr Cys Arg Phe Thr His Thr
            180                 185                 190

Glu Asn Gly Thr Asn Tyr Ile Val Thr Ala Thr Arg Ser Phe Thr Val
```

```
                     195                 200                 205
Glu Glu Lys Gly Phe Ser Thr Phe Pro Val Ile Thr Asn Pro Pro His
210                 215                 220

Asn Tyr Thr Val Glu Val Glu Ile Gly Lys Thr Ala Asn Ile Ala Cys
225                 230                 235                 240

Ser Ala Cys Phe Gly Thr Ala Ser Gln Phe Ala Val Leu Trp Gln
                    245                 250                 255

Ile Asn Lys Thr Arg Ile Gly Ser Phe Gly Lys Ala Arg Ile Gln Glu
                260                 265                 270

Glu Lys Gly Pro Asn Lys Ser Ser Ser Asn Gly Met Ile Cys Leu Thr
                275                 280                 285

Ser Leu Leu Arg Ile Thr Gly Val Thr Asp Lys Asp Phe Ser Leu Lys
                290                 295                 300

Tyr Asp Cys Val Ala Met Asn His His Gly Val Ile Arg His Pro Val
305                 310                 315                 320

Arg Leu Arg Arg Lys Gln Pro Ile Asp His Gln Ser Thr Tyr Tyr Ile
                325                 330                 335

Val Ala Gly Cys Ser Leu Leu Leu Met Phe Ile Asn Val Leu Val Ile
                340                 345                 350

Val Leu Lys Val Phe Trp Ile Glu Val Ala Leu Phe Trp Arg Asp Ile
                355                 360                 365

Met Ala Pro Tyr Lys Thr Gln Asn Asp Gly Lys Leu Tyr Asp Ala Tyr
                370                 375                 380

Ile Ile Tyr Pro Arg Val Phe Arg Gly Ser Ala Ala Gly Thr Gly Ser
385                 390                 395                 400

Val Glu Tyr Phe Val His Tyr Thr Leu Pro Asp Val Leu Glu Asn Lys
                405                 410                 415

Cys Gly Tyr Lys Leu Cys Ile Tyr Gly Arg Asp Leu Leu Pro Gly Gln
                420                 425                 430

Asp Ala Ala Thr Val Val Glu Ser Ser Ile Gln Asn Ser Arg Arg Gln
                435                 440                 445

Val Phe Val Leu Ala Pro His Met Met His Ser Lys Glu Phe Ala Tyr
450                 455                 460

Glu Gln Glu Ile Ala Leu His Ser Ala Leu Ile Gln Asn Asn Ser Lys
465                 470                 475                 480

Val Ile Leu Ile Glu Met Glu Pro Met Gly Glu Ala Ser Arg Leu Gln
                485                 490                 495

Leu Gly Asp Leu Gln Asp Ser Leu Gln His Leu Val Lys Met Gln Gly
                500                 505                 510

Thr Ile Lys Trp Arg Glu Asp His Val Ala Asp Lys Gln Ser Leu Ser
                515                 520                 525

Ser Lys Phe Trp Lys His Val Arg Tyr Gln Met Pro Val Pro Lys Arg
                530                 535                 540

Pro Pro Lys Met Ala Ser Val Ala Pro Leu Ser Gly Lys Val Cys
545                 550                 555                 560

Leu Asp Leu Lys His Phe
                565

<210> SEQ ID NO 28
<211> LENGTH: 452
<212> TYPE: PRT
<213> ORGANISM: Bos taurus

<400> SEQUENCE: 28

Met Ala Gly Tyr Leu Arg Val Val Arg Ser Leu Cys Arg Ala Ser Gly
```

-continued

```
1               5                   10                  15
Ser Gly Ser Ala Trp Ala Pro Ala Ala Leu Thr Ala Pro Asn Leu Gln
            20                  25                  30

Glu Gln Pro Arg Arg His Tyr Ala Asp Lys Arg Ile Lys Val Ala Lys
            35                  40                  45

Pro Val Val Glu Met Asp Gly Asp Glu Met Thr Arg Ile Ile Trp Gln
50                  55                  60

Phe Ile Lys Glu Lys Leu Ile Leu Pro His Val Asp Val Gln Leu Lys
65                  70                  75                  80

Tyr Phe Asp Leu Gly Leu Pro Asn Arg Asp Gln Thr Asn Asp Gln Val
                85                  90                  95

Thr Ile Asp Ser Ala Leu Ala Thr Gln Lys Tyr Ser Val Ala Val Lys
            100                 105                 110

Cys Ala Thr Ile Thr Pro Asp Glu Ala Arg Val Glu Glu Phe Lys Leu
            115                 120                 125

Lys Lys Met Trp Lys Ser Pro Asn Gly Thr Ile Arg Asn Ile Leu Gly
            130                 135                 140

Gly Thr Val Phe Arg Glu Pro Ile Ile Cys Lys Asn Ile Pro Arg Leu
145                 150                 155                 160

Val Pro Gly Trp Thr Lys Pro Ile Thr Ile Gly Arg His Ala His Gly
                165                 170                 175

Asp Gln Tyr Lys Ala Thr Asp Phe Val Val Asp Arg Ala Gly Thr Phe
            180                 185                 190

Lys Val Val Phe Thr Pro Lys Asp Gly Ser Gly Pro Lys Glu Trp Glu
            195                 200                 205

Val Tyr Asn Phe Pro Ala Gly Gly Val Gly Met Gly Met Tyr Asn Thr
210                 215                 220

Asp Glu Ser Ile Ser Gly Phe Ala His Ser Cys Phe Gln Tyr Ala Ile
225                 230                 235                 240

Gln Lys Lys Trp Pro Leu Tyr Met Ser Thr Lys Asn Thr Ile Leu Lys
            245                 250                 255

Ala Tyr Asp Gly Arg Phe Lys Asp Ile Phe Gln Ala Ile Phe Glu Lys
            260                 265                 270

His Tyr Lys Thr Glu Phe Asp Lys His Lys Ile Trp Tyr Glu His Arg
            275                 280                 285

Leu Ile Asp Asp Met Val Ala Gln Val Leu Lys Ser Ser Gly Gly Phe
            290                 295                 300

Val Trp Ala Cys Lys Asn Tyr Asp Gly Asp Val Gln Ser Asp Ile Leu
305                 310                 315                 320

Ala Gln Gly Phe Gly Ser Leu Gly Leu Met Thr Ser Val Leu Val Cys
                325                 330                 335

Pro Asp Gly Lys Thr Ile Glu Ala Glu Ala Ala His Gly Thr Val Thr
            340                 345                 350

Arg His Tyr Arg Glu His Gln Lys Gly Arg Pro Thr Ser Thr Asn Pro
            355                 360                 365

Ile Ala Ser Ile Phe Ala Trp Thr Arg Gly Leu Glu His Arg Gly Lys
            370                 375                 380

Leu Asp Gly Asn Gln Asp Leu Ile Arg Phe Ala Gln Thr Leu Glu Lys
385                 390                 395                 400

Val Cys Val Glu Thr Val Glu Ser Gly Ala Met Thr Lys Asp Leu Ala
                405                 410                 415

Gly Cys Ile His Gly Leu Ser Asn Val Lys Leu Asn Glu His Phe Leu
            420                 425                 430
```

```
Asn Thr Ser Asp Phe Leu Asp Thr Ile Lys Ser Asn Leu Asp Arg Ala
        435                 440                 445

Leu Gly Gln Gln
    450
```

<210> SEQ ID NO 29
<211> LENGTH: 338
<212> TYPE: PRT
<213> ORGANISM: Rattus norvegicus

<400> SEQUENCE: 29

```
Met Leu Ser Ala Leu Ala Arg Pro Val Gly Ala Ala Leu Arg Arg Ser
1               5                   10                  15

Phe Ser Thr Ser Ala Gln Asn Asn Ala Lys Val Ala Val Leu Gly Ala
                20                  25                  30

Ser Gly Gly Ile Gly Gln Pro Leu Ser Leu Leu Leu Lys Asn Ser Pro
            35                  40                  45

Leu Val Ser Arg Leu Thr Leu Tyr Asp Ile Ala His Thr Pro Gly Val
    50                  55                  60

Ala Ala Asp Leu Ser His Ile Glu Thr Arg Ala Asn Val Lys Gly Tyr
65                  70                  75                  80

Leu Gly Pro Glu Gln Leu Pro Asp Cys Leu Lys Gly Cys Asp Val Val
                85                  90                  95

Val Ile Pro Ala Gly Val Pro Arg Lys Pro Gly Met Thr Arg Asp Asp
            100                 105                 110

Leu Phe Asn Thr Asn Ala Thr Ile Val Ala Thr Leu Thr Ala Ala Cys
    115                 120                 125

Ala Gln His Cys Pro Glu Ala Met Ile Cys Ile Ile Ser Asn Pro Val
130                 135                 140

Asn Ser Thr Ile Pro Ile Thr Ala Glu Val Phe Lys Lys His Gly Val
145                 150                 155                 160

Tyr Asn Pro Asn Lys Ile Phe Gly Val Thr Thr Leu Asp Ile Val Arg
                165                 170                 175

Ala Asn Thr Phe Val Ala Glu Leu Lys Gly Leu Asp Pro Ala Arg Val
            180                 185                 190

Asn Val Pro Val Ile Gly Gly His Ala Gly Lys Thr Ile Ile Pro Leu
    195                 200                 205

Ile Ser Gln Cys Thr Pro Lys Val Asp Phe Pro Gln Asp Gln Leu Ala
210                 215                 220

Thr Leu Thr Gly Arg Ile Gln Glu Ala Gly Thr Glu Val Val Lys Ala
225                 230                 235                 240

Lys Ala Gly Ala Gly Ser Ala Thr Leu Ser Met Ala Tyr Ala Gly Ala
                245                 250                 255

Arg Phe Val Phe Ser Leu Val Asp Ala Met Asn Gly Lys Glu Gly Val
            260                 265                 270

Ile Glu Cys Ser Phe Val Gln Ser Lys Glu Thr Glu Cys Thr Tyr Phe
    275                 280                 285

Ser Thr Pro Leu Leu Leu Gly Lys Lys Gly Leu Glu Lys Asn Leu Gly
290                 295                 300

Ile Gly Lys Ile Thr Pro Phe Glu Glu Lys Met Ile Ala Glu Ala Ile
305                 310                 315                 320

Pro Glu Leu Lys Ala Ser Ile Lys Lys Gly Glu Asp Phe Val Lys Asn
                325                 330                 335

Met Lys
```

```
<210> SEQ ID NO 30
<211> LENGTH: 662
<212> TYPE: PRT
<213> ORGANISM: Rattus norvegicus

<400> SEQUENCE: 30

Met Glu Ala Arg Leu Val Trp Gly Val Leu Val Gly Pro Leu Arg Val
1               5                   10                  15

Leu Cys Val Leu Cys Cys Leu Leu Gly His Ala Ile Ala Ala Pro Ser
            20                  25                  30

Pro Ile Ile Lys Phe Pro Gly Asp Val Ser Pro Lys Thr Asp Lys Glu
        35                  40                  45

Leu Ala Val Gln Tyr Leu Asn Thr Phe Tyr Gly Cys Pro Lys Glu Ser
    50                  55                  60

Cys Asn Leu Phe Val Leu Lys Asp Thr Leu Lys Lys Met Gln Lys Phe
65                  70                  75                  80

Phe Gly Leu Pro Gln Thr Gly Asp Leu Asp Gln Asn Thr Ile Glu Thr
                85                  90                  95

Met Arg Lys Pro Arg Cys Gly Asn Pro Asp Val Ala Asn Tyr Asn Phe
            100                 105                 110

Phe Pro Arg Lys Pro Lys Trp Asp Lys Asn Gln Ile Thr Tyr Arg Ile
        115                 120                 125

Ile Gly Tyr Thr Pro Asp Leu Asp Pro Glu Thr Val Asp Asp Ala Phe
    130                 135                 140

Ala Arg Ala Leu Lys Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
            180                 185                 190

His Ala Phe Ala Pro Gly Thr Gly Val Gly Gly Asp Ser His Phe Asp
        195                 200                 205

Asp Asp Glu Leu Trp Thr Leu Gly Glu Gly Gln Val Val Arg Val Lys
    210                 215                 220

Tyr Gly Asn Ala Asp Gly Glu Tyr Cys Lys Phe Pro Phe Leu Phe Asn
225                 230                 235                 240

Gly Arg Glu Tyr Ser Ser Cys Thr Asp Thr Gly Arg Ser Asp Gly Phe
                245                 250                 255

Leu Trp Cys Ser Thr Thr Tyr Asn Phe Glu Lys Asp Gly Lys Tyr Gly
            260                 265                 270

Phe Cys Pro His Glu Ala Leu Phe Thr Met Gly Gly Asn Gly Asp Gly
        275                 280                 285

Gln Pro Cys Lys Phe Pro Phe Arg Phe Gln Gly Thr Ser Tyr Asn Ser
    290                 295                 300

Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
                325                 330                 335

Met Ser Thr Val Gly Gly Asn Ser Glu Gly Ala Pro Cys Val Phe Pro
            340                 345                 350

Phe Thr Phe Leu Gly Asn Lys Tyr Glu Ser Cys Thr Ser Ala Gly Arg
        355                 360                 365

Ser Asp Gly Lys Val Trp Cys Ala Thr Thr Thr Asn Tyr Asp Asp Asp
    370                 375                 380

Arg Lys Trp Gly Phe Cys Pro Asp Gln Gly Tyr Ser Leu Phe Leu Val
```

```
            385                 390                 395                 400
Ala Ala His Glu Phe Gly His Ala Met Gly Leu Glu His Ser Gln Asp
                    405                 410                 415

Pro Gly Ala Leu Met Ala Pro Ile Tyr Thr Tyr Thr Lys Asn Phe Arg
            420                 425                 430

Leu Ser Asn Asp Asp Ile Lys Gly Ile Gln Glu Leu Tyr Gly Pro Ser
                435                 440                 445

Pro Asp Ala Asp Thr Asp Thr Gly Thr Gly Pro Thr Pro Thr Leu Gly
        450                 455                 460

Pro Val Thr Pro Glu Ile Cys Lys Gln Asp Ile Val Phe Asp Gly Ile
465                 470                 475                 480

Ala Gln Ile Arg Gly Glu Ile Phe Phe Phe Lys Asp Arg Phe Ile Trp
                485                 490                 495

Arg Thr Val Thr Pro Arg Asp Lys Pro Thr Gly Pro Leu Leu Val Ala
                500                 505                 510

Thr Phe Trp Pro Glu Leu Pro Glu Lys Ile Asp Ala Val Tyr Glu Ala
            515                 520                 525

Pro Gln Glu Glu Lys Ala Val Phe Phe Ala Gly Asn Glu Tyr Trp Val
        530                 535                 540

Tyr Ser Ala Ser Thr Leu Glu Arg Gly Tyr Pro Lys Pro Leu Thr Ser
545                 550                 555                 560

Leu Gly Leu Pro Pro Asp Val Gln Gln Val Asp Ala Ala Phe Asn Trp
                565                 570                 575

Ser Lys Asn Lys Lys Thr Tyr Ile Phe Ser Gly Asp Lys Phe Trp Arg
                580                 585                 590

Tyr Asn Glu Val Lys Lys Lys Met Asp Pro Gly Phe Pro Lys Leu Ile
            595                 600                 605

Ala Asp Ser Trp Asn Ala Ile Pro Asp Asn Leu Asp Ala Val Val Asp
        610                 615                 620

Leu Gln Gly Gly Gly His Ser Tyr Phe Lys Gly Ala Tyr Tyr Leu
625                 630                 635                 640

Lys Leu Glu Asn Gln Ser Leu Lys Ser Val Lys Phe Gly Ser Ile Lys
                645                 650                 655

Ser Asp Trp Leu Gly Cys
            660

<210> SEQ ID NO 31
<211> LENGTH: 217
<212> TYPE: PRT
<213> ORGANISM: Rattus norvegicus

<400> SEQUENCE: 31

Met Ala Pro Phe Ala Ser Leu Ala Ser Gly Ile Leu Leu Leu Leu Ser
1               5                   10                  15

Leu Ile Ala Ser Ser Lys Ala Cys Ser Cys Ala Pro Thr His Pro Gln
            20                  25                  30

Thr Ala Phe Cys Asn Ser Asp Leu Val Ile Arg Ala Lys Phe Met Gly
        35                  40                  45

Ser Pro Glu Ile Ile Glu Thr Thr Leu Tyr Gln Arg Tyr Glu Ile Lys
    50                  55                  60

Met Thr Lys Met Leu Lys Gly Phe Asp Ala Val Gly Asn Ala Thr Gly
65                  70                  75                  80

Phe Arg Phe Ala Tyr Thr Pro Ala Met Glu Ser Leu Cys Gly Tyr Val
                85                  90                  95

His Lys Ser Gln Asn Arg Ser Glu Glu Phe Leu Ile Ala Gly Arg Leu
```

```
                       100                 105                 110
Arg Asn Gly Asn Leu His Ile Thr Ala Cys Ser Phe Leu Val Pro Trp
            115                 120                 125

His Asn Leu Ser Pro Ala Gln Gln Lys Ala Phe Val Lys Thr Tyr Ser
            130                 135                 140

Ala Gly Cys Gly Val Cys Thr Val Phe Pro Cys Ser Ala Ile Pro Cys
145                 150                 155                 160

Lys Leu Glu Ser Asp Ser His Cys Leu Trp Thr Asp Gln Ile Leu Met
            165                 170                 175

Gly Ser Glu Lys Gly Tyr Gln Ser Asp His Phe Ala Cys Leu Pro Arg
            180                 185                 190

Asn Pro Asp Leu Cys Thr Trp Gln Tyr Leu Gly Val Ser Met Thr Arg
            195                 200                 205

Ser Leu Pro Leu Ala Lys Ala Glu Ala
            210                 215
```

<210> SEQ ID NO 32
<211> LENGTH: 220
<212> TYPE: PRT
<213> ORGANISM: Bos taurus

<400> SEQUENCE: 32

```
Met Gly Ala Ala Ala Arg Ser Leu Pro Leu Ala Phe Cys Leu Leu
1               5                   10                  15

Leu Gly Thr Leu Leu Pro Arg Ala Asp Ala Cys Ser Cys Ser Pro Val
            20                  25                  30

His Pro Gln Gln Ala Phe Cys Asn Ala Asp Ile Val Ile Arg Ala Lys
            35                  40                  45

Ala Val Asn Lys Lys Glu Val Asp Ser Gly Asn Asp Ile Tyr Gly Asn
50                  55                  60

Pro Ile Lys Arg Ile Gln Tyr Glu Ile Lys Gln Ile Lys Met Phe Lys
65                  70                  75                  80

Gly Pro Asp Gln Asp Ile Glu Phe Ile Tyr Thr Ala Pro Ala Ala Ala
            85                  90                  95

Val Cys Gly Val Ser Leu Asp Ile Gly Gly Lys Lys Glu Tyr Leu Ile
            100                 105                 110

Ala Gly Lys Ala Glu Gly Asn Gly Asn Met His Ile Thr Leu Cys Asp
            115                 120                 125

Phe Ile Val Pro Trp Asp Thr Leu Ser Ala Thr Gln Lys Lys Ser Leu
            130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Cys Leu Trp Met Asp
            165                 170                 175

Trp Val Thr Glu Lys Asn Ile Asn Gly His Gln Ala Lys Phe Phe Ala
            180                 185                 190

Cys Ile Lys Arg Ser Asp Gly Ser Cys Ala Trp Tyr Arg Gly Ala Ala
            195                 200                 205

Pro Pro Lys Gln Glu Phe Leu Asp Ile Glu Asp Pro
            210                 215                 220
```

<210> SEQ ID NO 33
<211> LENGTH: 299
<212> TYPE: PRT
<213> ORGANISM: Bos taurus

<400> SEQUENCE: 33

```
Met Lys Thr Leu Gln Ser Thr Leu Leu Phe Leu Phe Val Pro Leu
1               5                   10                  15

Ile Lys Pro Ala Pro Ser Gln Gln Asp Ser Arg Ile Ile Tyr Asp
                20                  25                  30

Tyr Gly Thr Asp Asn Leu Glu Glu Thr Phe Phe Ser Gln Asp Tyr Glu
            35                  40                  45

Asp Lys Tyr Leu Asp Gly Lys Ser Thr Lys Glu Lys Glu Thr Met Ile
        50                  55                  60

Ile Val Pro Asp Glu Lys Ser Phe Gln Leu Gln Lys Asp Glu Asn Ile
65                  70                  75                  80

Thr Pro Leu Pro Pro Lys Lys Glu Asn Asp Glu Met Pro Thr Cys Leu
                85                  90                  95

Leu Cys Val Cys Leu Ser Gly Ser Val Tyr Cys Glu Glu Val Asp Ile
            100                 105                 110

Asp Ala Val Pro Pro Leu Pro Lys Glu Ser Ala Tyr Leu Tyr Ala Arg
        115                 120                 125

Phe Asn Lys Ile Lys Lys Leu Thr Ala Lys Asp Phe Ala Asp Ile Pro
    130                 135                 140

Asn Leu Arg Arg Leu Asp Phe Thr Gly Asn Leu Ile Glu Asp Ile Glu
145                 150                 155                 160

Asp Gly Thr Phe Ser Lys Leu Ser Leu Leu Glu Glu Leu Thr Leu Ala
            165                 170                 175

Glu Asn Gln Leu Leu Lys Leu Pro Val Leu Pro Pro Lys Leu Thr Leu
        180                 185                 190

Phe Asn Ala Lys Tyr Asn Lys Ile Lys Ser Arg Gly Ile Lys Ala Asn
    195                 200                 205

Thr Phe Lys Lys Leu His Asn Leu Ser Phe Leu Tyr Leu Asp His Asn
        210                 215                 220

Ala Leu Glu Ser Val Pro Leu Asn Leu Pro Glu Ser Leu Arg Val Ile
225                 230                 235                 240

His Leu Gln Phe Asn Asn Ile Thr Ser Ile Thr Asp Asp Thr Phe Cys
            245                 250                 255

Lys Ala Asn Asp Thr Ser Tyr Ile Arg Asp Arg Ile Glu Glu Ile Arg
        260                 265                 270

Leu Glu Gly Asn Pro Val Ile Leu Gly Lys His Pro Asn Ser Phe Ile
    275                 280                 285

Cys Leu Lys Arg Leu Pro Ile Gly Ser Tyr Ile
    290                 295
```

<210> SEQ ID NO 34
<211> LENGTH: 780
<212> TYPE: PRT
<213> ORGANISM: Rattus norvegicus

<400> SEQUENCE: 34

```
Met Ala Pro Tyr Ser Leu Leu Val Thr Arg Leu Gln Lys Ala Leu Gly
1               5                   10                  15

Val Arg Gln Tyr His Val Ala Ser Ala Leu Cys Gln Arg Ala Lys Val
                20                  25                  30

Ala Met Ser His Phe Glu Pro Ser Glu Tyr Ile Arg Tyr Asp Leu Leu
            35                  40                  45

Glu Lys Asn Ile Asn Ile Val Arg Lys Arg Leu Asn Arg Pro Leu Thr
        50                  55                  60

Leu Ser Glu Lys Ile Val Tyr Gly His Leu Asp Asp Pro Ala Asn Gln
65                  70                  75                  80
```

```
Glu Ile Glu Arg Gly Lys Thr Tyr Leu Arg Leu Arg Pro Asp Arg Val
                85                  90                  95

Ala Met Gln Asp Ala Thr Ala Gln Met Ala Met Leu Gln Phe Ile Ser
            100                 105                 110

Ser Gly Leu Pro Lys Val Ala Val Pro Ser Thr Ile His Cys Asp His
            115                 120                 125

Leu Ile Glu Ala Gln Leu Gly Gly Glu Lys Asp Leu Arg Arg Ala Lys
130                 135                 140

Asp Ile Asn Gln Glu Val Tyr Asn Phe Leu Ala Thr Ala Gly Ala Lys
145                 150                 155                 160

Tyr Gly Val Gly Phe Trp Arg Pro Gly Ser Gly Ile Ile His Gln Ile
                165                 170                 175

Ile Leu Glu Asn Tyr Ala Tyr Pro Gly Val Leu Leu Ile Gly Thr Asp
            180                 185                 190

Ser His Thr Pro Asn Gly Gly Leu Gly Gly Ile Cys Ile Gly Val
            195                 200                 205

Gly Gly Ala Asp Ala Val Asp Val Met Ala Gly Ile Pro Trp Glu Pro
210                 215                 220

Lys Cys Pro Lys Val Ile Gly Val Lys Leu Thr Gly Thr Leu Ser Gly
225                 230                 235                 240

Trp Thr Ser Pro Lys Asp Val Ile Leu Lys Val Ala Gly Ile Leu Thr
                245                 250                 255

Val Lys Gly Gly Thr Gly Ala Ile Val Glu Tyr His Gly Pro Gly Val
            260                 265                 270

Asp Ser Ile Ser Cys Thr Gly Met Ala Thr Ile Cys Asn Met Gly Ala
            275                 280                 285

Glu Ile Gly Ala Thr Thr Pro Val Phe Pro Tyr Asn His Arg Met Lys
290                 295                 300

Lys Tyr Leu Ser Lys Thr Gly Arg Ala Asp Ile Ala Asn Leu Ala Glu
305                 310                 315                 320

Glu Phe Lys Asp His Leu Val Pro Asp Pro Gly Cys Gln Tyr Asp Gln
                325                 330                 335

Val Ile Glu Ile Asn Leu Asn Glu Leu Lys Pro His Ile Asn Gly Pro
            340                 345                 350

Phe Thr Pro Asp Leu Ala His Pro Val Ala Asp Val Gly Thr Val Ala
            355                 360                 365

Glu Lys Glu Gly Trp Pro Leu Asp Ile Arg Val Gly Leu Ile Gly Ser
370                 375                 380

Cys Thr Asn Ser Ser Tyr Glu Asp Met Gly Arg Ser Ala Ala Val Ala
385                 390                 395                 400

Lys Gln Ala Leu Ala His Gly Leu Lys Cys Lys Ser Gln Phe Thr Ile
                405                 410                 415

Thr Pro Gly Ser Glu Gln Ile Arg Ala Thr Ile Glu Arg Asp Gly Tyr
            420                 425                 430

Ala Gln Ile Leu Arg Asp Val Gly Gly Ile Val Leu Ala Asn Ala Cys
            435                 440                 445

Gly Pro Cys Ile Gly Gln Trp Asp Arg Lys Asp Ile Lys Lys Gly Glu
            450                 455                 460

Lys Asn Thr Ile Val Thr Ser Tyr Asn Arg Asn Phe Thr Gly Arg Asn
465                 470                 475                 480

Asp Ala Asn Pro Glu Thr His Ala Phe Val Thr Ser Pro Glu Ile Val
                485                 490                 495

Thr Ala Leu Ala Ile Ala Gly Thr Leu Lys Phe Asn Pro Glu Thr Asp
```

```
                 500                 505                 510
Phe Leu Thr Gly Lys Asp Gly Lys Phe Lys Leu Glu Ala Pro Asp
            515                 520                 525

Ala Asp Glu Leu Pro Arg Ser Asp Phe Asp Pro Gly Gln Asp Thr Tyr
            530                 535                 540

Gln His Pro Pro Lys Asp Ser Ser Gly Gln Arg Val Asp Val Ser Pro
545                 550                 555                 560

Thr Ser Gln Arg Leu Gln Leu Leu Glu Pro Phe Asp Lys Trp Asp Gly
                565                 570                 575

Lys Asp Leu Glu Asp Gln Gln Ile Leu Ile Lys Val Lys Gly Lys Cys
            580                 585                 590

Thr Thr Asp His Ile Ser Ala Ala Gly Pro Trp Leu Lys Phe Arg Gly
            595                 600                 605

His Leu Asp Asn Ile Ser Asn Asn Leu Leu Ile Gly Ala Ile Asn Ile
            610                 615                 620

Glu Asn Gly Lys Ala Asn Ser Val Arg Asn Ala Val Thr Gln Glu Phe
625                 630                 635                 640

Gly Pro Val Pro Asp Thr Ala Arg Tyr Tyr Lys Lys His Gly Ile Arg
                645                 650                 655

Trp Val Met Ile Gly Asp Glu Asn Tyr Gly Gly Ser Ser Arg Glu
                660                 665                 670

His Ala Ala Leu Glu Pro Arg His Leu Gly Gly Arg Ala Ile Ile Thr
            675                 680                 685

Lys Ser Phe Ala Arg Ile His Glu Thr Asn Leu Lys Lys Gln Gly Leu
            690                 695                 700

Leu Pro Leu Thr Phe Ala Asp Pro Ser Asp Tyr Asn Lys Ile His Pro
705                 710                 715                 720

Val Asp Lys Leu Thr Ile Gln Gly Leu Lys Asp Phe Ala Pro Gly Lys
                725                 730                 735

Pro Leu Asn Cys Ile Ile Lys His Pro Asn Gly Thr Gln Glu Thr Ile
            740                 745                 750

Leu Leu Asn His Thr Phe Asn Glu Thr Gln Ile Glu Trp Phe Arg Ala
            755                 760                 765

Gly Ser Ala Leu Asn Arg Met Lys Glu Leu Gln Gln
            770                 775                 780

<210> SEQ ID NO 35
<211> LENGTH: 763
<212> TYPE: PRT
<213> ORGANISM: Rattus norvegicus

<400> SEQUENCE: 35

Met Val Ala Ser Arg Ala Ile Gly Ser Leu Ser Arg Phe Ser Ala Phe
1               5                   10                  15

Arg Ile Leu Arg Ser Arg Gly Cys Ile Cys His Ser Phe Thr Thr Ser
            20                  25                  30

Ser Ala Leu Leu Ser Arg Thr His Ile Asn Tyr Gly Val Lys Gly Asp
        35                  40                  45

Val Ala Val Ile Arg Ile Asn Ser Pro Asn Ser Lys Val Asn Thr Leu
    50                  55                  60

Asn Lys Glu Val Gln Ser Glu Phe Val Glu Val Met Asn Glu Ile Trp
65                  70                  75                  80

Ala Asn Asp Gln Ile Arg Ser Ala Val Leu Ile Ser Ser Lys Pro Gly
                85                  90                  95

Cys Phe Val Ala Gly Ala Asp Ile Asn Met Leu Ala Ser Cys Thr Thr
```

```
            100                 105                 110
Pro Gln Glu Ala Ala Arg Ile Ser Gln Glu Gly Gln Lys Met Phe Glu
        115                 120                 125
Lys Leu Glu Lys Ser Pro Lys Pro Val Val Ala Ile Ser Gly Ser
130                 135                 140
Cys Leu Gly Gly Gly Leu Glu Leu Ala Ile Ala Cys Gln Tyr Arg Ile
145                 150                 155                 160
Ala Thr Lys Asp Arg Lys Thr Val Leu Gly Val Pro Glu Val Leu Leu
                165                 170                 175
Gly Ile Leu Pro Gly Ala Gly Gly Thr Gln Arg Leu Pro Lys Met Val
                180                 185                 190
Gly Val Pro Ala Ala Phe Asp Met Met Leu Thr Gly Arg Asn Ile Arg
                195                 200                 205
Ala Asp Arg Ala Lys Lys Met Gly Leu Val Asp Gln Leu Val Asp Pro
                210                 215                 220
Leu Gly Pro Gly Ile Lys Ser Pro Glu Glu Arg Thr Ile Glu Tyr Leu
225                 230                 235                 240
Glu Glu Val Ala Val Asn Phe Ala Lys Gly Leu Ala Asp Arg Lys Val
                245                 250                 255
Ser Ala Lys Gln Ser Lys Gly Leu Met Glu Lys Leu Thr Ser Tyr Ala
                260                 265                 270
Met Thr Ile Pro Phe Val Arg Gln Gln Val Tyr Lys Thr Val Glu Glu
                275                 280                 285
Lys Val Lys Lys Gln Thr Lys Gly Leu Tyr Pro Ala Pro Leu Lys Ile
                290                 295                 300
Ile Asp Ala Val Lys Thr Gly Leu Glu Gln Gly Asn Asp Ala Gly Tyr
305                 310                 315                 320
Leu Ala Glu Ser Glu Lys Phe Gly Glu Leu Ala Leu Thr Lys Glu Ser
                325                 330                 335
Lys Ala Leu Met Gly Leu Tyr Asn Gly Gln Val Leu Cys Lys Lys Asn
                340                 345                 350
Lys Phe Gly Ala Pro Gln Lys Thr Val Gln Gln Leu Ala Ile Leu Gly
                355                 360                 365
Ala Gly Leu Met Gly Ala Gly Ile Ala Gln Val Ser Val Asp Lys Gly
                370                 375                 380
Leu Lys Thr Leu Leu Lys Asp Thr Thr Val Thr Gly Leu Gly Arg Gly
385                 390                 395                 400
Gln Gln Gln Val Phe Lys Gly Leu Asn Asp Lys Val Lys Lys Lys Ala
                405                 410                 415
Leu Thr Ser Phe Glu Arg Asp Ser Ile Phe Ser Asn Leu Ile Gly Gln
                420                 425                 430
Leu Asp Tyr Lys Gly Phe Glu Lys Ala Asp Met Val Ile Glu Ala Val
                435                 440                 445
Phe Glu Asp Leu Ala Val Lys His Lys Val Leu Lys Glu Val Glu Ser
                450                 455                 460
Val Thr Pro Glu His Cys Ile Phe Ala Ser Asn Thr Ser Ala Leu Pro
465                 470                 475                 480
Ile Asn Gln Ile Ala Ala Val Ser Gln Arg Pro Glu Lys Val Ile Gly
                485                 490                 495
Met His Tyr Phe Ser Pro Val Asp Lys Met Gln Leu Leu Glu Ile Ile
                500                 505                 510
Thr Thr Asp Lys Thr Ser Lys Asp Thr Thr Ala Ser Ala Val Ala Val
                515                 520                 525
```

```
Gly Leu Lys Gln Gly Lys Val Ile Val Val Lys Asp Gly Pro Gly
        530                 535                 540

Phe Tyr Thr Thr Arg Cys Leu Ala Pro Met Met Ser Glu Val Ile Arg
545                 550                 555                 560

Ile Leu Gln Glu Gly Val Asp Pro Lys Lys Leu Asp Ala Leu Thr Thr
                565                 570                 575

Gly Phe Gly Phe Pro Val Gly Ala Ala Thr Leu Ala Asp Glu Val Gly
            580                 585                 590

Ile Asp Val Ala Gln His Val Ala Glu Asp Leu Gly Lys Ala Phe Gly
        595                 600                 605

Glu Arg Phe Gly Gly Ser Val Glu Leu Leu Lys Leu Met Val Ser
610                 615                 620

Lys Gly Phe Leu Gly Arg Lys Ser Gly Lys Gly Phe Tyr Ile Tyr Gln
625                 630                 635                 640

Ser Gly Ser Lys Asn Lys Asn Leu Asn Ser Glu Ile Asp Asn Ile Leu
                645                 650                 655

Val Asn Leu Arg Leu Pro Ala Lys Pro Glu Val Ser Ser Asp Glu Asp
                660                 665                 670

Ile Gln Tyr Arg Val Ile Thr Arg Phe Val Asn Glu Ala Val Leu Cys
        675                 680                 685

Leu Gln Glu Gly Ile Leu Ala Thr Pro Glu Gly Asp Ile Gly Ala
    690                 695                 700

Val Phe Gly Leu Gly Phe Pro Pro Cys Leu Gly Gly Pro Phe Arg Phe
705                 710                 715                 720

Val Asp Leu Tyr Gly Ala Gln Lys Val Val Asp Arg Leu Arg Lys Tyr
                725                 730                 735

Glu Ser Ala Tyr Gly Thr Gln Phe Thr Pro Cys Gln Leu Leu Arg Asp
            740                 745                 750

Leu Ala Asn Asn Ser Ser Lys Lys Phe Tyr Gln
        755                 760

<210> SEQ ID NO 36
<211> LENGTH: 154
<212> TYPE: PRT
<213> ORGANISM: Oryctolagus cuniculus

<400> SEQUENCE: 36

Met Gly Leu Ser Asp Ala Glu Trp Gln Leu Val Leu Asn Val Trp Gly
1               5                   10                  15

Lys Val Glu Ala Asp Leu Ala Gly His Gly Gln Glu Val Leu Ile Arg
                20                  25                  30

Leu Phe His Thr His Pro Glu Thr Leu Glu Lys Phe Asp Lys Phe Lys
            35                  40                  45

His Leu Lys Ser Glu Asp Glu Met Lys Ala Ser Glu Asp Leu Lys Lys
        50                  55                  60

His Gly Asn Thr Val Leu Thr Ala Leu Gly Ala Ile Leu Lys Lys Lys
65                  70                  75                  80

Gly His His Glu Ala Glu Ile Lys Pro Leu Ala Gln Ser His Ala Thr
                85                  90                  95

Lys His Lys Ile Pro Val Lys Tyr Leu Glu Phe Ile Ser Glu Ala Ile
            100                 105                 110

Ile His Val Leu His Ser Lys His Pro Gly Asp Phe Gly Ala Asp Ala
        115                 120                 125

Gln Ala Ala Met Ser Lys Ala Leu Glu Leu Phe Arg Asn Asp Ile Ala
    130                 135                 140
```

```
Ala Gln Tyr Lys Glu Leu Gly Phe Gln Gly
145                 150
```

<210> SEQ ID NO 37
<211> LENGTH: 199
<212> TYPE: PRT
<213> ORGANISM: Bos Taurus

<400> SEQUENCE: 37

```
Met Ala Pro Lys Lys Pro Asp Pro Lys Lys Asp Glu Ala Lys Ala Gly
1               5                   10                  15

Ala Lys Ala Ala Ala Pro Ala Pro Ala Pro Ala Pro Pro Ala
            20                  25                  30

Pro Glu Pro Ser Lys Glu Pro Glu Phe Asp Pro Ser Lys Ile Lys Ile
                35                  40                  45

Glu Phe Thr Pro Glu Gln Ile Glu Glu Phe Lys Glu Ala Phe Thr Leu
            50                  55                  60

Phe Asp Arg Thr Pro Lys Cys Glu Met Lys Ile Thr Tyr Gly Gln Cys
65                  70                  75                  80

Gly Asp Val Leu Arg Ala Leu Gly Gln Asn Pro Thr Gln Ala Glu Val
                85                  90                  95

Leu Arg Val Leu Gly Lys Pro Lys Gln Glu Glu Leu Asn Ser Lys Met
                100                 105                 110

Met Asp Phe Asp Thr Phe Leu Pro Met Leu Gln His Ile Ser Lys Asn
            115                 120                 125

Lys Asp Thr Gly Thr Tyr Glu Asp Phe Val Glu Gly Leu Arg Val Phe
130                 135                 140

Asp Lys Glu Gly Asn Gly Thr Val Met Gly Ala Glu Leu Arg His Val
145                 150                 155                 160

Leu Ala Thr Leu Gly Glu Lys Leu Thr Glu Asp Val Glu Lys Leu
                165                 170                 175

Met Ala Gly Gln Glu Asp Ser Asn Gly Cys Ile Asn Tyr Glu Ala Phe
            180                 185                 190

Val Lys His Ile Met Ala Gly
            195
```

<210> SEQ ID NO 38
<211> LENGTH: 1463
<212> TYPE: PRT
<213> ORGANISM: Rattus norvegicus

<400> SEQUENCE: 38

```
Met Met Ser Phe Val Gln Cys Gly Thr Trp Phe Leu Leu Thr Leu Leu
1               5                   10                  15

His Pro Ser Leu Ile Leu Ala Gln Gln Ser Asn Val Asp Glu Leu Gly
            20                  25                  30

Cys Asn Tyr Leu Gly Gln Ser Tyr Glu Ser Arg Asp Val Trp Lys Pro
            35                  40                  45

Glu Pro Cys Gln Ile Cys Val Cys Asp Ser Gly Ser Val Leu Cys Asp
            50                  55                  60

Asp Ile Met Cys Asp Asp Glu Pro Leu Asp Cys Pro Asn Pro Glu Ile
65                  70                  75                  80

Pro Phe Gly Glu Cys Cys Ala Ile Cys Pro Gln Pro Thr Pro Ala
                85                  90                  95

Pro Val Ile Pro Asp Gly Asn Arg Pro Gln Gly Pro Lys Gly Asp Pro
            100                 105                 110

Gly Pro Pro Gly Ile Pro Gly Arg Asn Gly Asp Pro Gly Leu Pro Gly
```

```
               115                 120                 125
Gln Pro Gly Leu Pro Gly Pro Gly Ser Pro Gly Ile Cys Glu Ser
130                 135                 140

Cys Pro Thr Gly Gly Gln Asn Tyr Ser Pro Gln Phe Asp Ser Tyr Asp
145                 150                 155                 160

Val Lys Ser Gly Val Gly Met Gly Gly Tyr Pro Gly Pro Ala Gly
            165                 170                 175

Pro Pro Gly Pro Gly Pro Gly Ser Ser Gly His Pro Gly Ser
        180                 185                 190

Pro Gly Ser Pro Gly Tyr Gln Gly Pro Pro Gly Glu Pro Gly Gln Ala
        195                 200                 205

Gly Pro Ala Gly Pro Pro Gly Pro Gly Ala Ile Gly Pro Ser Gly
210                 215                 220

Pro Ala Gly Lys Asp Gly Glu Ser Gly Arg Pro Gly Arg Pro Gly Glu
225                 230                 235                 240

Arg Gly Leu Pro Gly Pro Pro Gly Ile Lys Gly Pro Ala Gly Ile Pro
                245                 250                 255

Gly Phe Pro Gly Met Lys Gly His Arg Gly Phe Asp Gly Arg Asn Gly
            260                 265                 270

Glu Lys Gly Glu Thr Gly Ala Pro Gly Leu Lys Gly Glu Asn Gly Leu
        275                 280                 285

Pro Gly Asp Asn Gly Ala Pro Gly Pro Met Gly Pro Arg Gly Ala Pro
290                 295                 300

Gly Glu Arg Gly Arg Pro Gly Leu Pro Gly Ala Ala Gly Ala Arg Gly
305                 310                 315                 320

Asn Asp Gly Ala Arg Gly Ser Asp Gly Gln Pro Gly Pro Pro Gly Pro
                325                 330                 335

Pro Gly Thr Ala Gly Phe Pro Gly Ser Pro Gly Ala Lys Gly Glu Val
            340                 345                 350

Gly Pro Ala Gly Ser Pro Gly Ser Asn Gly Ser Pro Gly Gln Arg Gly
        355                 360                 365

Glu Pro Gly Pro Gln Gly His Ala Gly Ala Gln Gly Pro Pro Gly Pro
370                 375                 380

Pro Gly Asn Asn Gly Ser Pro Gly Gly Lys Gly Glu Met Gly Pro Ala
385                 390                 395                 400

Gly Ile Pro Gly Ala Pro Gly Leu Leu Gly Ala Arg Gly Pro Pro Gly
                405                 410                 415

Pro Ala Gly Ala Asn Gly Ala Pro Gly Gln Arg Gly Pro Ser Gly Glu
            420                 425                 430

Pro Gly Lys Asn Gly Ala Lys Gly Glu Pro Gly Ala Arg Gly Glu Arg
        435                 440                 445

Gly Glu Ala Gly Ser Pro Gly Ile Pro Gly Pro Lys Gly Glu Asp Gly
        450                 455                 460

Lys Asp Gly Ser Pro Gly Glu Pro Gly Ala Asn Gly Val Pro Gly Asn
465                 470                 475                 480

Pro Gly Glu Arg Gly Ala Pro Gly Phe Arg Gly Pro Ala Gly Pro Asn
                485                 490                 495

Gly Ala Pro Gly Glu Lys Gly Pro Ala Gly Glu Arg Gly Gly Pro Gly
            500                 505                 510

Pro Ala Gly Pro Arg Gly Val Ala Gly Glu Pro Gly Arg Asp Gly Thr
        515                 520                 525

Pro Gly Gly Pro Gly Ile Arg Gly Met Pro Gly Ser Pro Gly Gly Pro
530                 535                 540
```

-continued

```
Gly Asn Asp Gly Lys Pro Gly Pro Gly Ser Gln Gly Glu Ser Gly
545                 550                 555                 560

Arg Pro Gly Pro Gly Pro Ser Gly Pro Arg Gly Gln Pro Gly Val
                565                 570                 575

Met Gly Phe Pro Gly Pro Lys Gly Asn Asp Gly Ala Pro Gly Lys Asn
            580                 585                 590

Gly Glu Arg Gly Gly Pro Gly Gly Pro Gly Leu Pro Gly Pro Ala Gly
        595                 600                 605

Lys Asn Gly Glu Thr Gly Pro Gln Gly Pro Pro Gly Pro Thr Gly Ala
610                 615                 620

Pro Gly Asp Lys Gly Asp Ala Gly Pro Pro Gly Pro Gln Gly Leu Gln
625                 630                 635                 640

Gly Ile Pro Gly Thr Ser Gly Pro Pro Gly Glu Asn Gly Lys Pro Gly
                645                 650                 655

Glu Pro Gly Pro Lys Gly Glu Ala Gly Ala Pro Gly Val Pro Gly Gly
                660                 665                 670

Lys Gly Asp Ser Gly Ala Pro Gly Glu Arg Gly Pro Pro Gly Thr Ala
            675                 680                 685

Gly Thr Pro Gly Leu Arg Gly Gly Ala Gly Pro Pro Gly Pro Glu Gly
        690                 695                 700

Gly Lys Gly Pro Ala Gly Pro Pro Gly Pro Gly Thr Ser Gly Pro
705                 710                 715                 720

Pro Gly Leu Gln Gly Met Pro Gly Glu Arg Gly Gly Pro Gly Ser Pro
                725                 730                 735

Gly Pro Lys Gly Glu Lys Gly Glu Pro Gly Gly Ala Gly Ala Asp Gly
            740                 745                 750

Val Pro Gly Lys Asp Gly Pro Arg Gly Pro Ala Gly Pro Ile Gly Pro
        755                 760                 765

Pro Gly Pro Ala Gly Gln Pro Gly Asp Lys Gly Glu Gly Gly Ala Pro
770                 775                 780

Gly Leu Pro Gly Ile Ala Gly Pro Arg Gly Pro Gly Glu Arg Gly
785                 790                 795                 800

Glu His Gly Pro Pro Gly Pro Ala Gly Phe Pro Gly Ala Pro Gly Gln
                805                 810                 815

Asn Gly Glu Pro Gly Ala Lys Gly Glu Arg Gly Ala Pro Gly Glu Lys
            820                 825                 830

Gly Glu Gly Gly Pro Pro Gly Ala Ala Gly Pro Pro Gly Gly Ser Gly
        835                 840                 845

Pro Ala Gly Pro Pro Gly Pro Gln Gly Val Lys Gly Glu Arg Gly Ser
850                 855                 860

Pro Gly Gly Pro Gly Ala Ala Gly Phe Pro Gly Gly Arg Gly Leu Pro
865                 870                 875                 880

Gly Pro Pro Gly Asn Asn Gly Asn Pro Gly Pro Pro Gly Pro Ser Gly
                885                 890                 895

Ala Pro Gly Lys Asp Gly Pro Pro Gly Pro Ala Gly Asn Ser Gly Ser
            900                 905                 910

Pro Gly Asn Pro Gly Val Ala Gly Pro Lys Gly Asp Ala Gly Gln Pro
        915                 920                 925

Gly Glu Lys Gly Pro Pro Gly Ala Gln Gly Pro Pro Gly Ser Pro Gly
930                 935                 940

Pro Leu Gly Ile Ala Gly Leu Thr Gly Ala Arg Gly Leu Ala Gly Pro
945                 950                 955                 960

Pro Gly Met Pro Gly Pro Arg Gly Ser Pro Gly Pro Gln Gly Ile Lys
                965                 970                 975
```

```
Gly Glu Ser Gly Lys Pro Gly Ala Ser Gly His Asn Gly Glu Arg Gly
                980                 985                 990

Pro Pro Gly Pro Gln Gly Leu Pro  Gly Gln Pro Gly Thr  Ala Gly Glu
        995                1000                 1005

Pro Gly  Arg Asp Gly Asn Pro  Gly Ser Asp Gly Gln  Pro Gly Arg
    1010                 1015                 1020

Asp Gly  Ser Pro Gly Gly Lys  Gly Asp Arg Gly Glu   Asn Gly Ser
    1025                 1030                  1035

Pro Gly  Ala Pro Gly Ala Pro  Gly His Pro Gly Pro  Pro Gly Pro
    1040                 1045                 1050

Val Gly  Pro Ser Gly Lys Asn  Gly Asp Arg Gly Glu   Thr Gly Pro
    1055                 1060                  1065

Ala Gly  Pro Ser Gly Ala Pro  Gly Pro Ala Gly Ala  Arg Gly Ala
    1070                 1075                 1080

Pro Gly  Pro Gln Gly Pro Arg  Gly Asp Lys Gly Glu   Thr Gly Glu
    1085                 1090                  1095

Arg Gly  Ser Asn Gly Ile Lys  Gly His Arg Gly Phe  Pro Gly Asn
    1100                 1105                 1110

Pro Gly  Pro Pro Gly Ser Pro  Gly Ala Ala Gly His  Gln Gly Ala
    1115                 1120                 1125

Val Gly  Ser Pro Gly Pro Ala  Gly Pro Arg Gly Pro  Val Gly Pro
    1130                 1135                 1140

His Gly  Pro Pro Gly Lys Asp  Gly Ser Ser Gly His  Pro Gly Pro
    1145                 1150                 1155

Ile Gly  Pro Pro Gly Pro Arg  Gly Asn Arg Gly Glu  Arg Gly Ser
    1160                 1165                 1170

Glu Gly  Ser Pro Gly His Pro  Gly Gln Pro Gly Pro  Pro Gly Pro
    1175                 1180                 1185

Pro Gly  Ala Pro Gly Pro Cys  Cys Gly Gly Gly Ala  Ala Ile Ala
    1190                 1195                 1200

Gly Val  Gly Gly Glu Lys Ser  Gly Gly Phe Ser Pro  Tyr Tyr Gly
    1205                 1210                 1215

Asp Asp  Pro Met Asp Phe Lys  Ile Asn Thr Glu Glu   Ile Met Ser
    1220                 1225                  1230

Ser Leu  Lys Ser Val Asn Gly  Gln Ile Glu Ser Leu   Ile Ser Pro
    1235                 1240                  1245

Asp Gly  Ser Arg Lys Asn Pro  Ala Arg Asn Cys Arg  Asp Leu Lys
    1250                 1255                 1260

Phe Cys  His Pro Glu Leu Lys  Ser Gly Glu Tyr Trp  Val Asp Pro
    1265                 1270                 1275

Asn Gln  Gly Cys Lys Met Asp  Ala Ile Lys Val Phe  Cys Asn Met
    1280                 1285                 1290

Glu Thr  Gly Glu Thr Cys Ile  Asn Ala Ser Pro Met  Thr Val Pro
    1295                 1300                 1305

Arg Lys  His Trp Trp Thr Asp  Ala Gly Ala Glu Lys  Lys His Val
    1310                 1315                 1320

Trp Phe  Gly Glu Ser Met Asn  Gly Gly Phe Gln Phe  Ser Tyr Gly
    1325                 1330                 1335

Asn Pro  Asp Leu Pro Glu Asp  Val Leu Asp Val Gln  Leu Ala Phe
    1340                 1345                 1350

Leu Arg  Leu Leu Ser Ser Arg  Ala Ser Gln Asn Ile  Thr Tyr His
    1355                 1360                 1365

Cys Lys  Asn Ser Ile Ala Tyr  Met Asp Gln Ala Asn  Gly Asn Val
```

-continued

```
                1370                1375                1380
Lys Lys Ser Leu Lys Leu Met Gly Ser Asn Glu Gly Glu Phe Lys
        1385                1390                1395
Ala Glu Gly Asn Ser Lys Phe Thr Tyr Thr Val Leu Glu Asp Gly
    1400                1405                1410
Cys Thr Lys His Thr Gly Glu Trp Ser Lys Thr Val Phe Glu Tyr
    1415                1420                1425
Gln Thr Arg Lys Ala Met Arg Leu Pro Ile Ile Asp Ile Ala Pro
    1430                1435                1440
Tyr Asp Ile Gly Gly Pro Asp Gln Glu Phe Gly Val Asp Ile Gly
    1445                1450                1455
Pro Val Cys Phe Leu
    1460

<210> SEQ ID NO 39
<211> LENGTH: 1838
<212> TYPE: PRT
<213> ORGANISM: Mus musculus

<400> SEQUENCE: 39

Met Asp Val His Thr Arg Trp Lys Ala Ala Arg Pro Gly Ala Leu Leu
1               5                   10                  15
Leu Ser Ser Pro Leu Leu Leu Phe Leu Leu Leu Trp Ala Pro Pro
            20                  25                  30
Ser Ser Arg Ala Ala Gln Pro Ala Asp Leu Leu Glu Met Leu Asp Phe
            35                  40                  45
His Asn Leu Pro Ser Gly Val Thr Lys Thr Thr Gly Phe Cys Ala Thr
        50                  55                  60
Arg Arg Ser Ser Ser Glu Pro Asp Val Ala Tyr Arg Val Ser Lys Asp
65                  70                  75                  80
Ala Gln Leu Ser Met Pro Thr Lys Gln Leu Tyr Pro Glu Ser Gly Phe
                85                  90                  95
Pro Glu Asp Phe Ser Ile Leu Thr Thr Val Lys Ala Lys Lys Gly Ser
            100                 105                 110
Gln Ala Phe Leu Val Ser Ile Tyr Asn Glu Gln Gly Ile Gln Gln Leu
        115                 120                 125
Gly Leu Glu Leu Gly Arg Ser Pro Val Phe Leu Tyr Glu Asp His Thr
    130                 135                 140
Gly Lys Pro Gly Pro Glu Glu Tyr Pro Leu Phe Pro Gly Ile Asn Leu
145                 150                 155                 160
Ser Asp Gly Lys Trp His Arg Ile Ala Leu Ser Val Tyr Lys Lys Asn
                165                 170                 175
Val Thr Leu Ile Leu Asp Cys Lys Lys Lys Ile Thr Lys Phe Leu Ser
            180                 185                 190
Arg Ser Asp His Pro Ile Ile Asp Thr Asn Gly Ile Val Met Phe Gly
        195                 200                 205
Ser Arg Ile Leu Asp Asp Glu Ile Phe Glu Gly Asp Ile Gln Gln Leu
    210                 215                 220
Leu Phe Val Ser Asp Asn Arg Ala Ala Tyr Asp Tyr Cys Glu His Tyr
225                 230                 235                 240
Ser Pro Asp Cys Asp Thr Ala Val Pro Asp Thr Pro Gln Ser Gln Asp
                245                 250                 255
Pro Asn Pro Asp Glu Tyr Tyr Pro Glu Gly Glu Gly Glu Thr Tyr Tyr
            260                 265                 270
Tyr Glu Tyr Pro Tyr Tyr Glu Asp Pro Glu Asp Pro Gly Lys Glu Pro
```

```
                    275                 280                 285
Ala Pro Thr Gln Lys Pro Val Glu Ala Arg Glu Thr Thr Glu Val
290                 295                 300
Pro Glu Glu Gln Thr Gln Pro Leu Pro Glu Ala Pro Thr Val Pro Glu
305                 310                 315                 320
Thr Ser Asp Thr Ala Asp Lys Glu Asp Ser Leu Gly Ile Gly Asp Tyr
                325                 330                 335
Asp Tyr Val Pro Pro Asp Tyr Tyr Thr Pro Pro Tyr Glu Asp
                340                 345                 350
Phe Gly Tyr Gly Glu Gly Val Glu Asn Pro Asp Gln Pro Thr Asn Pro
                355                 360                 365
Asp Ser Gly Ala Glu Val Pro Thr Ser Thr Val Thr Ser Asn Thr
                370                 375                 380
Ser Asn Pro Ala Pro Gly Glu Gly Lys Asp Asp Leu Gly Gly Glu Phe
385                 390                 395                 400
Thr Glu Glu Thr Ile Lys Asn Leu Glu Glu Asn Tyr Tyr Asp Pro Tyr
                405                 410                 415
Phe Asp Pro Asp Ser Asp Ser Ser Val Ser Pro Ser Glu Ile Gly Pro
                420                 425                 430
Gly Met Pro Ala Asn Gln Asp Thr Ile Phe Glu Gly Ile Gly Gly Pro
                435                 440                 445
Arg Gly Glu Lys Gly Gln Lys Gly Glu Pro Ala Ile Ile Glu Pro Gly
450                 455                 460
Met Leu Ile Glu Gly Pro Pro Gly Pro Glu Gly Pro Ala Gly Leu Pro
465                 470                 475                 480
Gly Pro Pro Gly Thr Thr Gly Pro Thr Gly Gln Met Gly Asp Pro Gly
                485                 490                 495
Glu Arg Gly Pro Pro Gly Arg Pro Gly Leu Pro Gly Ala Asp Gly Leu
                500                 505                 510
Pro Gly Pro Pro Gly Thr Met Leu Met Leu Pro Phe Arg Phe Gly Gly
                515                 520                 525
Gly Gly Asp Ala Gly Ser Lys Gly Pro Met Val Ser Ala Gln Glu Ser
530                 535                 540
Gln Ala Gln Ala Ile Leu Gln Gln Ala Arg Leu Ala Leu Arg Gly Pro
545                 550                 555                 560
Ala Gly Pro Met Gly Leu Thr Gly Arg Pro Gly Pro Met Gly Pro Pro
                565                 570                 575
Gly Ser Gly Gly Leu Lys Gly Glu Pro Gly Asp Met Gly Pro Gln Gly
                580                 585                 590
Pro Arg Gly Val Gln Gly Pro Pro Gly Pro Thr Gly Lys Pro Gly Arg
                595                 600                 605
Arg Gly Arg Ala Gly Ser Asp Gly Ala Arg Gly Met Pro Gly Gln Thr
                610                 615                 620
Gly Pro Lys Gly Asp Arg Gly Phe Asp Gly Leu Ala Gly Leu Pro Gly
625                 630                 635                 640
Glu Lys Gly His Arg Gly Asp Pro Gly Pro Ser Gly Pro Pro Gly Ile
                645                 650                 655
Pro Gly Asp Asp Gly Glu Arg Gly Asp Asp Gly Glu Val Gly Pro Arg
                660                 665                 670
Gly Leu Pro Gly Glu Pro Gly Pro Arg Gly Leu Leu Gly Pro Lys Gly
                675                 680                 685
Pro Pro Gly Pro Pro Gly Pro Pro Gly Val Thr Gly Met Asp Gly Gln
                690                 695                 700
```

-continued

Pro Gly Pro Lys Gly Asn Val Gly Pro Gln Gly Glu Pro Gly Pro Pro
705                 710                 715                 720

Gly Gln Gln Gly Asn Pro Gly Ala Gln Gly Leu Pro Gly Pro Gln Gly
            725                 730                 735

Ala Ile Gly Pro Pro Gly Glu Lys Gly Pro Leu Gly Lys Pro Gly Leu
        740                 745                 750

Pro Gly Met Pro Gly Ala Asp Gly Pro Pro Gly His Pro Gly Lys Glu
    755                 760                 765

Gly Pro Pro Gly Glu Lys Gly Gln Gly Pro Pro Gly Pro Gln Gly
770                 775                 780

Pro Ile Gly Tyr Pro Gly Pro Arg Gly Val Lys Gly Ala Asp Gly Ile
785                 790                 795                 800

Arg Gly Leu Lys Gly Thr Lys Gly Glu Lys Gly Glu Asp Gly Phe Pro
            805                 810                 815

Gly Phe Lys Gly Asp Met Gly Ile Lys Gly Asp Arg Gly Glu Ile Gly
        820                 825                 830

Pro Pro Gly Pro Arg Gly Glu Asp Gly Pro Glu Gly Pro Lys Gly Arg
    835                 840                 845

Gly Gly Pro Asn Gly Asp Pro Gly Pro Leu Gly Pro Thr Gly Glu Lys
850                 855                 860

Gly Lys Leu Gly Val Pro Gly Leu Pro Gly Tyr Pro Gly Arg Gln Gly
865                 870                 875                 880

Pro Lys Gly Ser Ile Gly Phe Pro Gly Phe Pro Gly Ala Asn Gly Glu
            885                 890                 895

Lys Gly Gly Arg Gly Thr Pro Gly Lys Pro Gly Pro Arg Gly Gln Arg
        900                 905                 910

Gly Pro Thr Gly Pro Arg Gly Glu Arg Gly Pro Arg Gly Ile Thr Gly
    915                 920                 925

Lys Pro Gly Pro Lys Gly Asn Ser Gly Gly Asp Gly Pro Ala Gly Pro
930                 935                 940

Pro Gly Glu Arg Gly Pro Asn Gly Pro Gln Gly Pro Thr Gly Phe Pro
945                 950                 955                 960

Gly Pro Lys Gly Pro Pro Gly Pro Pro Gly Lys Asp Gly Leu Pro Gly
            965                 970                 975

His Pro Gly Gln Arg Gly Glu Thr Gly Phe Gln Gly Lys Thr Gly Pro
        980                 985                 990

Pro Gly Pro Pro Gly Val Val Gly Pro Gln Gly Pro Thr Gly Glu Thr
    995                 1000                1005

Gly Pro Met Gly Glu Arg Gly His Pro Gly Pro Pro Gly Pro Pro
    1010                1015                1020

Gly Glu Gln Gly Leu Pro Gly Ala Ala Gly Lys Glu Gly Thr Lys
    1025                1030                1035

Gly Asp Pro Gly Pro Ala Gly Leu Pro Gly Lys Asp Gly Pro Pro
    1040                1045                1050

Gly Leu Arg Gly Phe Pro Gly Asp Arg Gly Leu Pro Gly Pro Val
    1055                1060                1065

Gly Ala Leu Gly Leu Lys Gly Ser Glu Gly Pro Pro Gly Pro Pro
    1070                1075                1080

Gly Pro Ala Gly Ser Pro Gly Glu Arg Gly Pro Ala Gly Ala Ala
    1085                1090                1095

Gly Pro Ile Gly Ile Pro Gly Arg Pro Gly Pro Gln Gly Pro Pro
    1100                1105                1110

Gly Pro Ala Gly Glu Lys Gly Leu Pro Gly Glu Lys Gly Pro Gln
    1115                1120                1125

```
Gly Pro Ala Gly Arg Asp Gly Leu Gln Gly Pro Val Gly Leu Pro
    1130            1135                1140

Gly Pro Ala Gly Pro Val Gly Pro Gly Glu Asp Gly Asp Lys
    1145            1150                1155

Gly Glu Ile Gly Glu Pro Gly Gln Lys Gly Ser Lys Gly Asp Lys
    1160            1165                1170

Gly Glu Gln Gly Pro Pro Gly Pro Thr Gly Pro Gln Gly Pro Ile
    1175            1180                1185

Gly Gln Pro Gly Pro Ser Gly Ala Asp Gly Glu Pro Gly Pro Arg
    1190            1195                1200

Gly Gln Gln Gly Leu Phe Gly Gln Lys Gly Asp Glu Gly Ser Arg
    1205            1210                1215

Gly Phe Pro Gly Pro Pro Gly Pro Val Gly Leu Gln Gly Leu Pro
    1220            1225                1230

Gly Pro Pro Gly Glu Lys Gly Glu Thr Gly Asp Val Gly Gln Met
    1235            1240                1245

Gly Pro Pro Gly Pro Pro Gly Pro Arg Gly Pro Ser Gly Ala Pro
    1250            1255                1260

Gly Ala Asp Gly Pro Gln Gly Pro Pro Gly Gly Ile Gly Asn Pro
    1265            1270                1275

Gly Ala Val Gly Glu Lys Gly Glu Pro Gly Glu Ala Gly Asp Pro
    1280            1285                1290

Gly Leu Pro Gly Glu Gly Gly Pro Leu Gly Pro Lys Gly Glu Arg
    1295            1300                1305

Gly Glu Lys Gly Glu Ala Gly Pro Ser Gly Ala Ala Gly Pro Pro
    1310            1315                1320

Gly Pro Lys Gly Pro Pro Gly Asp Asp Gly Pro Lys Gly Ser Pro
    1325            1330                1335

Gly Pro Val Gly Phe Pro Gly Asp Pro Gly Pro Pro Gly Glu Pro
    1340            1345                1350

Gly Pro Ala Gly Gln Asp Gly Pro Pro Gly Asp Lys Gly Asp Asp
    1355            1360                1365

Gly Glu Pro Gly Gln Thr Gly Ser Pro Gly Pro Thr Gly Glu Pro
    1370            1375                1380

Gly Pro Ser Gly Pro Pro Gly Lys Arg Gly Pro Pro Gly Pro Ala
    1385            1390                1395

Gly Pro Glu Gly Arg Gln Gly Glu Lys Gly Ala Lys Gly Glu Ala
    1400            1405                1410

Gly Leu Glu Gly Pro Pro Gly Lys Thr Gly Pro Ile Gly Pro Gln
    1415            1420                1425

Gly Ala Pro Gly Lys Pro Gly Pro Asp Gly Leu Arg Gly Ile Pro
    1430            1435                1440

Gly Pro Val Gly Glu Gln Gly Leu Pro Gly Ser Pro Gly Pro Asp
    1445            1450                1455

Gly Pro Pro Gly Pro Met Gly Pro Pro Gly Leu Pro Gly Leu Lys
    1460            1465                1470

Gly Asp Ser Gly Pro Lys Gly Glu Lys Gly His Pro Gly Leu Ile
    1475            1480                1485

Gly Leu Ile Gly Pro Pro Gly Glu Gln Gly Glu Lys Gly Asp Arg
    1490            1495                1500

Gly Leu Pro Gly Pro Gln Gly Ser Ser Gly Pro Lys Gly Asp Gln
    1505            1510                1515

Gly Ile Thr Gly Pro Ser Gly Pro Leu Gly Pro Pro Gly Pro Pro
```

Gly Leu Pro Gly Pro Pro Gly Pro Lys Gly Ala Lys Gly Ser Ser
1535                1540                1545

Gly Pro Thr Gly Pro Lys Gly Glu Ala Gly His Pro Gly Leu Pro
1550                1555                1560

Gly Pro Pro Gly Pro Pro Gly Glu Val Ile Gln Pro Leu Pro Ile
1565                1570                1575

Gln Ala Ser Arg Thr Arg Arg Asn Ile Asp Ala Ser Gln Leu Leu
1580                1585                1590

Asp Asp Gly Ala Gly Glu Ser Tyr Val Asp Tyr Ala Asp Gly Met
1595                1600                1605

Glu Glu Ile Phe Gly Ser Leu Asn Ser Leu Lys Leu Glu Ile Glu
1610                1615                1620

Gln Met Lys Arg Pro Leu Gly Thr Gln Gln Asn Pro Ala Arg Thr
1625                1630                1635

Cys Lys Asp Leu Gln Leu Cys His Pro Asp Phe Pro Asp Gly Glu
1640                1645                1650

Tyr Trp Val Asp Pro Asn Gln Gly Cys Ser Arg Asp Ser Phe Lys
1655                1660                1665

Val Tyr Cys Asn Phe Thr Ala Gly Gly Ser Thr Cys Val Phe Pro
1670                1675                1680

Asp Lys Lys Ser Glu Gly Ala Arg Ile Thr Ser Trp Pro Lys Glu
1685                1690                1695

Asn Pro Gly Ser Trp Phe Ser Glu Phe Lys Arg Gly Lys Leu Leu
1700                1705                1710

Ser Tyr Val Asp Ala Glu Gly Asn Pro Val Gly Val Val Gln Met
1715                1720                1725

Thr Phe Leu Arg Leu Leu Ser Ala Ser Ala His Gln Asn Val Thr
1730                1735                1740

Tyr Asn Cys Tyr Gln Ser Val Ala Trp Gln Asp Ala Ala Thr Gly
1745                1750                1755

Ser Tyr Asp Lys Ala Ile Arg Phe Leu Gly Ser Asn Asp Glu Glu
1760                1765                1770

Met Ser Tyr Asp Asn Asn Pro Tyr Ile Arg Ala Leu Val Asp Gly
1775                1780                1785

Cys Ala Thr Lys Lys Gly Tyr Gln Lys Thr Val Leu Glu Ile Asp
1790                1795                1800

Thr Pro Lys Val Glu Gln Val Pro Ile Val Asp Ile Met Phe Asn
1805                1810                1815

Asp Phe Gly Glu Ala Ser Gln Lys Phe Gly Phe Glu Val Gly Pro
1820                1825                1830

Ala Cys Phe Leu Gly
1835

<210> SEQ ID NO 40
<211> LENGTH: 1043
<212> TYPE: PRT
<213> ORGANISM: Rattus norvegicus

<400> SEQUENCE: 40

Met Glu Asn Ala His Thr Lys Thr Val Glu Glu Val Leu Gly His Phe
1               5                   10                  15

Gly Val Asn Glu Ser Thr Gly Leu Ser Leu Glu Gln Val Lys Lys Leu
                20                  25                  30

Lys Glu Arg Trp Gly Ser Asn Glu Leu Pro Ala Glu Glu Gly Lys Thr

-continued

```
                35                  40                  45
Leu Leu Glu Leu Val Ile Glu Gln Phe Glu Asp Leu Leu Val Arg Ile
 50                  55                  60
Leu Leu Leu Ala Ala Cys Ile Ser Phe Val Leu Ala Trp Phe Glu Glu
 65                  70                  75                  80
Gly Glu Glu Thr Ile Thr Ala Phe Val Glu Pro Phe Val Ile Leu Leu
                 85                  90                  95
Ile Leu Val Ala Asn Ala Ile Val Gly Val Trp Gln Glu Arg Asn Ala
                100                 105                 110
Glu Asn Ala Ile Glu Ala Leu Lys Glu Tyr Glu Pro Glu Met Gly Lys
            115                 120                 125
Val Tyr Arg Gln Asp Arg Lys Ser Val Gln Arg Ile Lys Ala Lys Asp
        130                 135                 140
Ile Val Pro Gly Asp Ile Val Glu Ile Ala Val Gly Asp Lys Val Pro
    145                 150                 155                 160
Ala Asp Ile Arg Leu Thr Ser Ile Lys Ser Thr Thr Leu Arg Val Asp
                165                 170                 175
Gln Ser Ile Leu Thr Gly Glu Ser Val Ser Val Ile Lys His Thr Asp
                180                 185                 190
Pro Val Pro Asp Pro Arg Ala Val Asn Gln Asp Lys Lys Asn Met Leu
            195                 200                 205
Phe Ser Gly Thr Asn Ile Ala Ala Gly Lys Ala Met Gly Val Val Val
        210                 215                 220
Ala Thr Gly Val Asn Thr Glu Ile Gly Lys Ile Arg Asp Glu Met Val
225                 230                 235                 240
Ala Thr Glu Gln Glu Arg Thr Pro Leu Gln Gln Lys Leu Asp Glu Phe
                245                 250                 255
Gly Glu Gln Leu Ser Lys Val Ile Ser Leu Ile Cys Ile Ala Val Trp
            260                 265                 270
Ile Ile Asn Ile Gly His Phe Asn Asp Pro Val His Gly Gly Ser Trp
        275                 280                 285
Ile Arg Gly Ala Ile Tyr Tyr Phe Lys Ile Ala Val Ala Leu Ala Val
    290                 295                 300
Ala Ala Ile Pro Glu Gly Leu Pro Ala Val Ile Thr Thr Cys Leu Ala
305                 310                 315                 320
Leu Gly Thr Arg Arg Met Ala Lys Lys Asn Ala Ile Val Arg Ser Leu
                325                 330                 335
Pro Ser Val Glu Thr Leu Gly Cys Thr Ser Val Ile Cys Ser Asp Lys
            340                 345                 350
Thr Gly Thr Leu Thr Thr Asn Gln Met Ser Val Cys Arg Met Phe Ile
        355                 360                 365
Leu Asp Lys Val Glu Gly Asp Thr Cys Ser Leu Asn Glu Phe Thr Ile
    370                 375                 380
Thr Gly Ser Thr Tyr Ala Pro Ile Gly Glu Val Gln Lys Asp Asp Lys
385                 390                 395                 400
Pro Val Lys Cys His Gln Tyr Asp Gly Leu Val Glu Leu Ala Thr Ile
                405                 410                 415
Cys Ala Leu Cys Asn Asp Ser Ala Leu Asp Tyr Asn Glu Ala Lys Gly
            420                 425                 430
Val Tyr Glu Lys Val Gly Glu Ala Thr Glu Thr Ala Leu Thr Cys Leu
        435                 440                 445
Val Glu Lys Met Asn Val Phe Asp Thr Glu Leu Lys Gly Leu Ser Lys
    450                 455                 460
```

```
Ile Glu Arg Ala Asn Ala Cys Asn Ser Val Ile Lys Gln Leu Met Lys
465                 470                 475                 480

Lys Glu Phe Thr Leu Glu Phe Ser Arg Asp Arg Lys Ser Met Ser Val
            485                 490                 495

Tyr Cys Thr Pro Asn Lys Pro Ser Arg Thr Ser Met Ser Lys Met Phe
                500                 505                 510

Val Lys Gly Ala Pro Glu Gly Val Ile Asp Arg Cys Thr His Ile Arg
            515                 520                 525

Val Gly Ser Thr Lys Val Pro Met Thr Pro Gly Val Lys Gln Lys Ile
            530                 535                 540

Met Ser Val Ile Arg Glu Trp Gly Ser Gly Ser Asp Thr Leu Arg Cys
545                 550                 555                 560

Leu Ala Leu Ala Thr His Asp Asn Pro Leu Arg Arg Glu Glu Met His
                565                 570                 575

Leu Glu Asp Ser Ala Asn Phe Ile Lys Tyr Glu Thr Asn Leu Thr Phe
            580                 585                 590

Val Gly Cys Val Gly Met Leu Asp Pro Pro Arg Ile Glu Val Ala Ser
            595                 600                 605

Ser Val Lys Leu Cys Arg Gln Ala Gly Ile Arg Val Ile Met Ile Thr
610                 615                 620

Gly Asp Asn Lys Gly Thr Ala Val Ala Ile Cys Arg Arg Ile Gly Ile
625                 630                 635                 640

Phe Gly Gln Asp Glu Asp Val Thr Ser Lys Ala Phe Thr Gly Arg Glu
                645                 650                 655

Phe Asp Glu Leu Ser Pro Ser Ala Gln Arg Asp Ala Cys Leu Asn Ala
            660                 665                 670

Arg Cys Phe Ala Arg Val Glu Pro Ser His Lys Ser Lys Ile Val Glu
            675                 680                 685

Phe Leu Gln Ser Phe Asp Glu Ile Thr Ala Met Thr Gly Asp Gly Val
            690                 695                 700

Asn Asp Ala Pro Ala Leu Lys Lys Ser Glu Ile Gly Ile Ala Met Gly
705                 710                 715                 720

Ser Gly Thr Ala Val Ala Lys Thr Ala Ser Glu Met Val Leu Ala Asp
                725                 730                 735

Asp Asn Phe Ser Thr Ile Val Ala Ala Val Glu Glu Gly Arg Ala Ile
            740                 745                 750

Tyr Asn Asn Met Lys Gln Phe Ile Arg Tyr Leu Ile Ser Ser Asn Val
            755                 760                 765

Gly Glu Val Val Cys Ile Phe Leu Thr Ala Ala Leu Gly Phe Pro Glu
            770                 775                 780

Ala Leu Ile Pro Val Gln Leu Leu Trp Val Asn Leu Val Thr Asp Gly
785                 790                 795                 800

Leu Pro Ala Thr Ala Leu Gly Phe Asn Pro Pro Asp Leu Asp Ile Met
                805                 810                 815

Asn Lys Pro Pro Arg Asn Pro Lys Glu Pro Leu Ile Ser Gly Trp Leu
            820                 825                 830

Phe Phe Arg Tyr Leu Ala Ile Gly Cys Tyr Val Gly Ala Ala Thr Val
            835                 840                 845

Gly Ala Ala Ala Trp Trp Phe Ile Ala Ala Asp Gly Gly Pro Arg Val
850                 855                 860

Ser Phe Tyr Gln Leu Ser His Phe Leu Gln Cys Lys Glu Asp Asn Pro
865                 870                 875                 880

Asp Phe Glu Gly Val Asp Cys Ala Ile Phe Glu Ser Pro Tyr Pro Met
                885                 890                 895
```

```
Thr Met Ala Leu Ser Val Leu Val Thr Ile Glu Met Cys Asn Ala Leu
            900                 905                 910

Asn Ser Leu Ser Glu Asn Gln Ser Leu Leu Arg Met Pro Pro Trp Glu
            915                 920                 925

Asn Ile Trp Leu Val Gly Ser Ile Cys Leu Ser Ser Leu His Phe
            930                 935                 940

Leu Ile Leu Tyr Val Glu Pro Leu Pro Leu Ile Phe Gln Ile Thr Pro
945                 950                 955                 960

Leu Asn Leu Thr Gln Trp Leu Met Val Leu Lys Ile Ser Leu Pro Val
            965                 970                 975

Ile Leu Met Asp Glu Thr Leu Lys Phe Val Ala Arg Asn Tyr Leu Glu
            980                 985                 990

Pro Gly Lys Glu Cys Ala Gln Pro  Ala Thr Lys Pro Ser  Cys Ser Leu
            995                 1000                1005

Ser Ala  Cys Thr Asp Gly Ile  Ser Trp Pro Phe Val  Leu Leu Ile
    1010                1015                1020

Met Pro  Leu Val Val Trp Val  Tyr Ser Thr Asp Thr  Asn Phe Ser
    1025                1030                1035

Asp Met  Phe Trp Ser
    1040

<210> SEQ ID NO 41
<211> LENGTH: 1453
<212> TYPE: PRT
<213> ORGANISM: Rattus norvegicus

<400> SEQUENCE: 41

Met Phe Ser Phe Val Asp Leu Arg Leu Leu Leu Leu Leu Gly Ala Thr
1               5                   10                  15

Ala Leu Leu Thr His Gly Gln Glu Asp Ile Pro Glu Val Ser Cys Ile
            20                  25                  30

His Asn Gly Leu Arg Val Pro Asn Gly Glu Thr Trp Lys Pro Asp Val
        35                  40                  45

Cys Leu Ile Cys Ile Cys His Asn Gly Thr Ala Val Cys Asp Gly Val
    50                  55                  60

Leu Cys Lys Glu Asp Leu Asp Cys Pro Asn Pro Gln Lys Arg Glu Gly
65                  70                  75                  80

Glu Cys Cys Pro Phe Cys Pro Glu Glu Tyr Val Ser Pro Asp Ala Glu
                85                  90                  95

Val Ile Gly Val Glu Gly Pro Lys Gly Asp Pro Gly Pro Gln Gly Pro
            100                 105                 110

Arg Gly Pro Val Gly Pro Pro Gly Gln Asp Gly Ile Pro Gly Gln Pro
        115                 120                 125

Gly Leu Pro Gly Pro Pro Gly Pro Gly Pro Pro Gly Pro Pro Gly
    130                 135                 140

Leu Gly Gly Asn Phe Ala Ser Gln Met Ser Tyr Gly Tyr Asp Glu Lys
145                 150                 155                 160

Ser Ala Gly Val Ser Val Pro Gly Pro Met Gly Pro Ser Gly Pro Arg
                165                 170                 175

Gly Leu Pro Gly Pro Pro Gly Ala Pro Gly Gln Gly Phe Gln Gly
            180                 185                 190

Pro Pro Gly Glu Pro Gly Glu Pro Gly Ala Ser Gly Pro Met Gly Pro
        195                 200                 205

Arg Gly Pro Pro Gly Pro Pro Gly Lys Asn Gly Asp Asp Gly Glu Ala
    210                 215                 220
```

```
Gly Lys Pro Gly Arg Pro Gly Glu Arg Gly Pro Pro Gly Pro Gln Gly
225                 230                 235                 240

Ala Arg Gly Leu Pro Gly Thr Ala Gly Leu Pro Gly Met Lys Gly His
            245                 250                 255

Arg Gly Phe Ser Gly Leu Asp Gly Ala Lys Gly Asp Thr Gly Pro Ala
            260                 265                 270

Gly Pro Lys Gly Glu Pro Gly Ser Pro Gly Glu Asn Gly Ala Pro Gly
            275                 280                 285

Gln Met Gly Pro Arg Gly Leu Pro Gly Glu Arg Gly Arg Pro Gly Pro
290                 295                 300

Pro Gly Ser Ala Gly Ala Arg Gly Asn Asp Gly Ala Val Gly Ala Ala
305                 310                 315                 320

Gly Pro Pro Gly Pro Thr Gly Pro Thr Gly Pro Pro Gly Phe Pro Gly
            325                 330                 335

Ala Ala Gly Ala Lys Gly Glu Ala Gly Pro Gln Gly Ala Arg Gly Ser
            340                 345                 350

Glu Gly Pro Gln Gly Val Arg Gly Glu Pro Gly Pro Pro Gly Pro Ala
            355                 360                 365

Gly Ala Ala Gly Pro Ala Gly Asn Pro Gly Ala Asp Gly Gln Pro Gly
            370                 375                 380

Ala Lys Gly Ala Asn Gly Ala Pro Gly Ile Ala Gly Ala Pro Gly Phe
385                 390                 395                 400

Pro Gly Ala Arg Gly Pro Ser Gly Pro Gln Gly Pro Ser Gly Ala Pro
            405                 410                 415

Gly Pro Lys Gly Asn Ser Gly Glu Pro Gly Ala Pro Gly Asn Lys Gly
            420                 425                 430

Asp Thr Gly Ala Lys Gly Glu Pro Gly Pro Ala Gly Val Gln Gly Pro
            435                 440                 445

Pro Gly Pro Ala Gly Glu Glu Gly Lys Arg Gly Ala Arg Gly Glu Pro
450                 455                 460

Gly Pro Ser Gly Leu Pro Gly Pro Pro Gly Glu Arg Gly Gly Pro Gly
465                 470                 475                 480

Ser Arg Gly Phe Pro Gly Ala Asp Gly Val Ala Gly Pro Lys Gly Pro
            485                 490                 495

Ala Gly Glu Arg Gly Ser Pro Gly Pro Ala Gly Pro Lys Gly Ser Pro
            500                 505                 510

Gly Glu Ala Gly Arg Pro Gly Glu Ala Gly Leu Pro Gly Ala Lys Gly
            515                 520                 525

Leu Thr Gly Ser Pro Gly Ser Pro Gly Pro Asp Gly Lys Thr Gly Pro
530                 535                 540

Pro Gly Pro Ala Gly Gln Asp Gly Arg Pro Gly Pro Ala Gly Pro Pro
545                 550                 555                 560

Gly Ala Arg Gly Gln Ala Gly Val Met Gly Phe Pro Gly Pro Lys Gly
            565                 570                 575

Thr Ala Gly Glu Pro Gly Lys Ala Gly Glu Arg Gly Val Pro Gly Pro
            580                 585                 590

Pro Gly Ala Val Gly Pro Ala Gly Lys Asp Gly Glu Ala Gly Ala Gln
            595                 600                 605

Gly Ala Pro Gly Pro Ala Gly Pro Ala Gly Glu Arg Gly Glu Gln Gly
            610                 615                 620

Pro Ala Gly Ser Pro Gly Phe Gln Gly Leu Pro Gly Pro Ala Gly Pro
625                 630                 635                 640

Pro Gly Glu Ala Gly Lys Pro Gly Glu Gln Gly Val Pro Gly Asp Leu
```

```
                    645                 650                 655
Gly Ala Pro Gly Pro Ser Gly Arg Gly Glu Arg Gly Phe Pro Gly
                660                 665                 670
Glu Arg Gly Val Gln Gly Pro Pro Gly Pro Ala Gly Pro Arg Gly Asn
            675                 680                 685
Asn Gly Ala Pro Gly Asn Asp Gly Ala Lys Gly Asp Thr Gly Ala Pro
        690                 695                 700
Gly Ala Pro Gly Ser Gln Gly Ala Pro Gly Leu Gln Gly Met Pro Gly
    705                 710                 715                 720
Glu Arg Gly Ala Ala Gly Leu Pro Gly Pro Lys Gly Asp Arg Gly Asp
                725                 730                 735
Ala Gly Pro Lys Gly Ala Asp Gly Ser Pro Gly Lys Asp Gly Val Arg
            740                 745                 750
Gly Leu Thr Gly Pro Ile Gly Pro Pro Gly Ala Gly Ala Pro Gly
        755                 760                 765
Asp Lys Gly Glu Thr Gly Pro Ser Gly Pro Ala Gly Pro Thr Gly Ala
    770                 775                 780
Arg Gly Ala Pro Gly Asp Arg Gly Glu Pro Gly Pro Pro Gly Pro Ala
785                 790                 795                 800
Gly Phe Ala Gly Pro Pro Gly Ala Asp Gly Gln Pro Gly Ala Lys Gly
                805                 810                 815
Glu Pro Gly Asp Thr Gly Val Lys Gly Asp Ala Gly Pro Pro Gly Pro
            820                 825                 830
Ala Gly Pro Ala Gly Pro Pro Gly Pro Ile Gly Asn Val Gly Ala Pro
        835                 840                 845
Gly Pro Lys Gly Ser Arg Gly Ala Ala Gly Pro Pro Gly Ala Thr Gly
    850                 855                 860
Phe Pro Gly Ala Ala Gly Arg Val Gly Pro Pro Gly Pro Ser Gly Asn
865                 870                 875                 880
Ala Gly Pro Pro Gly Pro Pro Gly Pro Val Gly Lys Glu Gly Gly Lys
                885                 890                 895
Gly Pro Arg Gly Glu Thr Gly Pro Ala Gly Arg Pro Gly Glu Val Gly
            900                 905                 910
Pro Pro Gly Pro Pro Gly Pro Ala Gly Glu Lys Gly Ser Pro Gly Ala
        915                 920                 925
Asp Gly Pro Ala Gly Ser Pro Gly Thr Pro Gly Pro Gln Gly Ile Ala
    930                 935                 940
Gly Gln Arg Gly Val Val Gly Leu Pro Gly Gln Arg Gly Glu Arg Gly
945                 950                 955                 960
Phe Pro Gly Leu Pro Gly Pro Ser Gly Glu Pro Gly Lys Gln Gly Pro
                965                 970                 975
Ser Gly Ala Ser Gly Glu Arg Gly Pro Pro Gly Pro Met Gly Pro Pro
            980                 985                 990
Gly Leu Ala Gly Pro Pro Gly Glu Ser Gly Arg Glu Gly Ser Pro Gly
        995                 1000                1005
Ala Glu Gly Ser Pro Gly Arg Asp Gly Ala Pro Gly Ala Lys Gly
        1010                1015                1020
Asp Arg Gly Glu Thr Gly Pro Ala Gly Pro Pro Gly Ala Pro Gly
        1025                1030                1035
Ala Pro Gly Ala Pro Gly Pro Val Gly Pro Ala Gly Lys Asn Gly
        1040                1045                1050
Asp Arg Gly Glu Thr Gly Pro Ala Gly Pro Ala Gly Pro Ile Gly
        1055                1060                1065
```

```
Pro Ala Gly Ala Arg Gly Pro Ala Gly Pro Gln Gly Pro Arg Gly
    1070            1075                1080

Asp Lys Gly Glu Thr Gly Glu Gln Gly Asp Arg Gly Ile Lys Gly
    1085            1090                1095

His Arg Gly Phe Ser Gly Leu Gln Gly Pro Pro Gly Ser Pro Gly
    1100            1105                1110

Ser Pro Gly Glu Gln Gly Pro Ser Gly Ala Ser Gly Pro Ala Gly
    1115            1120                1125

Pro Arg Gly Pro Pro Gly Ser Ala Gly Ser Pro Gly Lys Asp Gly
    1130            1135                1140

Leu Asn Gly Leu Pro Gly Pro Ile Gly Pro Pro Gly Pro Arg Gly
    1145            1150                1155

Arg Thr Gly Asp Ser Gly Pro Ala Gly Pro Pro Gly Pro Pro Gly
    1160            1165                1170

Pro Pro Gly Pro Pro Gly Pro Ser Gly Gly Tyr Asp Phe Ser
    1175            1180                1185

Phe Leu Pro Gln Pro Pro Gln Glu Lys Ser Gln Asp Gly Gly Arg
    1190            1195                1200

Tyr Tyr Arg Ala Asp Asp Ala Asn Val Val Arg Asp Arg Asp Leu
    1205            1210                1215

Glu Val Asp Thr Thr Leu Lys Ser Leu Ser Gln Gln Ile Glu Asn
    1220            1225                1230

Ile Arg Ser Pro Glu Gly Ser Arg Lys Asn Pro Ala Arg Thr Cys
    1235            1240                1245

Arg Asp Leu Lys Met Cys His Ser Asp Trp Lys Ser Gly Glu Tyr
    1250            1255                1260

Trp Ile Asp Pro Asn Gln Gly Cys Asn Leu Asp Ala Ile Lys Val
    1265            1270                1275

Tyr Cys Asn Met Glu Thr Gly Gln Thr Cys Val Phe Pro Thr Gln
    1280            1285                1290

Pro Ser Val Pro Gln Lys Asn Trp Tyr Ile Ser Pro Asn Pro Lys
    1295            1300                1305

Glu Lys Lys His Val Trp Phe Gly Glu Ser Met Thr Asp Gly Phe
    1310            1315                1320

Gln Phe Glu Tyr Gly Ser Glu Gly Ser Asp Pro Ala Asp Val Ala
    1325            1330                1335

Ile Gln Leu Thr Phe Leu Arg Leu Met Ser Thr Glu Ala Ser Gln
    1340            1345                1350

Asn Ile Thr Tyr His Cys Lys Asn Ser Val Ala Tyr Met Asp Gln
    1355            1360                1365

Gln Thr Gly Asn Leu Lys Lys Ser Leu Leu Leu Gln Gly Ser Asn
    1370            1375                1380

Glu Ile Glu Leu Arg Gly Glu Gly Asn Ser Arg Phe Thr Tyr Ser
    1385            1390                1395

Thr Leu Val Asp Gly Cys Thr Ser His Thr Gly Thr Trp Gly Lys
    1400            1405                1410

Thr Val Ile Glu Tyr Lys Thr Thr Lys Thr Ser Arg Leu Pro Ile
    1415            1420                1425

Ile Asp Val Ala Pro Leu Asp Ile Gly Ala Pro Asp Gln Glu Phe
    1430            1435                1440

Gly Met Asp Ile Gly Pro Ala Cys Phe Val
    1445            1450

<210> SEQ ID NO 42
```

```
<211> LENGTH: 1027
<212> TYPE: PRT
<213> ORGANISM: Rattus norvegicus

<400> SEQUENCE: 42

Met Thr Thr Thr Thr Lys Met Leu Gln Gly Ser Phe Ser Val Leu Leu
1               5                   10                  15

Leu Gly Gly Leu Leu Gly Val Leu His Ala Gln Gln Gln Glu Ala Ile
            20                  25                  30

Ser Pro Asp Ile Ser Thr Thr Asp Arg Asn Asn Cys Pro Glu Lys
        35                  40                  45

Ala Asp Cys Pro Val Asn Val Tyr Phe Val Leu Asp Thr Ser Glu Ser
    50                  55                  60

Val Ala Met Gln Ser Pro Thr Asp Ser Leu Leu Tyr His Met Gln Gln
65                  70                  75                  80

Phe Val Pro Gln Phe Ile Ser Gln Leu Gln Asn Glu Phe Tyr Leu Glu
                85                  90                  95

Gln Val Ala Leu Ser Trp Arg Tyr Gly Leu His Phe Ser Asp Gln
            100                 105                 110

Val Glu Val Phe Ser Pro Pro Gly Ser Asp Arg Ala Ser Phe Thr Lys
            115                 120                 125

Ser Leu Gln Gly Ile Arg Ser Phe Arg Arg Gly Thr Phe Thr Asp Cys
    130                 135                 140

Ala Leu Ala Asn Met Thr Gln Gln Ile Arg Gln His Val Gly Arg Gly
145                 150                 155                 160

Val Val Asn Phe Ala Val Val Ile Thr Asp Gly His Val Thr Gly Asn
                165                 170                 175

Pro Cys Gly Gly Ile Lys Met Gln Ala Glu Arg Ala Arg Glu Glu Gly
            180                 185                 190

Ile Arg Leu Phe Ala Val Ala Pro Asn Arg Asn Leu Asn Glu Gln Gly
        195                 200                 205

Leu Arg Asp Ile Ala Asn Thr Pro His Glu Leu Tyr Arg Asn Asn Tyr
    210                 215                 220

Ala Thr Met Arg Pro Asp Ser Thr Glu Ile Asp Gln Asp Thr Ile Asn
225                 230                 235                 240

Arg Ile Ile Lys Val Met Lys His Glu Ala Tyr Gly Glu Cys Tyr Lys
                245                 250                 255

Val Ser Cys Leu Glu Ile Pro Gly Pro His Gly Pro Lys Gly Tyr Arg
            260                 265                 270

Gly Gln Lys Gly Ala Lys Gly Asn Met Gly Glu Pro Gly Glu Pro Gly
        275                 280                 285

Gln Lys Gly Arg Gln Gly Asp Pro Gly Ile Glu Gly Pro Ile Gly Phe
    290                 295                 300

Pro Gly Pro Lys Gly Val Pro Gly Phe Lys Gly Glu Lys Gly Glu Phe
305                 310                 315                 320

Gly Ser Asp Gly Arg Lys Gly Ala Pro Gly Leu Ala Gly Lys Asn Gly
                325                 330                 335

Thr Asp Gly Gln Lys Gly Lys Leu Gly Arg Ile Gly Pro Pro Gly Cys
            340                 345                 350

Lys Gly Asp Pro Gly Ser Arg Gly Pro Asp Gly Tyr Pro Gly Glu Ala
        355                 360                 365

Gly Ser Pro Gly Glu Gln Gly Asp Gln Gly Ala Lys Gly Asp Ser Gly
    370                 375                 380

Arg Pro Gly Arg Arg Gly Pro Pro Gly Asn Pro Gly Asp Lys Gly Ser
385                 390                 395                 400
```

```
Lys Gly Tyr Arg Gly Asn Ser Gly Ala Pro Gly Ser Pro Gly Val Lys
                405                 410                 415
Gly Gly Lys Gly Gly Pro Gly Pro Arg Gly Pro Lys Gly Glu Pro Gly
            420                 425                 430
Arg Arg Gly Asp Pro Gly Thr Lys Gly Pro Gly Ser Asp Gly Pro
            435                 440                 445
Lys Gly Glu Lys Gly Asp Pro Gly Pro Glu Gly Pro Arg Gly Leu Ala
        450                 455                 460
Gly Glu Ile Gly Ser Lys Gly Ala Lys Gly Asp Arg Gly Leu Pro Gly
465                 470                 475                 480
Pro Arg Gly Pro Gln Gly Ala Leu Gly Glu Pro Gly Lys Gln Gly Ser
                485                 490                 495
Arg Gly Asp Pro Gly Asp Ala Gly Pro Arg Gly Asp Ser Gly Gln Pro
            500                 505                 510
Gly Pro Lys Gly Asp Pro Gly Arg Pro Gly Phe Ser Tyr Pro Gly Pro
        515                 520                 525
Arg Gly Thr Pro Gly Glu Lys Gly Glu Pro Gly Pro Pro Gly Pro Glu
    530                 535                 540
Gly Gly Arg Gly Asp Phe Gly Leu Lys Gly Ala Pro Gly Arg Lys Gly
545                 550                 555                 560
Glu Lys Gly Glu Pro Ala Asp Pro Gly Pro Pro Gly Glu Pro Gly Pro
                565                 570                 575
Arg Gly Pro Arg Gly Ile Pro Gly Pro Glu Gly Glu Pro Gly Pro Pro
            580                 585                 590
Gly Asp Pro Gly Leu Thr Glu Cys Asp Val Met Thr Tyr Val Arg Glu
        595                 600                 605
Thr Cys Gly Cys Cys Asp Cys Glu Lys Arg Cys Gly Ala Leu Asp Val
    610                 615                 620
Val Phe Val Ile Asp Ser Ser Glu Ser Ile Gly Tyr Thr Asn Phe Thr
625                 630                 635                 640
Leu Glu Lys Asn Phe Val Ile Asn Val Val Asn Arg Leu Gly Ala Ile
                645                 650                 655
Ala Lys Asp Pro Lys Ser Glu Thr Gly Thr Arg Val Gly Val Val Gln
            660                 665                 670
Tyr Ser His Glu Gly Thr Phe Glu Ala Ile Arg Leu Asp Asp Glu Arg
        675                 680                 685
Val Asn Ser Leu Ser Ser Phe Lys Glu Ala Val Lys Asn Leu Glu Trp
    690                 695                 700
Ile Ala Gly Gly Thr Trp Thr Pro Ser Ala Leu Lys Phe Ala Tyr Asn
705                 710                 715                 720
Gln Leu Ile Lys Glu Ser Arg Arg Gln Lys Thr Arg Val Phe Ala Val
                725                 730                 735
Val Ile Thr Asp Gly Arg His Asp Pro Arg Asp Asp Asp Leu Asn Leu
            740                 745                 750
Arg Ala Leu Cys Asp Arg Asp Val Thr Val Thr Ala Ile Gly Ile Gly
        755                 760                 765
Asp Met Phe His Glu Thr His Glu Ser Glu Asn Leu Tyr Ser Ile Ala
    770                 775                 780
Cys Asp Lys Pro Gln Gln Val Arg Asn Met Thr Leu Phe Ser Asp Leu
785                 790                 795                 800
Val Ala Glu Lys Phe Ile Asp Asp Met Glu Asp Val Leu Cys Pro Asp
                805                 810                 815
Pro Gln Ile Val Cys Pro Glu Leu Pro Cys Gln Thr Glu Leu Tyr Val
```

-continued

```
                      820                 825                 830
Ala Gln Cys Thr Gln Arg Pro Val Asp Ile Val Phe Leu Leu Asp Gly
                835                 840                 845

Ser Glu Arg Leu Gly Glu Gln Asn Phe Tyr Lys Ala Arg Arg Phe Val
            850                 855                 860

Glu Glu Val Ser Arg Arg Leu Thr Leu Ala Arg Arg Asp Asp Asp Pro
865                 870                 875                 880

Leu Asn Ala Arg Met Ala Leu Gln Tyr Gly Ser Gln Asn Gln Gln
                885                 890                 895

Gln Val Ala Phe Pro Leu Thr Tyr Asn Val Thr Thr Ile His Glu Ala
            900                 905                 910

Leu Glu Arg Thr Thr Tyr Leu Asn Ser Phe Ser His Val Gly Thr Gly
            915                 920                 925

Ile Val His Ala Ile Asn Asn Val Arg Gly Ala Arg Gly Gly Ala
            930                 935                 940

Arg Arg His Ala Glu Leu Ser Phe Val Phe Leu Thr Asp Gly Val Thr
945                 950                 955                 960

Gly Asn Asp Ser Leu Glu Glu Ser Val His Ser Met Arg Lys Gln Asn
                965                 970                 975

Val Val Pro Thr Val Ala Val Gly Gly Asp Val Asp Met Asp Val
            980                 985                 990

Leu Thr Lys Ile Ser Leu Gly Asp  Arg Ala Ala Ile Phe  Arg Glu Lys
            995                 1000                1005

Asp Phe Asp Ser Leu Ala Gln  Pro Ser Phe Phe Asp  Arg Phe Ile
      1010                1015                1020

Arg Trp  Ile Cys
      1025

<210> SEQ ID NO 43
<211> LENGTH: 284
<212> TYPE: PRT
<213> ORGANISM: Macaca mulatta

<400> SEQUENCE: 43

Met Asp Ala Ile Lys Lys Lys Met Gln Met Leu Lys Leu Asp Lys Glu
1               5                   10                  15

Asn Ala Leu Asp Arg Ala Glu Gln Ala Glu Ala Asp Lys Lys Ala Ala
            20                  25                  30

Glu Asp Arg Ser Lys Gln Leu Glu Asp Glu Leu Val Ser Leu Gln Lys
        35                  40                  45

Lys Leu Lys Gly Thr Glu Asp Glu Leu Asp Lys Tyr Ser Glu Ala Leu
    50                  55                  60

Lys Asp Ala Gln Glu Lys Leu Glu Leu Ala Glu Lys Lys Ala Thr Asp
65                  70                  75                  80

Ala Glu Ala Asp Val Ala Ser Leu Asn Arg Arg Ile Gln Leu Val Glu
                85                  90                  95

Glu Glu Leu Asp Arg Ala Gln Glu Arg Leu Ala Thr Ala Leu Gln Lys
            100                 105                 110

Leu Glu Glu Ala Glu Lys Ala Ala Asp Glu Ser Glu Arg Gly Met Lys
        115                 120                 125

Val Ile Glu Ser Arg Ala Gln Lys Asp Glu Glu Lys Met Glu Ile Gln
    130                 135                 140

Glu Ile Gln Leu Lys Glu Ala Lys His Ile Ala Glu Asp Ala Asp Arg
145                 150                 155                 160

Lys Tyr Glu Glu Val Ala Arg Lys Leu Val Ile Ile Glu Ser Asp Leu
```

```
                     165                 170                 175
Glu Arg Ala Glu Glu Arg Ala Glu Leu Ser Glu Gly Gln Val Arg Gln
                180                 185                 190

Leu Glu Glu Gln Leu Arg Ile Met Asp Gln Thr Leu Lys Ala Leu Met
            195                 200                 205

Ala Ala Glu Asp Lys Tyr Ser Gln Lys Glu Asp Lys Tyr Glu Glu Glu
        210                 215                 220

Ile Lys Val Leu Ser Asp Lys Leu Lys Glu Ala Glu Thr Arg Ala Glu
225                 230                 235                 240

Phe Ala Glu Arg Ser Val Thr Lys Leu Glu Lys Ser Ile Asp Asp Leu
                245                 250                 255

Glu Asp Glu Leu Tyr Ala Gln Lys Leu Lys Tyr Lys Ala Ile Ser Glu
            260                 265                 270

Glu Leu Asp His Ala Leu Asn Asp Met Thr Ser Ile
        275                 280

<210> SEQ ID NO 44
<211> LENGTH: 166
<212> TYPE: PRT
<213> ORGANISM: Rattus norvegicus

<400> SEQUENCE: 44

Met Ser Pro Lys Lys Ala Lys Lys Arg Leu Glu Gly Gly Ser Ser Asn
1               5                   10                  15

Val Phe Ser Met Phe Glu Gln Thr Gln Ile Gln Glu Phe Lys Glu Ala
            20                  25                  30

Phe Thr Ile Met Asp Gln Asn Arg Asp Gly Phe Ile Asp Lys Asn Asp
        35                  40                  45

Leu Arg Asp Thr Phe Ala Ala Leu Gly Arg Val Asn Val Lys Asn Glu
    50                  55                  60

Glu Ile Asp Glu Met Ile Lys Glu Ala Pro Gly Pro Ile Asn Phe Thr
65                  70                  75                  80

Val Phe Leu Thr Met Phe Gly Glu Lys Leu Lys Gly Ala Asp Pro Glu
                85                  90                  95

Glu Thr Ile Leu Asn Ala Phe Lys Val Phe Asp Pro Glu Gly Lys Gly
            100                 105                 110

Ser Leu Lys Ala Asp Tyr Val Arg Glu Met Leu Thr Thr Gln Ala Glu
        115                 120                 125

Arg Phe Ser Lys Glu Glu Ile Asp Gln Met Phe Ala Ala Phe Pro Pro
    130                 135                 140

Asp Val Thr Gly Asn Leu Asp Tyr Lys Asn Leu Val His Ile Ile Thr
145                 150                 155                 160

His Gly Glu Glu Lys Asp
                165

<210> SEQ ID NO 45
<211> LENGTH: 199
<212> TYPE: PRT
<213> ORGANISM: Homo sapiens

<400> SEQUENCE: 45

Met Ala Asn Arg Gly Pro Ala Tyr Gly Leu Ser Arg Glu Val Gln Gln
1               5                   10                  15

Lys Ile Glu Lys Gln Tyr Asp Ala Asp Leu Glu Gln Ile Leu Ile Gln
            20                  25                  30

Trp Ile Thr Thr Gln Cys Arg Lys Asp Val Gly Arg Pro Gln Pro Gly
        35                  40                  45
```

```
Arg Glu Asn Phe Gln Asn Trp Leu Lys Asp Gly Thr Val Leu Cys Glu
    50                  55                  60

Leu Ile Asn Ala Gln Tyr Pro Glu Gly Gln Ala Pro Val Lys Lys Ile
65                  70                  75                  80

Gln Ala Ser Thr Met Ala Phe Lys Gln Met Glu Gln Ile Ser Gln Phe
                85                  90                  95

Leu Gln Ala Ala Glu Arg Tyr Gly Ile Asn Thr Thr Asp Ile Phe Gln
                100                 105                 110

Thr Val Asp Leu Trp Glu Gly Lys Asn Met Ala Cys Val Gln Arg Thr
                115                 120                 125

Leu Met Asn Leu Gly Gly Leu Ala Val Ala Arg Asp Asp Gly Leu Phe
    130                 135                 140

Ser Gly Asp Pro Asn Trp Phe Pro Lys Ser Lys Glu Asn Pro Arg
145                 150                 155                 160

Asn Phe Ser Asp Asn Gln Leu Gln Glu Gly Lys Asn Val Ile Gly Leu
                165                 170                 175

Gln Met Gly Thr Asn Arg Gly Ala Ser Gln Ala Gly Met Thr Gly Tyr
                180                 185                 190

Gly Met Pro Arg Gln Ile Leu
                195

<210> SEQ ID NO 46
<211> LENGTH: 299
<212> TYPE: PRT
<213> ORGANISM: Rattus norvegicus

<400> SEQUENCE: 46

Met Ser Asp Ala Glu Glu Val Val Glu Tyr Glu Glu Gln Glu
1               5                   10                  15

Glu Glu Asp Trp Ser Glu Glu Glu Asp Glu Gln Glu Glu Ala Val
                20                  25                  30

Glu Glu Glu Asp Gly Glu Ala Glu Pro Asp Pro Glu Gly Glu Ala Glu
            35                  40                  45

Ala Glu Glu Asp Lys Ala Glu Glu Val Gly Pro Asp Glu Glu Ala Arg
50                  55                  60

Asp Ala Glu Asp Gly Pro Val Glu Asp Ser Lys Pro Lys Pro Ser Arg
65                  70                  75                  80

Leu Phe Met Pro Asn Leu Val Pro Pro Lys Ile Pro Asp Gly Glu Arg
                85                  90                  95

Val Asp Phe Asp Asp Ile His Arg Lys Arg Met Glu Lys Asp Leu Asn
                100                 105                 110

Glu Leu Gln Thr Leu Ile Glu Ala His Phe Glu Asn Arg Lys Lys Glu
            115                 120                 125

Glu Glu Glu Leu Ile Ser Leu Lys Asp Arg Ile Glu Lys Arg Arg Ala
        130                 135                 140

Glu Arg Ala Glu Gln Gln Arg Ile Arg Asn Glu Arg Glu Lys Glu Arg
145                 150                 155                 160

Gln Asn Arg Leu Ala Glu Glu Arg Ala Arg Glu Glu Glu Glu Asn
                165                 170                 175

Arg Arg Lys Ala Glu Asp Glu Ala Arg Lys Lys Lys Ala Leu Ser Asn
                180                 185                 190

Met Met His Phe Gly Gly Tyr Ile Gln Lys Ala Gln Ala Glu Arg Lys
            195                 200                 205

Ser Gly Lys Arg Gln Thr Glu Arg Glu Lys Lys Lys Lys Ile Leu Ala
        210                 215                 220
```

```
Glu Arg Arg Lys Val Leu Ala Ile Asp His Leu Asn Glu Asp Gln Leu
225                 230                 235                 240

Arg Glu Lys Ala Lys Glu Leu Trp Gln Ser Ile His Asn Leu Glu Ala
            245                 250                 255

Glu Lys Phe Asp Leu Gln Glu Lys Phe Lys Gln Lys Tyr Glu Ile
        260                 265                 270

Asn Val Leu Arg Asn Arg Ile Asn Asp Asn Gln Lys Val Ser Lys Thr
            275                 280                 285

Arg Gly Lys Ala Lys Val Thr Gly Arg Trp Lys
    290                 295

<210> SEQ ID NO 47
<211> LENGTH: 864
<212> TYPE: PRT
<213> ORGANISM: Rattus norvegicus

<400> SEQUENCE: 47

Ala Val Pro Gln Pro Gly Val Leu Ile Leu Leu Leu Asn Leu Leu
1               5                   10                  15

His Pro Ala Gln Pro Gly Val Pro Gly Ala Val Pro Gly Gly Val
            20                  25                  30

Pro Gly Gly Leu Pro Gly Gly Val Pro Gly Gly Val Tyr Tyr Pro Gly
            35                  40                  45

Ala Gly Ile Gly Gly Gly Leu Gly Gly Ala Leu Gly Pro Gly Gly
50                  55                  60

Lys Pro Pro Lys Pro Gly Ala Gly Leu Leu Gly Ala Phe Gly Ala Gly
65                  70                  75                  80

Pro Gly Gly Leu Gly Gly Ala Gly Pro Gly Ala Gly Leu Ser Tyr Ala
                85                  90                  95

Ser Arg Pro Gly Gly Val Leu Val Pro Gly Gly Ala Gly Ala Ala
            100                 105                 110

Ala Ala Tyr Lys Ala Ala Ala Lys Ala Gly Ala Gly Leu Gly Gly Ile
        115                 120                 125

Gly Gly Val Pro Gly Gly Val Gly Val Gly Gly Val Pro Gly Ala Val
    130                 135                 140

Gly Val Gly Gly Val Pro Gly Ala Val Gly Ile Gly Gly Ile Gly
145                 150                 155                 160

Gly Leu Gly Val Ser Thr Gly Ala Val Val Pro Gln Leu Gly Ala Gly
                165                 170                 175

Val Gly Ala Gly Gly Lys Pro Gly Lys Val Pro Gly Val Gly Leu Pro
            180                 185                 190

Gly Val Tyr Pro Gly Gly Val Leu Pro Gly Thr Gly Ala Arg Phe Pro
        195                 200                 205

Gly Val Gly Val Leu Pro Gly Val Pro Thr Gly Thr Gly Val Lys Ala
    210                 215                 220

Lys Val Pro Gly Gly Gly Gly Ala Phe Ser Gly Ile Pro Gly Val
225                 230                 235                 240

Gly Pro Phe Gly Gly Gln Gln Pro Gly Val Pro Leu Gly Tyr Pro Ile
                245                 250                 255

Lys Ala Pro Lys Leu Pro Gly Gly Tyr Gly Leu Pro Tyr Thr Asn Gly
            260                 265                 270

Lys Leu Pro Tyr Gly Val Ala Gly Ala Gly Gly Lys Ala Gly Tyr Pro
        275                 280                 285

Thr Gly Thr Gly Val Gly Ser Gln Ala Ala Val Ala Ala Ala Lys Ala
    290                 295                 300
```

```
Ala Lys Tyr Ala Gly Ala Gly Gly Gly Val Leu Pro Val Gly
305                 310                 315                 320

Gly Gly Gly Ile Pro Gly Ala Gly Ala Ile Pro Gly Ile Gly Gly
            325                 330                 335

Ile Thr Gly Ala Gly Thr Pro Ala Ala Ala Ala Ala Lys Ala Ala
            340                 345                 350

Ala Lys Ala Ala Lys Tyr Gly Ala Ala Gly Leu Val Pro Gly Gly
                355                 360                 365

Pro Gly Val Arg Val Pro Gly Ala Gly Ile Pro Gly Val Gly Ile Pro
370                 375                 380

Gly Val Gly Gly Ile Pro Gly Val Gly Gly Ile Pro Gly Val Gly Gly
385                 390                 395                 400

Ile Pro Gly Val Gly Gly Pro Gly Ile Gly Pro Gly Ile Val Gly
            405                 410                 415

Gly Pro Gly Ala Val Ser Pro Ala Ala Ala Lys Ala Ala Ala Lys
            420                 425                 430

Ala Ala Lys Tyr Gly Ala Arg Gly Val Gly Ile Pro Thr Tyr Gly
            435                 440                 445

Val Gly Ala Gly Gly Phe Pro Gly Tyr Gly Val Gly Ala Gly Ala Gly
450                 455                 460

Leu Gly Gly Ala Ser Gln Ala Ala Ala Ala Ala Ala Ala Lys Ala
465                 470                 475                 480

Ala Lys Tyr Gly Ala Gly Gly Ala Gly Thr Leu Gly Gly Leu Val Pro
                485                 490                 495

Gly Ala Val Pro Gly Ala Leu Pro Gly Ala Val Pro Gly Ala Leu Pro
            500                 505                 510

Gly Ala Val Pro Gly Ala Leu Pro Gly Ala Val Pro Gly Val Pro Gly
            515                 520                 525

Thr Gly Gly Val Pro Gly Ala Gly Thr Pro Ala Ala Ala Ala Ala
530                 535                 540

Ala Ala Ala Lys Ala Ala Ala Lys Ala Gly Gln Tyr Gly Leu Gly Pro
545                 550                 555                 560

Gly Val Gly Gly Val Pro Gly Gly Val Gly Gly Leu Pro Gly
            565                 570                 575

Gly Val Gly Pro Gly Gly Val Thr Gly Ile Gly Thr Gly Pro Gly Thr
            580                 585                 590

Gly Leu Val Pro Gly Asp Leu Gly Ala Gly Thr Pro Ala Ala Ala
            595                 600                 605

Lys Ser Ala Ala Lys Ala Ala Ala Lys Ala Gln Tyr Arg Ala Ala Ala
610                 615                 620

Gly Leu Gly Ala Gly Val Pro Gly Leu Gly Val Gly Ala Gly Val Pro
625                 630                 635                 640

Gly Phe Gly Ala Gly Ala Gly Gly Phe Gly Ala Gly Ala Gly Val Pro
                645                 650                 655

Gly Phe Gly Ala Gly Ala Val Pro Gly Ser Leu Ala Ala Ser Lys Ala
            660                 665                 670

Ala Lys Tyr Gly Ala Ala Gly Gly Leu Gly Gly Pro Gly Gly Leu Gly
            675                 680                 685

Gly Pro Gly Gly Leu Gly Gly Pro Gly Gly Phe Gly Gly Pro Gly Gly
            690                 695                 700

Leu Gly Gly Val Pro Gly Gly Val Ala Gly Ala Pro Ala Ala Ala
705                 710                 715                 720

Ala Ala Ala Lys Ala Ala Ala Lys Ala Ala Gln Tyr Gly Leu Gly Gly
```

```
                            725                 730                 735
Ala Gly Gly Leu Gly Ala Gly Gly Leu Gly Ala Gly Gly Leu Gly Ala
                740                 745                 750
Gly Gly Leu Gly Ala Gly Gly Leu Gly Ala Gly Gly Leu Gly Ala Gly
                755                 760                 765
Gly Val Ile Pro Gly Ala Val Gly Leu Gly Gly Val Ser Pro Ala Ala
                770                 775                 780
Ala Ala Lys Ala Ala Lys Tyr Gly Ala Ala Gly Leu Gly Gly Val Leu
785                 790                 795                 800
Gly Ala Arg Pro Phe Pro Gly Gly Val Ala Ala Arg Pro Gly Phe
                805                 810                 815
Gly Leu Ser Pro Ile Tyr Pro Gly Gly Ala Gly Gly Leu Gly Val
                820                 825                 830
Gly Gly Lys Pro Pro Lys Pro Tyr Gly Gly Ala Leu Gly Ala Leu Gly
                835                 840                 845
Tyr Gln Gly Gly Gly Cys Phe Gly Lys Ser Cys Gly Arg Lys Arg Lys
                850                 855                 860

<210> SEQ ID NO 48
<211> LENGTH: 312
<212> TYPE: PRT
<213> ORGANISM: Rattus norvegicus

<400> SEQUENCE: 48

Met Lys Ala Leu Trp Ala Leu Leu Leu Val Pro Leu Leu Thr Gly Cys
1               5                   10                  15
Leu Ala Glu Gly Glu Leu Glu Val Thr Asp Gln Leu Pro Gly Gln Ser
                20                  25                  30
Asp Gln Pro Trp Glu Gln Ala Leu Asn Arg Phe Trp Asp Tyr Leu Arg
                35                  40                  45
Trp Val Gln Thr Leu Ser Asp Gln Val Gln Glu Glu Leu Gln Ser Ser
                50                  55                  60
Gln Val Thr Gln Glu Leu Thr Val Leu Met Glu Asp Thr Met Thr Glu
65                  70                  75                  80
Val Lys Ala Tyr Lys Lys Glu Leu Glu Glu Gln Leu Gly Pro Val Ala
                85                  90                  95
Glu Glu Thr Arg Ala Arg Leu Ala Lys Glu Val Gln Ala Ala Gln Ala
                100                 105                 110
Arg Leu Gly Ala Asp Met Glu Asp Leu Arg Asn Arg Leu Gly Gln Tyr
                115                 120                 125
Arg Asn Glu Val Asn Thr Met Leu Gly Gln Ser Thr Glu Glu Leu Arg
130                 135                 140
Ser Arg Leu Ser Thr His Leu Arg Lys Met Arg Lys Arg Leu Met Arg
145                 150                 155                 160
Asp Ala Asp Asp Leu Gln Lys Arg Leu Ala Val Tyr Lys Ala Gly Ala
                165                 170                 175
Gln Glu Gly Ala Glu Arg Gly Val Ser Ala Ile Arg Glu Arg Leu Gly
                180                 185                 190
Pro Leu Val Glu Gln Gly Arg Gln Arg Thr Ala Asn Leu Gly Ala Gly
                195                 200                 205
Ala Ala Gln Pro Leu Arg Asp Arg Ala Gln Ala Leu Ser Asp Arg Ile
                210                 215                 220
Arg Gly Arg Leu Glu Glu Val Gly Asn Gln Ala Arg Asp Arg Leu Glu
225                 230                 235                 240
Glu Val Arg Glu Gln Met Glu Glu Val Arg Ser Lys Met Glu Glu Gln
```

```
                    245                 250                 255
Thr Gln Gln Ile Arg Leu Gln Ala Glu Ile Phe Gln Ala Arg Ile Lys
                260                 265                 270

Gly Trp Phe Glu Pro Leu Val Glu Asp Met Gln Arg Gln Trp Ala Asn
            275                 280                 285

Leu Met Glu Lys Ile Gln Ala Ser Val Ala Thr Asn Ser Ile Ala Ser
        290                 295                 300

Thr Thr Val Pro Leu Glu Asn Gln
305                 310

<210> SEQ ID NO 49
<211> LENGTH: 185
<212> TYPE: PRT
<213> ORGANISM: Rattus norvegicus

<400> SEQUENCE: 49

Met Lys Leu Val Ser Ile Ala Leu Met Leu Leu Gly Ser Leu Ala Val
1               5                   10                  15

Leu Gly Ala Asp Thr Ala Arg Leu Asp Thr Ser Ser Gln Phe Arg Lys
            20                  25                  30

Lys Trp Asn Lys Trp Ala Leu Ser Arg Gly Lys Arg Glu Leu Gln Ala
        35                  40                  45

Ser Ser Ser Tyr Pro Thr Gly Leu Val Asp Glu Lys Thr Val Pro Thr
    50                  55                  60

Gln Thr Leu Gly Leu Gln Asp Lys Gln Ser Thr Ser Thr Pro Gln
65                  70                  75                  80

Ala Ser Thr Gln Ser Thr Ala His Ile Arg Val Lys Arg Tyr Arg Gln
                85                  90                  95

Ser Met Asn Gln Gly Ser Arg Ser Thr Gly Cys Arg Phe Gly Thr Cys
            100                 105                 110

Thr Met Gln Lys Leu Ala His Gln Ile Tyr Gln Phe Thr Asp Lys Asp
        115                 120                 125

Lys Asp Gly Met Ala Pro Arg Asn Lys Ile Ser Pro Gln Gly Tyr Gly
    130                 135                 140

Arg Arg Arg Arg Arg Ser Leu Pro Glu Val Leu Arg Ala Arg Thr Val
145                 150                 155                 160

Glu Ser Ser Gln Glu Gln Thr His Ser Ala Pro Ala Ser Pro Ala His
                165                 170                 175

Gln Asp Ile Ser Arg Val Ser Arg Leu
            180                 185

<210> SEQ ID NO 50
<211> LENGTH: 1025
<212> TYPE: PRT
<213> ORGANISM: Mus musculus

<400> SEQUENCE: 50

Met Arg Leu Ala His Ala Leu Leu Pro Leu Leu Leu Gln Ala Cys Trp
1               5                   10                  15

Val Ala Thr Gln Asp Ile Gln Gly Ser Lys Ala Ile Ala Phe Gln Asp
            20                  25                  30

Cys Pro Val Asp Leu Phe Phe Val Leu Asp Thr Ser Glu Ser Val Ala
        35                  40                  45

Leu Arg Leu Lys Pro Tyr Gly Ala Leu Val Asp Lys Val Lys Ser Phe
    50                  55                  60

Thr Lys Arg Phe Ile Asp Asn Leu Arg Asp Arg Tyr Tyr Arg Cys Asp
65                  70                  75                  80
```

-continued

```
Arg Asn Leu Val Trp Asn Ala Gly Ala Leu His Tyr Ser Asp Glu Val
             85                  90                  95
Glu Ile Ile Arg Gly Leu Thr Arg Met Pro Ser Gly Arg Asp Glu Leu
            100                 105                 110
Lys Ala Ser Val Asp Ala Val Lys Tyr Phe Gly Lys Gly Thr Tyr Thr
        115                 120                 125
Asp Cys Ala Ile Lys Lys Gly Leu Glu Glu Leu Leu Ile Gly Gly Ser
    130                 135                 140
His Leu Lys Glu Asn Lys Tyr Leu Ile Val Val Thr Asp Gly His Pro
145                 150                 155                 160
Leu Glu Gly Tyr Lys Glu Pro Cys Gly Gly Leu Glu Asp Ala Val Asn
                165                 170                 175
Glu Ala Lys His Leu Gly Ile Lys Val Phe Ser Val Ala Ile Thr Pro
            180                 185                 190
Asp His Leu Glu Pro Arg Leu Ser Ile Ile Ala Thr Asp His Thr Tyr
        195                 200                 205
Arg Arg Asn Phe Thr Ala Ala Asp Trp Gly His Ser Arg Asp Ala Glu
    210                 215                 220
Glu Val Ile Ser Gln Thr Ile Asp Thr Ile Val Asp Met Ile Lys Asn
225                 230                 235                 240
Asn Val Glu Gln Val Cys Cys Ser Phe Glu Cys Gln Ala Ala Arg Gly
                245                 250                 255
Pro Pro Gly Pro Arg Gly Asp Pro Gly Tyr Glu Gly Glu Arg Gly Lys
            260                 265                 270
Pro Gly Leu Pro Gly Glu Lys Gly Glu Ala Gly Asp Pro Gly Arg Pro
        275                 280                 285
Gly Asp Leu Gly Pro Val Gly Tyr Gln Gly Met Lys Gly Glu Lys Gly
    290                 295                 300
Ser Arg Gly Glu Lys Gly Ser Arg Gly Pro Lys Gly Tyr Lys Gly Glu
305                 310                 315                 320
Lys Gly Lys Arg Gly Ile Asp Gly Val Asp Gly Met Lys Gly Glu Thr
                325                 330                 335
Gly Tyr Pro Gly Leu Pro Gly Cys Lys Gly Ser Pro Gly Phe Asp Gly
            340                 345                 350
Ile Gln Gly Pro Pro Gly Pro Lys Gly Asp Ala Gly Ala Phe Gly Met
        355                 360                 365
Lys Gly Glu Lys Gly Glu Ala Gly Ala Asp Gly Glu Ala Gly Arg Pro
    370                 375                 380
Gly Asn Ser Gly Ser Pro Gly Asp Glu Gly Asp Pro Gly Glu Pro Gly
385                 390                 395                 400
Pro Pro Gly Glu Lys Gly Glu Ala Gly Asp Glu Gly Asn Ala Gly Pro
                405                 410                 415
Asp Gly Ala Pro Gly Glu Arg Gly Gly Pro Gly Glu Arg Gly Pro Arg
            420                 425                 430
Gly Thr Pro Gly Val Arg Gly Pro Arg Gly Asp Pro Gly Glu Ala Gly
        435                 440                 445
Pro Gln Gly Asp Gln Gly Arg Glu Gly Pro Val Gly Ile Pro Gly Asp
    450                 455                 460
Ser Gly Glu Ala Gly Pro Ile Gly Pro Lys Gly Tyr Arg Gly Asp Glu
465                 470                 475                 480
Gly Pro Pro Gly Pro Glu Gly Leu Arg Gly Ala Pro Gly Pro Val Gly
                485                 490                 495
Pro Pro Gly Asp Pro Gly Leu Met Gly Glu Arg Gly Glu Asp Gly Pro
```

-continued

```
            500                 505                 510
Pro Gly Asn Gly Thr Glu Gly Phe Pro Gly Phe Pro Gly Tyr Pro Gly
            515                 520                 525

Asn Arg Gly Pro Pro Gly Leu Asn Gly Thr Lys Gly Tyr Pro Gly Leu
        530                 535                 540

Lys Gly Asp Glu Gly Glu Val Gly Asp Pro Gly Glu Asp Asn Asn Asp
545                 550                 555                 560

Ile Ser Pro Arg Gly Val Lys Gly Ala Lys Gly Tyr Arg Gly Pro Glu
                565                 570                 575

Gly Pro Gln Gly Pro Pro Gly His Val Gly Pro Pro Gly Pro Asp Glu
            580                 585                 590

Cys Glu Ile Leu Asp Ile Ile Met Lys Met Cys Ser Cys Cys Glu Cys
                595                 600                 605

Thr Cys Gly Pro Ile Asp Ile Leu Phe Val Leu Asp Ser Ser Glu Ser
        610                 615                 620

Ile Gly Leu Gln Asn Phe Glu Ile Ala Lys Asp Phe Ile Ile Lys Val
625                 630                 635                 640

Ile Asp Arg Leu Ser Lys Asp Glu Leu Val Lys Phe Glu Pro Gly Gln
                645                 650                 655

Ser His Ala Gly Val Val Gln Tyr Ser His Asn Gln Met Gln Glu His
            660                 665                 670

Val Asp Met Arg Ser Pro Asn Val Arg Asn Ala Gln Asp Phe Lys Glu
                675                 680                 685

Ala Val Lys Lys Leu Gln Trp Met Ala Gly Gly Thr Phe Thr Gly Glu
        690                 695                 700

Ala Leu Gln Tyr Thr Arg Asp Arg Leu Leu Pro Pro Thr Gln Asn Asn
705                 710                 715                 720

Arg Ile Ala Leu Val Ile Thr Asp Gly Arg Ser Asp Thr Gln Arg Asp
                725                 730                 735

Thr Thr Pro Leu Ser Val Leu Cys Gly Ala Asp Ile Gln Val Val Ser
            740                 745                 750

Val Gly Ile Lys Asp Val Phe Gly Phe Val Ala Gly Ser Asp Gln Leu
        755                 760                 765

Asn Val Ile Ser Cys Gln Gly Leu Ser Gln Gly Arg Pro Gly Ile Ser
770                 775                 780

Leu Val Lys Glu Asn Tyr Ala Glu Leu Leu Asp Asp Gly Phe Leu Lys
785                 790                 795                 800

Asn Ile Thr Ala Gln Ile Cys Ile Asp Lys Lys Cys Pro Asp Tyr Thr
                805                 810                 815

Cys Pro Ile Thr Phe Ser Ser Pro Ala Asp Ile Thr Ile Leu Leu Asp
            820                 825                 830

Ser Ser Ala Ser Val Gly Ser His Asn Phe Glu Thr Lys Val Phe
        835                 840                 845

Ala Lys Arg Leu Ala Glu Arg Phe Leu Ser Ala Gly Arg Ala Asp Pro
        850                 855                 860

Ser Gln Asp Val Arg Val Ala Val Val Gln Tyr Ser Gly Gln Gly Gln
865                 870                 875                 880

Gln Gln Pro Gly Arg Ala Ala Leu Gln Phe Leu Gln Asn Tyr Thr Val
                885                 890                 895

Leu Ala Ser Ser Val Asp Ser Met Asp Phe Ile Asn Asp Ala Thr Asp
            900                 905                 910

Val Asn Asp Ala Leu Ser Tyr Val Thr Arg Phe Tyr Arg Glu Ala Ser
        915                 920                 925
```

```
Ser Gly Ala Thr Lys Lys Arg Val Leu Leu Phe Ser Asp Gly Asn Ser
    930                 935                 940

Gln Gly Ala Thr Ala Glu Ala Ile Glu Lys Ala Val Gln Glu Ala Gln
945                 950                 955                 960

Arg Ala Gly Ile Glu Ile Phe Val Val Val Gly Pro Gln Val Asn
                965                 970                 975

Glu Pro His Ile Arg Val Leu Val Thr Gly Lys Thr Ala Glu Tyr Asp
            980                 985                 990

Val Ala Phe Gly Glu Arg His Leu Phe Arg Val Pro Asn Tyr Gln Ala
        995                 1000                1005

Leu Leu Arg Gly Val Leu Tyr Gln Thr Val Ser Arg Lys Val Ala
    1010                1015                1020

Leu Gly
    1025

<210> SEQ ID NO 51
<211> LENGTH: 317
<212> TYPE: PRT
<213> ORGANISM: Homo sapiens

<400> SEQUENCE: 51

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270
```

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
        290                 295                 300

Val Gly Thr Ser Ala Ala Pro Val Pro Ser Asp Asn His
305                 310                 315

<210> SEQ ID NO 52
<211> LENGTH: 151
<212> TYPE: PRT
<213> ORGANISM: Homo sapiens

<400> SEQUENCE: 52

Met Ser Ser Phe Ser Thr Thr Val Ser Phe Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45

Glu Lys Met Pro Leu Glu Asp Glu Val Val Pro Pro Gln Val Leu Ser
50                  55                  60

Glu Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
130                 135                 140

Gly Cys Asn Ser Phe Arg Tyr
145                 150

<210> SEQ ID NO 53
<211> LENGTH: 151
<212> TYPE: PRT
<213> ORGANISM: Homo sapiens

<400> SEQUENCE: 53

Met Ser Ser Phe Ser Thr Thr Val Ser Phe Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45

Glu Lys Met Pro Leu Glu Asp Glu Val Val Pro Pro Gln Val Leu Ser
50                  55                  60

Glu Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu

```
                130               135               140
Gly Cys Asn Ser Phe Arg Tyr
145                 150

<210> SEQ ID NO 54
<211> LENGTH: 151
<212> TYPE: PRT
<213> ORGANISM: Homo sapiens

<400> SEQUENCE: 54

Met Ser Ser Phe Ser Thr Thr Val Ser Phe Leu Leu Leu Ala
1               5                   10                  15

Phe Gln Leu Leu Gly Gln Thr Arg Ala Asn Pro Met Tyr Asn Ala Val
                20                  25                  30

Ser Asn Ala Asp Leu Met Asp Phe Lys Asn Leu Leu Asp His Leu Glu
            35                  40                  45

Glu Lys Met Pro Leu Glu Asp Glu Val Val Pro Pro Gln Val Leu Ser
50                  55                  60

Glu Pro Asn Glu Glu Ala Gly Ala Ala Leu Ser Pro Leu Pro Glu Val
65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
130                 135                 140

Gly Cys Asn Ser Phe Arg Tyr
145                 150

<210> SEQ ID NO 55
<211> LENGTH: 185
<212> TYPE: PRT
<213> ORGANISM: Homo sapiens

<400> SEQUENCE: 55

Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
                20                  25                  30

Lys Trp Asn Lys Trp Ala Leu Ser Arg Gly Lys Arg Glu Leu Arg Met
            35                  40                  45

Ser Ser Ser Tyr Pro Thr Gly Leu Ala Asp Val Lys Ala Gly Pro Ala
50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Arg Ser Lys Ile Ser Pro Gln
130                 135                 140

Gly Tyr Gly Arg Arg Arg Arg Ser Leu Pro Glu Ala Gly Pro Gly
145                 150                 155                 160
```

```
Arg Thr Leu Val Ser Ser Lys Pro Gln Ala His Gly Ala Pro Ala Pro
                165                 170                 175

Pro Ser Gly Ser Ala Pro His Phe Leu
            180                 185

<210> SEQ ID NO 56
<211> LENGTH: 227
<212> TYPE: PRT
<213> ORGANISM: Homo sapiens

<400> SEQUENCE: 56

Met Gly Gly Lys Leu Ser Lys Lys Lys Gly Tyr Asn Val Asn Asp
1               5                   10                  15

Glu Lys Ala Lys Glu Lys Asp Lys Lys Ala Glu Gly Ala Ala Thr Glu
                20                  25                  30

Glu Glu Gly Thr Pro Lys Glu Ser Glu Pro Gln Ala Ala Ala Glu Pro
            35                  40                  45

Ala Glu Ala Lys Glu Gly Lys Glu Lys Pro Asp Gln Asp Ala Glu Gly
        50                  55                  60

Lys Ala Glu Glu Lys Glu Gly Glu Lys Asp Ala Ala Ala Ala Lys Glu
65                  70                  75                  80

Glu Ala Pro Lys Ala Glu Pro Glu Lys Thr Glu Gly Ala Ala Glu Ala
                85                  90                  95

Lys Ala Glu Pro Pro Lys Ala Pro Glu Gln Glu Gln Ala Ala Pro Gly
            100                 105                 110

Pro Ala Ala Gly Gly Glu Ala Pro Lys Ala Ala Glu Ala Ala Ala
        115                 120                 125

Pro Ala Glu Ser Ala Ala Pro Ala Ala Gly Glu Glu Pro Ser Lys Glu
    130                 135                 140

Glu Gly Glu Pro Lys Lys Thr Glu Ala Pro Ala Ala Pro Ala Ala Gln
145                 150                 155                 160

Glu Thr Lys Ser Asp Gly Ala Pro Ala Ser Asp Ser Lys Pro Gly Ser
                165                 170                 175

Ser Glu Ala Ala Pro Ser Ser Lys Glu Thr Pro Ala Ala Thr Glu Ala
            180                 185                 190

Pro Ser Ser Thr Pro Lys Ala Gln Gly Pro Ala Ala Ser Ala Glu Glu
        195                 200                 205

Pro Lys Pro Val Glu Ala Pro Ala Ala Asn Ser Asp Gln Thr Val Thr
    210                 215                 220

Val Lys Glu
225

<210> SEQ ID NO 57
<211> LENGTH: 339
<212> TYPE: PRT
<213> ORGANISM: Homo sapiens

<400> SEQUENCE: 57

Met Trp Gln Leu Trp Ala Ser Leu Cys Cys Leu Leu Val Leu Ala Asn
1               5                   10                  15

Ala Arg Ser Arg Pro Ser Phe His Pro Leu Ser Asp Glu Leu Val Asn
                20                  25                  30

Tyr Val Asn Lys Arg Asn Thr Thr Trp Gln Ala Gly His Asn Phe Tyr
            35                  40                  45

Asn Val Asp Met Ser Tyr Leu Lys Arg Leu Cys Gly Thr Phe Leu Gly
        50                  55                  60
```

-continued

```
Gly Pro Lys Pro Pro Gln Arg Val Met Phe Thr Glu Asp Leu Lys Leu
 65                  70                  75                  80

Pro Ala Ser Phe Asp Ala Arg Glu Gln Trp Pro Gln Cys Pro Thr Ile
                 85                  90                  95

Lys Glu Ile Arg Asp Gln Gly Ser Cys Gly Ser Cys Trp Ala Phe Gly
            100                 105                 110

Ala Val Glu Ala Ile Ser Asp Arg Ile Cys Ile His Thr Asn Ala His
        115                 120                 125

Val Ser Val Glu Val Ser Ala Glu Asp Leu Leu Thr Cys Cys Gly Ser
130                 135                 140

Met Cys Gly Asp Gly Cys Asn Gly Gly Tyr Pro Ala Glu Ala Trp Asn
145                 150                 155                 160

Phe Trp Thr Arg Lys Gly Leu Val Ser Gly Leu Tyr Glu Ser His
                165                 170                 175

Val Gly Cys Arg Pro Tyr Ser Ile Pro Pro Cys Glu His His Val Asn
            180                 185                 190

Gly Ser Arg Pro Pro Cys Thr Gly Glu Gly Asp Thr Pro Lys Cys Ser
        195                 200                 205

Lys Ile Cys Glu Pro Gly Tyr Ser Pro Thr Tyr Lys Gln Asp Lys His
    210                 215                 220

Tyr Gly Tyr Asn Ser Tyr Ser Val Ser Asn Ser Glu Lys Asp Ile Met
225                 230                 235                 240

Ala Glu Ile Tyr Lys Asn Gly Pro Val Glu Gly Ala Phe Ser Val Tyr
                245                 250                 255

Ser Asp Phe Leu Leu Tyr Lys Ser Gly Val Tyr Gln His Val Thr Gly
            260                 265                 270

Glu Met Met Gly Gly His Ala Ile Arg Ile Leu Gly Trp Gly Val Glu
        275                 280                 285

Asn Gly Thr Pro Tyr Trp Leu Val Ala Asn Ser Trp Asn Thr Asp Trp
    290                 295                 300

Gly Asp Asn Gly Phe Phe Lys Ile Leu Arg Gly Gln Asp His Cys Gly
305                 310                 315                 320

Ile Glu Ser Glu Val Val Ala Gly Ile Pro Arg Thr Asp Gln Tyr Trp
                325                 330                 335

Glu Lys Ile

<210> SEQ ID NO 58
<211> LENGTH: 1028
<212> TYPE: PRT
<213> ORGANISM: Homo sapiens

<400> SEQUENCE: 58

Met Arg Ala Ala Arg Ala Leu Leu Pro Leu Leu Leu Gln Ala Cys Trp
  1               5                  10                  15

Thr Ala Ala Gln Asp Glu Pro Glu Thr Pro Arg Ala Val Ala Phe Gln
                 20                  25                  30

Asp Cys Pro Val Asp Leu Phe Phe Val Leu Asp Thr Ser Glu Ser Val
            35                  40                  45

Ala Leu Arg Leu Lys Pro Tyr Gly Ala Leu Val Asp Lys Val Lys Ser
        50                  55                  60

Phe Thr Lys Arg Phe Ile Asp Asn Leu Arg Asp Arg Tyr Tyr Arg Cys
 65                  70                  75                  80

Asp Arg Asn Leu Val Trp Asn Ala Gly Ala Leu His Tyr Ser Asp Glu
                 85                  90                  95

Val Glu Ile Ile Gln Gly Leu Thr Arg Met Pro Gly Gly Arg Asp Ala
```

-continued

```
                100                 105                 110
Leu Lys Ser Ser Val Asp Ala Val Lys Tyr Phe Gly Lys Gly Thr Tyr
            115                 120                 125

Thr Asp Cys Ala Ile Lys Lys Gly Leu Glu Gln Leu Leu Val Gly Gly
        130                 135                 140

Ser His Leu Lys Glu Asn Lys Tyr Leu Ile Val Val Thr Asp Gly His
145                 150                 155                 160

Pro Leu Glu Gly Tyr Lys Glu Pro Cys Gly Gly Leu Glu Asp Ala Val
                165                 170                 175

Asn Glu Ala Lys His Leu Gly Val Lys Val Phe Ser Val Ala Ile Thr
            180                 185                 190

Pro Asp His Leu Glu Pro Arg Leu Ser Ile Ile Ala Thr Asp His Thr
        195                 200                 205

Tyr Arg Arg Asn Phe Thr Ala Ala Asp Trp Gly Gln Ser Arg Asp Ala
    210                 215                 220

Glu Glu Ala Ile Ser Gln Thr Ile Asp Thr Ile Val Asp Met Ile Lys
225                 230                 235                 240

Asn Asn Val Glu Gln Val Cys Cys Ser Phe Glu Cys Gln Pro Ala Arg
                245                 250                 255

Gly Pro Pro Gly Leu Arg Gly Asp Pro Gly Phe Glu Gly Glu Arg Gly
            260                 265                 270

Lys Pro Gly Leu Pro Gly Glu Lys Gly Glu Ala Gly Asp Pro Gly Arg
        275                 280                 285

Pro Gly Asp Leu Gly Pro Val Gly Tyr Gln Gly Met Lys Gly Glu Lys
    290                 295                 300

Gly Ser Arg Gly Glu Lys Gly Ser Arg Gly Pro Lys Gly Tyr Lys Gly
305                 310                 315                 320

Glu Lys Gly Lys Arg Gly Ile Asp Gly Val Asp Gly Val Lys Gly Glu
                325                 330                 335

Met Gly Tyr Pro Gly Leu Pro Gly Cys Lys Gly Ser Pro Gly Phe Asp
            340                 345                 350

Gly Ile Gln Gly Pro Pro Gly Pro Lys Gly Asp Pro Gly Ala Phe Gly
        355                 360                 365

Leu Lys Gly Glu Lys Gly Glu Pro Gly Ala Asp Gly Glu Ala Gly Arg
    370                 375                 380

Pro Gly Ser Ser Gly Pro Ser Gly Asp Glu Gly Gln Pro Gly Glu Pro
385                 390                 395                 400

Gly Pro Pro Gly Glu Lys Gly Glu Ala Gly Asp Glu Gly Asn Pro Gly
                405                 410                 415

Pro Asp Gly Ala Pro Gly Glu Arg Gly Gly Pro Gly Glu Arg Gly Pro
            420                 425                 430

Arg Gly Thr Pro Gly Thr Arg Gly Pro Arg Gly Asp Pro Gly Glu Ala
        435                 440                 445

Gly Pro Gln Gly Asp Gln Gly Arg Glu Gly Pro Val Gly Val Pro Gly
    450                 455                 460

Asp Pro Gly Glu Ala Gly Pro Ile Gly Pro Lys Gly Tyr Arg Gly Asp
465                 470                 475                 480

Glu Gly Pro Pro Gly Ser Glu Gly Ala Arg Gly Ala Pro Gly Pro Ala
                485                 490                 495

Gly Pro Pro Gly Asp Pro Gly Leu Met Gly Glu Arg Gly Glu Asp Gly
            500                 505                 510

Pro Ala Gly Asn Gly Thr Glu Gly Phe Pro Gly Phe Pro Gly Tyr Pro
        515                 520                 525
```

-continued

```
Gly Asn Arg Gly Ala Pro Gly Ile Asn Gly Thr Lys Gly Tyr Pro Gly
            530                 535                 540

Leu Lys Gly Asp Glu Gly Glu Ala Gly Asp Pro Gly Asp Asp Asn Asn
545                 550                 555                 560

Asp Ile Ala Pro Arg Gly Val Lys Gly Ala Lys Gly Tyr Arg Gly Pro
                565                 570                 575

Glu Gly Pro Gln Gly Pro Pro Gly His Gln Gly Pro Pro Gly Pro Asp
            580                 585                 590

Glu Cys Glu Ile Leu Asp Ile Ile Met Lys Met Cys Ser Cys Cys Glu
            595                 600                 605

Cys Lys Cys Gly Pro Ile Asp Leu Leu Phe Val Leu Asp Ser Ser Glu
            610                 615                 620

Ser Ile Gly Leu Gln Asn Phe Glu Ile Ala Lys Asp Phe Val Val Lys
625                 630                 635                 640

Val Ile Asp Arg Leu Ser Arg Asp Glu Leu Val Lys Phe Glu Pro Gly
                645                 650                 655

Gln Ser Tyr Ala Gly Val Val Gln Tyr Ser His Ser Gln Met Gln Glu
            660                 665                 670

His Val Ser Leu Arg Ser Pro Ser Ile Arg Asn Val Gln Glu Leu Lys
            675                 680                 685

Glu Ala Ile Lys Ser Leu Gln Trp Met Ala Gly Gly Thr Phe Thr Gly
690                 695                 700

Glu Ala Leu Gln Tyr Thr Arg Asp Gln Leu Leu Pro Pro Ser Pro Asn
705                 710                 715                 720

Asn Arg Ile Ala Leu Val Ile Thr Asp Gly Arg Ser Asp Thr Gln Arg
                725                 730                 735

Asp Thr Thr Pro Leu Asn Val Leu Cys Ser Pro Gly Ile Gln Val Val
            740                 745                 750

Ser Val Gly Ile Lys Asp Val Phe Asp Phe Ile Pro Gly Ser Asp Gln
            755                 760                 765

Leu Asn Val Ile Ser Cys Gln Gly Leu Ala Pro Ser Gln Gly Arg Pro
770                 775                 780

Gly Leu Ser Leu Val Lys Glu Asn Tyr Ala Glu Leu Leu Glu Asp Ala
785                 790                 795                 800

Phe Leu Lys Asn Val Thr Ala Gln Ile Cys Ile Asp Lys Lys Cys Pro
                805                 810                 815

Asp Tyr Thr Cys Pro Ile Thr Phe Ser Ser Pro Ala Asp Ile Thr Ile
            820                 825                 830

Leu Leu Asp Gly Ser Ala Ser Val Gly Ser His Asn Phe Asp Thr Thr
            835                 840                 845

Lys Arg Phe Ala Lys Arg Leu Ala Glu Arg Phe Leu Thr Ala Gly Arg
850                 855                 860

Thr Asp Pro Ala His Asp Val Arg Val Ala Val Val Gln Tyr Ser Gly
865                 870                 875                 880

Thr Gly Gln Gln Arg Pro Glu Arg Ala Ser Leu Gln Phe Leu Gln Asn
                885                 890                 895

Tyr Thr Ala Leu Ala Ser Ala Val Asp Ala Met Asp Phe Ile Asn Asp
            900                 905                 910

Ala Thr Asp Val Asn Asp Ala Leu Gly Tyr Val Thr Arg Phe Tyr Arg
            915                 920                 925

Glu Ala Ser Ser Gly Ala Ala Lys Lys Arg Leu Leu Leu Phe Ser Asp
930                 935                 940

Gly Asn Ser Gln Gly Ala Thr Pro Ala Ala Ile Glu Lys Ala Val Gln
945                 950                 955                 960
```

```
Glu Ala Gln Arg Ala Gly Ile Glu Ile Phe Val Val Val Gly Arg
                965                 970                 975

Gln Val Asn Glu Pro His Ile Arg Val Leu Val Thr Gly Lys Thr Ala
            980                 985                 990

Glu Tyr Asp Val Ala Tyr Gly Glu Ser His Leu Phe Arg Val Pro Ser
        995                1000                1005

Tyr Gln Ala Leu Leu Arg Gly Val Phe His Gln Thr Val Ser Arg
    1010                1015                1020

Lys Val Ala Leu Gly
    1025

<210> SEQ ID NO 59
<211> LENGTH: 349
<212> TYPE: PRT
<213> ORGANISM: Homo sapiens

<400> SEQUENCE: 59

Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
    290                 295                 300
```

```
Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
        325                 330                 335

Glu Ser Leu Tyr Tyr Arg Lys Met Tyr Gly Asp Met Ala
            340                 345

<210> SEQ ID NO 60
<211> LENGTH: 349
<212> TYPE: PRT
<213> ORGANISM: Homo sapiens

<400> SEQUENCE: 60

Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
                20                  25                  30

Cys Arg Cys Pro Asp Glu Pro Ala Pro Arg Cys Pro Ala Gly Val Ser
            35                  40                  45

Leu Val Leu Asp Gly Cys Gly Cys Cys Arg Val Cys Ala Lys Gln Leu
50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
                100                 105                 110

Gly Glu Ser Phe Gln Ser Ser Cys Lys Tyr Gln Cys Thr Cys Leu Asp
            115                 120                 125

Gly Ala Val Gly Cys Met Pro Leu Cys Ser Met Asp Val Arg Leu Pro
130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
        290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
        325                 330                 335
```

Glu Ser Leu Tyr Tyr Arg Lys Met Tyr Gly Asp Met Ala
                340                 345

<210> SEQ ID NO 61
<211> LENGTH: 349
<212> TYPE: PRT
<213> ORGANISM: Homo sapiens

<400> SEQUENCE: 61

Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
    290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
            340                 345

<210> SEQ ID NO 62

```
<211> LENGTH: 149
<212> TYPE: PRT
<213> ORGANISM: Homo sapiens

<400> SEQUENCE: 62

Met Ala Arg Ser Asn Leu Pro Leu Ala Leu Gly Leu Ala Leu Val Ala
1               5                   10                  15

Phe Cys Leu Leu Ala Leu Pro Arg Asp Ala Arg Ala Arg Pro Gln Glu
            20                  25                  30

Arg Met Val Gly Glu Leu Arg Asp Leu Ser Pro Asp Pro Gln Val
        35                  40                  45

Gln Lys Ala Ala Gln Ala Ala Val Ala Ser Tyr Asn Met Gly Ser Asn
 50                  55                  60

Ser Ile Tyr Tyr Phe Arg Asp Thr His Ile Ile Lys Ala Gln Ser Gln
65                  70                  75                  80

Leu Val Ala Gly Ile Lys Tyr Phe Leu Thr Met Glu Met Gly Ser Thr
                85                  90                  95

Asp Cys Arg Lys Thr Arg Val Thr Gly Asp His Val Asp Leu Thr Thr
            100                 105                 110

Cys Pro Leu Ala Ala Gly Ala Gln Gln Glu Lys Leu Arg Cys Asp Phe
        115                 120                 125

Glu Val Leu Val Val Pro Trp Gln Asn Ser Ser Gln Leu Leu Lys His
130                 135                 140

Asn Cys Val Gln Met
145

<210> SEQ ID NO 63
<211> LENGTH: 350
<212> TYPE: PRT
<213> ORGANISM: Homo sapiens

<400> SEQUENCE: 63

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30

Lys Pro Gly Pro Ala Leu Ser Tyr Pro Gln Glu Glu Ala Thr Leu Asn
        35                  40                  45

Glu Met Phe Arg Glu Val Glu Glu Leu Met Glu Asp Thr Gln His Lys
 50                  55                  60

Leu Arg Ser Ala Val Glu Glu Met Glu Ala Glu Ala Ala Ala Ala Lys
65                  70                  75                  80

Ala Ser Ser Glu Val Asn Leu Ala Asn Leu Pro Pro Ser Tyr His Asn
                85                  90                  95

Glu Thr Asn Thr Asp Thr Lys Val Gly Asn Asn Thr Ile His Val His
            100                 105                 110

Arg Glu Ile His Lys Ile Thr Asn Asn Gln Thr Gly Gln Met Val Phe
        115                 120                 125

Ser Glu Thr Val Ile Thr Ser Val Gly Asp Glu Glu Gly Arg Arg Ser
130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190
```

```
Gly His Cys Thr Lys Met Ala Thr Arg Gly Ser Asn Gly Thr Ile Cys
        195                 200                 205

Asp Asn Gln Arg Asp Cys Pro Gly Leu Cys Cys Ala Phe Gln Arg
    210                 215                 220

Gly Leu Leu Phe Pro Val Cys Thr Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
            260                 265                 270

Cys Gln Pro His Ser His Ser Leu Val Tyr Val Cys Lys Pro Thr Phe
        275                 280                 285

Val Gly Ser Arg Asp Gln Asp Gly Glu Ile Leu Leu Pro Arg Glu Val
    290                 295                 300

Pro Asp Glu Tyr Glu Val Gly Ser Phe Met Glu Val Arg Gln Glu
305                 310                 315                 320

Leu Glu Asp Leu Glu Arg Ser Leu Thr Glu Glu Met Ala Leu Gly Glu
                325                 330                 335

Pro Ala Ala Ala Ala Ala Leu Leu Gly Gly Glu Glu Ile
            340                 345                 350

<210> SEQ ID NO 64
<211> LENGTH: 556
<212> TYPE: PRT
<213> ORGANISM: Homo sapiens

<400> SEQUENCE: 64

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220
```

```
Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
            245                 250                 255

Lys Ile Thr Asp Phe Gly Glu Pro Arg Ile Gln Gln Glu Glu Gly Gln
        260                 265                 270

Asn Gln Ser Phe Ser Asn Gly Leu Ala Cys Leu Asp Met Val Leu Arg
    275                 280                 285

Ile Ala Asp Val Lys Glu Asp Leu Leu Leu Gln Tyr Asp Cys Leu
290                 295                 300

Ala Leu Asn Leu His Gly Leu Arg Arg His Thr Val Arg Leu Ser Arg
305                 310                 315                 320

Lys Asn Pro Ile Asp His His Ser Ile Tyr Cys Ile Ile Ala Val Cys
            325                 330                 335

Ser Val Phe Leu Met Leu Ile Asn Val Leu Ile Ile Leu Lys Met
        340                 345                 350

Phe Trp Ile Glu Ala Thr Leu Leu Trp Arg Asp Ile Ala Lys Pro Tyr
            355                 360                 365

Lys Thr Arg Asn Asp Gly Lys Leu Tyr Asp Ala Tyr Val Val Tyr Pro
370                 375                 380

Arg Asn Tyr Lys Ser Ser Thr Asp Gly Ala Ser Arg Val Glu His Phe
385                 390                 395                 400

Val His Gln Ile Leu Pro Asp Val Leu Glu Asn Lys Cys Gly Tyr Thr
            405                 410                 415

Leu Cys Ile Tyr Gly Arg Asp Met Leu Pro Gly Glu Asp Val Val Thr
            420                 425                 430

Ala Val Glu Thr Asn Ile Arg Lys Ser Arg Arg His Ile Phe Ile Leu
        435                 440                 445

Thr Pro Gln Ile Thr His Asn Lys Glu Phe Ala Tyr Glu Gln Glu Val
        450                 455                 460

Ala Leu His Cys Ala Leu Ile Gln Asn Asp Ala Lys Val Ile Leu Ile
465                 470                 475                 480

Glu Met Glu Ala Leu Ser Glu Leu Asp Met Leu Gln Ala Glu Ala Leu
            485                 490                 495

Gln Asp Ser Leu Gln His Leu Met Lys Val Gln Gly Thr Ile Lys Trp
        500                 505                 510

Arg Glu Asp His Ile Ala Asn Lys Arg Ser Leu Asn Ser Lys Phe Trp
        515                 520                 525

Lys His Val Arg Tyr Gln Met Pro Val Pro Ser Lys Ile Pro Arg Lys
530                 535                 540

Ala Ser Ser Leu Thr Pro Leu Ala Ala Gln Lys Gln
545                 550                 555

<210> SEQ ID NO 65
<211> LENGTH: 660
<212> TYPE: PRT
<213> ORGANISM: Homo sapiens

<400> SEQUENCE: 65

Met Glu Ala Leu Met Ala Arg Gly Ala Leu Thr Gly Pro Leu Arg Ala
1               5                   10                  15

Leu Cys Leu Leu Gly Cys Leu Leu Ser His Ala Ala Ala Ala Pro Ser
            20                  25                  30

Pro Ile Ile Lys Phe Pro Gly Asp Val Ala Pro Lys Thr Asp Lys Glu
        35                  40                  45
```

```
Leu Ala Val Gln Tyr Leu Asn Thr Phe Tyr Gly Cys Pro Lys Glu Ser
 50                  55                  60
Cys Asn Leu Phe Val Leu Lys Asp Thr Leu Lys Met Gln Lys Phe
 65                  70                  75                  80
Phe Gly Leu Pro Gln Thr Gly Asp Leu Asp Gln Asn Thr Ile Glu Thr
                     85                  90                  95
Met Arg Lys Pro Arg Cys Gly Asn Pro Asp Val Ala Asn Tyr Asn Phe
                100                 105                 110
Phe Pro Arg Lys Pro Lys Trp Asp Lys Asn Gln Ile Thr Tyr Arg Ile
                115                 120                 125
Ile Gly Tyr Thr Pro Asp Leu Asp Pro Glu Thr Val Asp Asp Ala Phe
130                 135                 140
Ala Arg Ala Phe Gln Val Trp Ser Asp Val Thr Pro Leu Arg Phe Ser
145                 150                 155                 160
Arg Ile His Asp Gly Glu Ala Asp Ile Met Ile Asn Phe Gly Arg Trp
                165                 170                 175
Glu His Gly Asp Gly Tyr Pro Phe Asp Gly Lys Asp Gly Leu Leu Ala
                180                 185                 190
His Ala Phe Ala Pro Gly Thr Gly Val Gly Gly Asp Ser His Phe Asp
                195                 200                 205
Asp Asp Glu Leu Trp Thr Leu Gly Glu Gly Gln Val Val Arg Val Lys
210                 215                 220
Tyr Gly Asn Ala Asp Gly Glu Tyr Cys Lys Phe Pro Phe Leu Phe Asn
225                 230                 235                 240
Gly Lys Glu Tyr Asn Ser Cys Thr Asp Thr Gly Arg Ser Asp Gly Phe
                245                 250                 255
Leu Trp Cys Ser Thr Thr Tyr Asn Phe Glu Lys Asp Gly Lys Tyr Gly
                260                 265                 270
Phe Cys Pro His Glu Ala Leu Phe Thr Met Gly Gly Asn Ala Glu Gly
                275                 280                 285
Gln Pro Cys Lys Phe Pro Phe Arg Phe Gln Gly Thr Ser Tyr Asp Ser
                290                 295                 300
Cys Thr Thr Glu Gly Arg Thr Asp Gly Tyr Arg Trp Cys Gly Thr Thr
305                 310                 315                 320
Glu Asp Tyr Asp Arg Asp Lys Lys Tyr Gly Phe Cys Pro Glu Thr Ala
                325                 330                 335
Met Ser Thr Val Gly Gly Asn Ser Glu Gly Ala Pro Cys Val Phe Pro
                340                 345                 350
Phe Thr Phe Leu Gly Asn Lys Tyr Glu Ser Cys Thr Ser Ala Gly Arg
                355                 360                 365
Ser Asp Gly Lys Met Trp Cys Ala Thr Ala Asn Tyr Asp Asp Asp
370                 375                 380
Arg Lys Trp Gly Phe Cys Pro Asp Gln Gly Tyr Ser Leu Phe Leu Val
385                 390                 395                 400
Ala Ala His Glu Phe Gly His Ala Met Gly Leu Glu His Ser Gln Asp
                405                 410                 415
Pro Gly Ala Leu Met Ala Pro Ile Tyr Thr Tyr Thr Lys Asn Phe Arg
                420                 425                 430
Leu Ser Gln Asp Asp Ile Lys Gly Ile Gln Glu Leu Tyr Gly Ala Ser
                435                 440                 445
Pro Asp Ile Asp Leu Gly Thr Gly Pro Thr Pro Thr Leu Gly Pro Val
                450                 455                 460
Thr Pro Glu Ile Cys Lys Gln Asp Ile Val Phe Asp Gly Ile Ala Gln
465                 470                 475                 480
```

```
Ile Arg Gly Glu Ile Phe Phe Lys Asp Arg Phe Ile Trp Arg Thr
                485                 490                 495

Val Thr Pro Arg Asp Lys Pro Met Gly Pro Leu Leu Val Ala Thr Phe
                500                 505                 510

Trp Pro Glu Leu Pro Glu Lys Ile Asp Ala Val Tyr Glu Ala Pro Gln
                515                 520                 525

Glu Glu Lys Ala Val Phe Phe Ala Gly Asn Tyr Trp Ile Tyr Ser
            530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
                565                 570                 575

Asn Lys Lys Thr Tyr Ile Phe Ala Gly Asp Lys Phe Trp Arg Tyr Asn
                580                 585                 590

Glu Val Lys Lys Lys Met Asp Pro Gly Phe Pro Lys Leu Ile Ala Asp
                595                 600                 605

Ala Trp Asn Ala Ile Pro Asp Asn Leu Asp Ala Val Val Asp Leu Gln
            610                 615                 620

Gly Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
                645                 650                 655

Trp Leu Gly Cys
            660

<210> SEQ ID NO 66
<211> LENGTH: 660
<212> TYPE: PRT
<213> ORGANISM: Homo sapiens

<400> SEQUENCE: 66

Met Glu Ala Leu Met Ala Arg Gly Ala Leu Thr Gly Pro Leu Arg Ala
1               5                   10                  15

Leu Cys Leu Leu Gly Cys Leu Leu Ser His Ala Ala Ala Pro Ser
            20                  25                  30

Pro Ile Ile Lys Phe Pro Gly Asp Val Ala Pro Lys Thr Asp Lys Glu
                35                  40                  45

Leu Ala Val Gln Tyr Leu Asn Thr Phe Tyr Gly Cys Pro Lys Glu Ser
            50                  55                  60

Cys Asn Leu Phe Val Leu Lys Asp Thr Leu Lys Lys Met Gln Lys Phe
65                  70                  75                  80

Phe Gly Leu Pro Gln Thr Gly Asp Leu Asp Gln Asn Thr Ile Glu Thr
                85                  90                  95

Met Arg Lys Pro Arg Cys Gly Asn Pro Asp Val Ala Asn Tyr Asn Phe
                100                 105                 110

Phe Pro Arg Lys Pro Lys Trp Asp Lys Asn Gln Ile Thr Tyr Arg Ile
            115                 120                 125

Ile Gly Tyr Thr Pro Asp Leu Asp Pro Glu Thr Val Asp Asp Ala Phe
            130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
                180                 185                 190
```

```
His Ala Phe Ala Pro Gly Thr Gly Val Gly Gly Asp Ser His Phe Asp
        195                 200                 205

Asp Asp Glu Leu Trp Thr Leu Gly Glu Gly Gln Val Val Arg Val Lys
        210                 215                 220

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
                245                 250                 255

Leu Trp Cys Ser Thr Thr Tyr Asn Phe Glu Lys Asp Gly Lys Tyr Gly
            260                 265                 270

Phe Cys Pro His Glu Ala Leu Phe Thr Met Gly Gly Asn Ala Glu Gly
        275                 280                 285

Gln Pro Cys Lys Phe Pro Phe Arg Phe Gln Gly Thr Ser Tyr Asp Ser
        290                 295                 300

Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
                325                 330                 335

Met Ser Thr Val Gly Gly Asn Ser Glu Gly Ala Pro Cys Val Phe Pro
            340                 345                 350

Phe Thr Phe Leu Gly Asn Lys Tyr Glu Ser Cys Thr Ser Ala Gly Arg
        355                 360                 365

Ser Asp Gly Lys Met Trp Cys Ala Thr Thr Ala Asn Tyr Asp Asp Asp
370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
                405                 410                 415

Pro Gly Ala Leu Met Ala Pro Ile Tyr Thr Tyr Thr Lys Asn Phe Arg
            420                 425                 430

Leu Ser Gln Asp Asp Ile Lys Gly Ile Gln Glu Leu Tyr Gly Ala Ser
        435                 440                 445

Pro Asp Ile Asp Leu Gly Thr Gly Pro Thr Pro Thr Leu Gly Pro Val
        450                 455                 460

Thr Pro Glu Ile Cys Lys Gln Asp Ile Val Phe Asp Gly Ile Ala Gln
465                 470                 475                 480

Ile Arg Gly Glu Ile Phe Phe Phe Lys Asp Arg Phe Ile Trp Arg Thr
                485                 490                 495

Val Thr Pro Arg Asp Lys Pro Met Gly Pro Leu Leu Val Ala Thr Phe
            500                 505                 510

Trp Pro Glu Leu Pro Glu Lys Ile Asp Ala Val Tyr Glu Ala Pro Gln
        515                 520                 525

Glu Glu Lys Ala Val Phe Phe Ala Gly Asn Glu Tyr Trp Ile Tyr Ser
        530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
                565                 570                 575

Asn Lys Lys Thr Tyr Ile Phe Ala Gly Asp Lys Phe Trp Arg Tyr Asn
            580                 585                 590

Glu Val Lys Lys Lys Met Asp Pro Gly Phe Pro Lys Leu Ile Ala Asp
        595                 600                 605

Ala Trp Asn Ala Ile Pro Asp Asn Leu Asp Ala Val Val Asp Leu Gln
```

-continued

```
                610                 615                 620
Gly Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
                645                 650                 655

Trp Leu Gly Cys
            660

<210> SEQ ID NO 67
<211> LENGTH: 660
<212> TYPE: PRT
<213> ORGANISM: Homo sapiens

<400> SEQUENCE: 67

Met Glu Ala Leu Met Ala Arg Gly Ala Leu Thr Gly Pro Leu Arg Ala
1               5                   10                  15

Leu Cys Leu Leu Gly Cys Leu Leu Ser His Ala Ala Ala Ala Pro Ser
                20                  25                  30

Pro Ile Ile Lys Phe Pro Gly Asp Val Ala Pro Lys Thr Asp Lys Glu
            35                  40                  45

Leu Ala Val Gln Tyr Leu Asn Thr Phe Tyr Gly Cys Pro Lys Glu Ser
50                  55                  60

Cys Asn Leu Phe Val Leu Lys Asp Thr Leu Lys Lys Met Gln Lys Phe
65                  70                  75                  80

Phe Gly Leu Pro Gln Thr Gly Asp Leu Asp Gln Asn Thr Ile Glu Thr
                85                  90                  95

Met Arg Lys Pro Arg Cys Gly Asn Pro Asp Val Ala Asn Tyr Asn Phe
            100                 105                 110

Phe Pro Arg Lys Pro Lys Trp Asp Lys Asn Gln Ile Thr Tyr Arg Ile
        115                 120                 125

Ile Gly Tyr Thr Pro Asp Leu Asp Pro Glu Thr Val Asp Asp Ala Phe
130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
            180                 185                 190

His Ala Phe Ala Pro Gly Thr Gly Val Gly Gly Asp Ser His Phe Asp
        195                 200                 205

Asp Asp Glu Leu Trp Thr Leu Gly Glu Gly Gln Val Val Arg Val Lys
210                 215                 220

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
                245                 250                 255

Leu Trp Cys Ser Thr Thr Tyr Asn Phe Glu Lys Asp Gly Lys Tyr Gly
            260                 265                 270

Phe Cys Pro His Glu Ala Leu Phe Thr Met Gly Gly Asn Ala Glu Gly
        275                 280                 285

Gln Pro Cys Lys Phe Pro Phe Arg Phe Gln Gly Thr Ser Tyr Asp Ser
            290                 295                 300

Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
```

```
                    325                 330                 335
Met Ser Thr Val Gly Gly Asn Ser Glu Gly Ala Pro Cys Val Phe Pro
                340                 345                 350

Phe Thr Phe Leu Gly Asn Lys Tyr Glu Ser Cys Thr Ser Ala Gly Arg
                355                 360                 365

Ser Asp Gly Lys Met Trp Cys Ala Thr Thr Ala Asn Tyr Asp Asp Asp
            370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
                405                 410                 415

Pro Gly Ala Leu Met Ala Pro Ile Tyr Thr Tyr Thr Lys Asn Phe Arg
                420                 425                 430

Leu Ser Gln Asp Asp Ile Lys Gly Ile Gln Glu Leu Tyr Gly Ala Ser
            435                 440                 445

Pro Asp Ile Asp Leu Gly Thr Gly Pro Thr Pro Thr Leu Gly Pro Val
        450                 455                 460

Thr Pro Glu Ile Cys Lys Gln Asp Ile Val Phe Asp Gly Ile Ala Gln
465                 470                 475                 480

Ile Arg Gly Glu Ile Phe Phe Phe Lys Asp Arg Phe Ile Trp Arg Thr
                485                 490                 495

Val Thr Pro Arg Asp Lys Pro Met Gly Pro Leu Leu Val Ala Thr Phe
                500                 505                 510

Trp Pro Glu Leu Pro Glu Lys Ile Asp Ala Val Tyr Glu Ala Pro Gln
            515                 520                 525

Glu Glu Lys Ala Val Phe Phe Ala Gly Asn Glu Tyr Trp Ile Tyr Ser
        530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
                565                 570                 575

Asn Lys Lys Thr Tyr Ile Phe Ala Gly Asp Lys Phe Trp Arg Tyr Asn
                580                 585                 590

Glu Val Lys Lys Lys Met Asp Pro Gly Phe Pro Lys Leu Ile Ala Asp
            595                 600                 605

Ala Trp Asn Ala Ile Pro Asp Asn Leu Asp Ala Val Val Asp Leu Gln
        610                 615                 620

Gly Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
                645                 650                 655

Trp Leu Gly Cys
            660

<210> SEQ ID NO 68
<211> LENGTH: 207
<212> TYPE: PRT
<213> ORGANISM: Homo sapiens

<400> SEQUENCE: 68

Met Ala Pro Phe Glu Pro Leu Ala Ser Gly Ile Leu Leu Leu Leu Trp
1               5                   10                  15

Leu Ile Ala Pro Ser Arg Ala Cys Thr Cys Val Pro Pro His Pro Gln
                20                  25                  30

Thr Ala Phe Cys Asn Ser Asp Leu Val Ile Arg Ala Lys Phe Val Gly
```

```
              35                  40                  45
Thr Pro Glu Val Asn Gln Thr Thr Leu Tyr Gln Arg Tyr Glu Ile Lys
 50                  55                  60

Met Thr Lys Met Tyr Lys Gly Phe Gln Ala Leu Gly Asp Ala Ala Asp
 65                  70                  75                  80

Ile Arg Phe Val Tyr Thr Pro Ala Met Glu Ser Val Cys Gly Tyr Phe
                 85                  90                  95

His Arg Ser His Asn Arg Ser Glu Glu Phe Leu Ile Ala Gly Lys Leu
                100                 105                 110

Gln Asp Gly Leu Leu His Ile Thr Thr Cys Ser Phe Val Ala Pro Trp
            115                 120                 125

Asn Ser Leu Ser Leu Ala Gln Arg Arg Gly Phe Thr Lys Thr Tyr Thr
        130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
        195                 200                 205

<210> SEQ ID NO 69
<211> LENGTH: 220
<212> TYPE: PRT
<213> ORGANISM: Homo sapiens

<400> SEQUENCE: 69

Met Gly Ala Ala Ala Arg Thr Leu Arg Leu Ala Leu Gly Leu Leu Leu
 1               5                  10                  15

Leu Ala Thr Leu Leu Arg Pro Ala Asp Ala Cys Ser Cys Ser Pro Val
                20                  25                  30

His Pro Gln Gln Ala Phe Cys Asn Ala Asp Val Val Ile Arg Ala Lys
            35                  40                  45

Ala Val Ser Glu Lys Glu Val Asp Ser Gly Asn Asp Ile Tyr Gly Asn
 50                  55                  60

Pro Ile Lys Arg Ile Gln Tyr Glu Ile Lys Gln Ile Lys Met Phe Lys
 65                  70                  75                  80

Gly Pro Glu Lys Asp Ile Glu Phe Ile Tyr Thr Ala Pro Ser Ser Ala
                85                  90                  95

Val Cys Gly Val Ser Leu Asp Val Gly Gly Lys Lys Glu Tyr Leu Ile
                100                 105                 110

Ala Gly Lys Ala Glu Gly Asp Gly Lys Met His Ile Thr Leu Cys Asp
            115                 120                 125

Phe Ile Val Pro Trp Asp Thr Leu Ser Thr Thr Gln Lys Lys Ser Leu
        130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
                180                 185                 190

Cys Ile Lys Arg Ser Asp Gly Ser Cys Ala Trp Tyr Arg Gly Ala Ala
            195                 200                 205

Pro Pro Lys Gln Glu Phe Leu Asp Ile Glu Asp Pro
```

<210> SEQ ID NO 70
<211> LENGTH: 298
<212> TYPE: PRT
<213> ORGANISM: Homo sapiens

<400> SEQUENCE: 70

Met Lys Thr Leu Gln Ser Thr Leu Leu Leu Leu Val Pro Leu
1               5                   10                  15

Ile Lys Pro Ala Pro Pro Thr Gln Gln Asp Ser Arg Ile Ile Tyr Asp
            20                  25                  30

Tyr Gly Thr Asp Asn Phe Glu Glu Ser Ile Phe Ser Gln Asp Tyr Glu
        35                  40                  45

Asp Lys Tyr Leu Asp Gly Lys Asn Ile Lys Glu Lys Glu Thr Val Ile
50                  55                  60

Ile Pro Asn Glu Lys Ser Leu Gln Leu Gln Lys Asp Glu Ala Ile Thr
65                  70                  75                  80

Pro Leu Pro Pro Lys Lys Glu Asn Asp Glu Met Pro Thr Cys Leu Leu
                85                  90                  95

Cys Val Cys Leu Ser Gly Ser Val Tyr Cys Glu Glu Val Asp Ile Asp
            100                 105                 110

Ala Val Pro Pro Leu Pro Lys Glu Ser Ala Tyr Leu Tyr Ala Arg Phe
        115                 120                 125

Asn Lys Ile Lys Lys Leu Thr Ala Lys Asp Phe Ala Asp Ile Pro Asn
        130                 135                 140

Leu Arg Arg Leu Asp Phe Thr Gly Asn Leu Ile Glu Asp Ile Glu Asp
145                 150                 155                 160

Gly Thr Phe Ser Lys Leu Ser Leu Leu Glu Glu Leu Ser Leu Ala Glu
                165                 170                 175

Asn Gln Leu Leu Lys Leu Pro Val Leu Pro Pro Lys Leu Thr Leu Phe
            180                 185                 190

Asn Ala Lys Tyr Asn Lys Ile Lys Ser Arg Gly Ile Lys Ala Asn Ala
        195                 200                 205

Phe Lys Lys Leu Asn Asn Leu Thr Phe Leu Tyr Leu Asp His Asn Ala
    210                 215                 220

Leu Glu Ser Val Pro Leu Asn Leu Pro Glu Ser Leu Arg Val Ile His
225                 230                 235                 240

Leu Gln Phe Asn Asn Ile Ala Ser Ile Thr Asp Asp Thr Phe Cys Lys
                245                 250                 255

Ala Asn Asp Thr Ser Tyr Ile Arg Asp Arg Ile Glu Glu Ile Arg Leu
            260                 265                 270

Glu Gly Asn Pro Ile Val Leu Gly Lys His Pro Asn Ser Phe Ile Cys
        275                 280                 285

Leu Lys Arg Leu Pro Ile Gly Ser Tyr Phe
    290                 295

<210> SEQ ID NO 71
<211> LENGTH: 27
<212> TYPE: PRT
<213> ORGANISM: Homo sapiens

<400> SEQUENCE: 71

Met Ala Gly Leu Thr Ala Ala Pro Arg Pro Gly Val Leu Leu Leu
1               5                   10                  15

-continued

```
Leu Leu Ser Ile Leu His Pro Ser Arg Pro Gly
            20                  25
```